United States Patent
Heilmann et al.

(10) Patent No.: US 7,655,833 B2
(45) Date of Patent: Feb. 2, 2010

(54) ADS GENES FOR REDUCING SATURATED FATTY ACID LEVELS IN SEED OILS

(75) Inventors: Ingo H. Heilmann, Bay Shore, NY (US); John Shanklin, Shoreham, NY (US)

(73) Assignee: Brookhaven Science Associates, LLC, Upton, NY (US)

( * ) Notice: Subject to any disclaimer, the term of this patent is extended or adjusted under 35 U.S.C. 154(b) by 453 days.

(21) Appl. No.: 10/857,765

(22) Filed: May 28, 2004

(65) Prior Publication Data

US 2005/0039234 A1 Feb. 17, 2005

Related U.S. Application Data

(60) Provisional application No. 60/474,045, filed on May 29, 2003.

(51) Int. Cl.
*C12N 15/82* (2006.01)
*A01H 5/00* (2006.01)

(52) U.S. Cl. ........................ 800/281; 800/298
(58) Field of Classification Search ........................ None
See application file for complete search history.

(56) References Cited

U.S. PATENT DOCUMENTS 5,777,201 A * 7/1998 Poutre et al. ................. 800/281
7,037,692 B1 * 5/2006 Thompson et al. .......... 435/134

FOREIGN PATENT DOCUMENTS

EP 1033405 A2 * 9/2000

OTHER PUBLICATIONS

GenEMBL Sequence Accession AY050838, Yamada et al, Sep. 18, 2002.*
OM Protein Sequence Accession AAG39561, Oct. 18, 2000.*

* cited by examiner

*Primary Examiner*—Elizabeth F McElwain
(74) *Attorney, Agent, or Firm*—Medlen & Carroll, LLP

(57) ABSTRACT

The present invention relates to enzymes involved in lipid metabolism. In particular, the present invention provides coding sequences for *Arabidopsis* Desaturases (ADS), the encoded ADS polypeptides, and methods for using the sequences and encoded polypeptides, where such methods include decreasing and increasing saturated fatty acid content in plant seed oils.

12 Claims, 12 Drawing Sheets

FIG. 1B

ADS1: 1 — 305

ADS2: 1 — 307

ADS3/FAD5: 1 — transit peptide — 71/72 — 371

ADS3/FAD5$^{72-371}$: 72 — 371

FIG. 4

ADS1

A. Nucleic acid coding sequence At1g06080 918 bp atgtcattgtcagcctcggagaaggaggagaataacaagaaaatggcagcggacaaggctgagatggggagga
agaagagggcaatgtgggaaagaaagtggaagagattggacattgtgaaagcttttgcatctctctttgtcca
tttcctctgtctcttggcgccttcaatttcacttggccggctttaagagtcgccctcattgtctatacggtg
ggtgggctcggtatcaccgtctcttaccaccgaaatttggctcaccggagcttcaaagtccctaaatggctcg
agtatttcttcgcttattgcggccttcttgccattcagggagatccgattgattgggtgagcacacatcgata
ccatcaccagtttacagattcggatagggacccacatagtcctaacgaaggattttggttcagtcacctccta
tggctatttgataccggttatcttgtagaaaagtgtggaagaaggacaaatgtggaggacttaaagaggcagt
ggtactataaattcctccaaagaacagtcctttaccacattctaacatttggtttcctcctctattactttgg
tggtttgtcttttcttacttggggaatgggtattggggtagcaatggagcatcatgtgacttgcctcataaac
tctctttgccatgtttggggaagccgaacttggaagactaatgacacttcccgtaacgtttggtggctatcag
tattctcgtttggagagagctggcacaacaatcaccacgccttcgaatcctcggcgagacaaggcttagaatg
gtggcaaatcgacatttcttggtatattgtccgctttctcgagattatcggtttggctactgatgttaagttg
ccttccgagagtcaacgtcgtcgtatggcaatggttcgttga

B. Amino acid sequence translation (NP_172098) 305 aa

MSLSASEKEENNKKMAADKAEMGRKKRAMWERKWKRLDIVKAFASLFVHFLCLLAPFNFTWPALRVALIVYTV
GGLGITVSYHRNLAHRSFKVPKWLEYFFAYCGLLAIQGDPIDWVSTHRYHHQFTDSDRDPHSPNEGFWFSHLL
WLFDTGYLVEKCGRRTNVEDLKRQWYYKFLQRTVLYHILTFGFLLYYFGGLSFLTWGMGIGVAMEHHVTCLIN
SLCHVWGSRTWKTNDTSRNVWWLSVFSFGESWHNNHHAFESSARQGLEWWQIDISWYIVRFLEIIGLATDVKL
PSESQRRRMAMVR

FIG. 5

ADS2

A. Nucleic acid coding sequence At2g31360 924 bp atgtcggtgacatcaacggtggaggagaaccaccagaaaaatccatcaacgccggcggcggtggaggagaaga
agaagaggagatgggtgttttgggatagaaggtggaggagattagattatgtgaaattctcagcttctttcac
tgttcattctcttgctctcttggctccgttttatttcacttggtcggctctttggttacgttttgttttac
accatcggtggtcttggtatcaccgtctcttatcatcgcaacttggctcaccggagtttcaaagtccctaaat
ggcttgagtatctcttagcctattgtgcccttctcgctattcagggagatccgattgattgggtgagtacaca
tcgttaccatcaccagttcacggattcagaacgtgatccacatagtcctaaggaaggttttggtttagtcat
cttctttggatctatgactctgcctatcttgtttcaaagtgtggaagaagagcaaacgtggaggatttgaaga
ggcaatggttttataggtttcttcagaaaacagtgctatttcacattttaggattgggtttctttctcttcta
ccttggtggcatgtccttcgttacttggggaatgggggtaggagcagcattggaagtgcacgtgacttgcctc
ataaattcactctgccatatttggggcactcgaacttggaagaccaatgacacttctcgtaatgtttggtggt
tatcggtattttcatttggagagagttggcacaacaatcatcatgcgttcgagtcatcggctagacaaggact
tgaatggtggcaaatagacatttcgtggtacattgttcggttttcgaaattatcggtttagcgaccgatgtg
aaagtgccaacggaggctcaacgacgtcgtatggctatagttcgttga B. Amino acid sequence translation (NP_180694) 307 aa MSVTSTVEENHQKNPSTPAAVEEKKKRRWVFWDRRWRRLDYVKFSASFTVHSLALLAPFYFTWSALWVTFLFY
TIGGLGITVSYHRNLAHRSFKVPKWLEYLLAYCALLAIQGDPIDWVSTHRYHHQFTDSERDPHSPKEGFWFSH
LLWIYDSAYLVSKCGRRANVEDLKRQWFYRFLQKTVLFHILGLGFFLFYLGGMSFVTWGMGVGAALEVHVTCL
INSLCHIWGTRTWKTNDTSRNVWWLSVFSFGESWHNNHHAFESSARQGLEWWQIDISWYIVRFFEIIGLATDV
KVPTEAQRRRMAIVR

FIG. 6

ADS3

A. Nucleic acid coding sequence At3g15850 1116 bp atggcttctcttctaacaaaacccaaacccgttttcctctgttcaccatcgttatctccaagaactttgaaca
cagcaacaccgtcattgaatttcaccagaatttcattcacccatcaccaaaagcttgctcctttcaagcctcc
tagtctcgttgttgcattctctgaaaagggtttgaagagagatgtcaccacagctgctgcagcgacg
gagggagattacagaaggataatgttatctgatgtgttggtgaagaagaaggaaaaagtagtttggtgggaga
gagaatggaaagctatggactttggagctgttgctgtcgttttgtctatgcatttgcttagtcttttggctcc
gtttcaattcaattggagagctgtttcggttgcttttgggctttatatcgttacaggtcttctggggattact
ctgtctttccataggaatctttctcataaagccttcaagctacctaaatggcttgagtacttgtttgcttatt
gtggagctcaagctcttcagggaaacccaattgattgggtgagtacacataggtaccatcatcagttttgtga
ttcagacagagaccctcatagcccacttgatgggttttggttcggtcacatgaattggatgtttgataccaat
acaatcacccaaaggtgtggagagcctaataatgttggggacttggagaagcagccattctatcgattccttc
gaaccacctacattttgcatccgctggctctagcggttgctttatacgcaatgggtggctttccattcatcgt
ttggggaatgggtgtaagaatagtatgggtatatcatataacttggctagtgaactcagcttgtcatgtatgg
ggaaaacaagcatggaacacaggcgatttgtctaagaacaactggtgggtagcagctctagcattcggggaag
gatggcacaacaatcaccatgcttttgagttctcagctcgacacggctta
gaatggtggcaacttgatatgacttggtacgtcgttaagttccttcaagccatcggtttagcaactgatgtca
agctcccatcggaagctcagaaacaaagaatggcattcaccagcgactga

B. Amino acid sequence translation(BAB02316) 371 aa

MASLLTKPKPVFLCSPSLSPRTLNTATPSLNFTRISFTHHQKLAPFKPPSLVVAFSEKGLKRDVTTAAAATEG
DYRRIMLSDVLVKKKEKVVWWEREWKAMDFGAVAVVLSMHLLSLLAPFQFNWRAVSVAFGLYIVTGLLGITLS
FHRNLSHKAFKLPKWLEYLFAYCGAQALQGNPIDWVSTHRYHHQFCDSDRDPHSPLDGFWFGHMNWMFDTNTI
TQRCGEPNNVGDLEKQPFYRFLRTTYILHPLALAVALYAMGGFPFIVWGMGVRIVWVYHITWLVNSACHVWGK
QAWNTGDLSKNNWWVAALAFGEGWHNNHHAFEFSARHGLEWWQLDMTWYVVKFLQAIGLATDVKLPSEAQKQR
MAFTSD

FIG. 7

ADS3(72-371)

A. Nucleic acid coding sequence based on At3g15850 903 bp atgggagattacagaaggataatgttatctgatgtgttggtgaagaagaaggaaaaagtagtttggtgggaga
gagaatggaaagctatggactttggagctgttgctgtcgttttgtctatgcatttgcttagtcttttggctcc
gtttcaattcaattggagagctgtttcggttgcttttgggctttatatcgttacaggtcttctggggattact
ctgtctttccataggaatctttctcataaagccttcaagctacctaaatggcttgagtacttgtttgcttatt
gtggagctcaagctcttcagggaaacccaattgattgggtgagtacacataggtaccatcatcagttttgtga
ttcagacagagaccctcatagcccacttgatgggttttggttcggtcacatgaattggatgtttgataccaat
acaatcacccaaaggtgtggagagcctaataatgttggggacttggagaagcagccattctatcgattccttc
gaaccacctacattttgcatccgctggctctagcggttgctttatacgcaatgggtggctttccattcatcgt
ttggggaatgggtgtaagaatagtatgggtatatcatataacttggctagtgaactcagcttgtcatgtatgg
ggaaaacaagcatggaacacaggcgatttgtctaagaacaactggtgggtagcagctctagcattcggggaag
gatggcacaacaatcaccatgcttttgagttctcagctcgacacggctta
gaatggtggcaacttgatatgacttggtacgtcgttaagttccttcaagccatcggtttagcaactgatgtca
agctcccatcggaagctcagaaacaaagaatggcattcaccagcgactga

B. Amino acid sequence translation (BAB02316) 300 aa

MGDYRRIMLSDVLVKKKEKVVWWEREWKAMDFGAVAVVLSMHLLSLLAPFQFNWRAVSVAFGLYIVTGLLGIT
LSFHRNLSHKAFKLPKWLEYLFAYCGAQALQGNPIDWVSTHRYHHQFCDSDRDPHSPLDGFWFGHMNWMFDTN
TITQRCGEPNNVGDLEKQPFYRFLRTTYILHPLALAVALYAMGGFPFIVWGMGVRIVWVYHITWLVNSACHVW
GKQAWNTGDLSKNNWWVAALAFGEGWHNNHHAFEFSARHGLEWWQLDMTWYVVKFLQAIGLATDVKLPSEAQK
QRMAFTSD

Figure 9
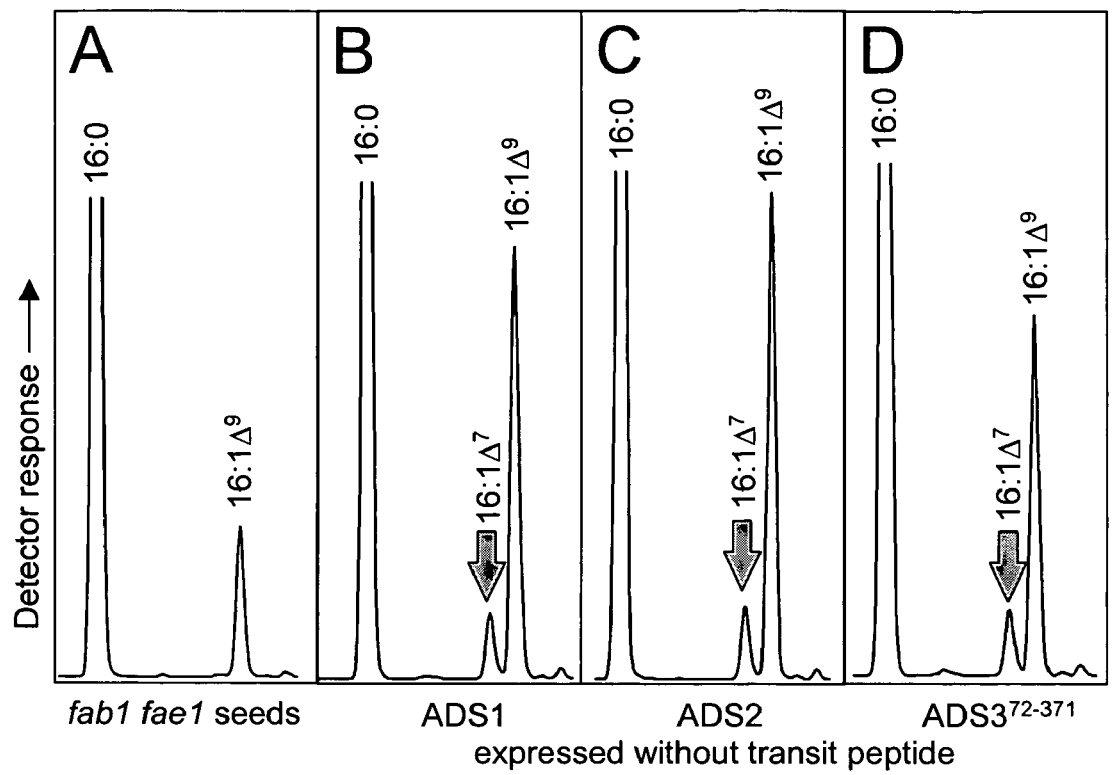
expressed without transit peptide
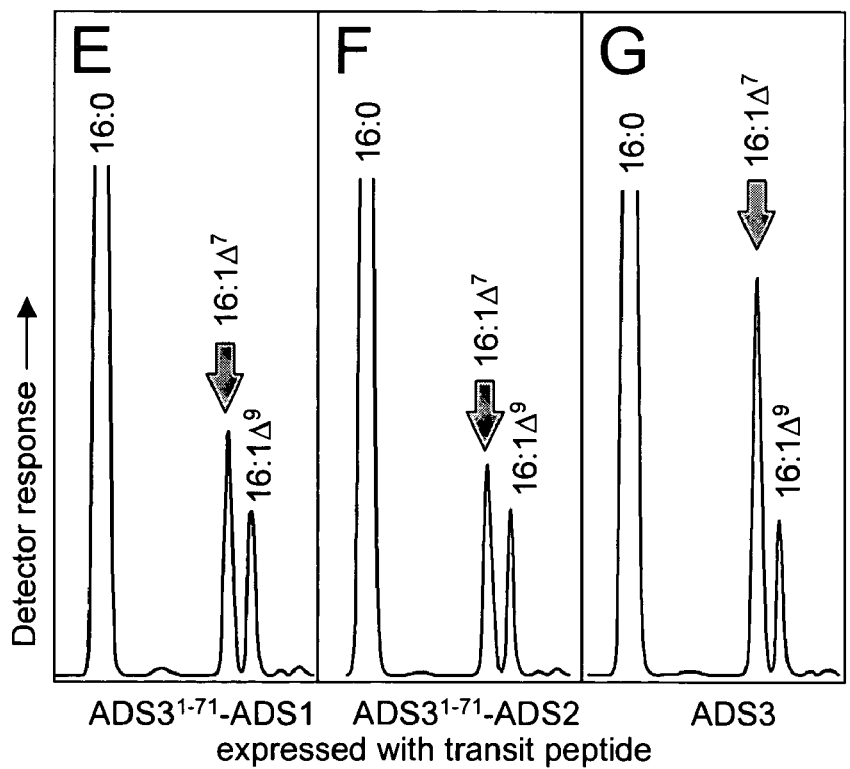
expressed with transit peptide

ADS GENES FOR REDUCING SATURATED FATTY ACID LEVELS IN SEED OILS

This application claims priority to provisional patent application Ser. No. 60/474,045, filed May 29, 2003, which is herein incorporated by reference in its entirety.

The present application was funded in part with government support under grant number DE-AC02-98CH10886, awarded by the US Department of Energy. The government may have certain rights in this invention.

FIELD OF THE INVENTION

The present invention relates to enzymes involved in lipid metabolism. In particular, the present invention provides coding sequences for Arabidopsis Desaturase (ADS), the encoded ADS polypeptides, and methods for using the sequences and encoded polypeptides, where such methods include decreasing and increasing saturated fatty acid content in plant seed oils.

BACKGROUND OF THE INVENTION

Plant metabolism has evolved the ability to produce a diverse range of structures, including more than 20,000 different terpenoids, flavonoids, alkaloids, and fatty acids. Fatty acids have been extensively exploited for industrial uses in products such as lubricants, plasticizers, and surfactants. In fact, approximately one-third of vegetable oils produced in the world are already used for non-food purposes (Ohlrogge, J (1994) Plant Physiol. 104:821-26).

In 1999, approximately 40 million hectares of transgenic crops were planted worldwide. Included in this figure is approximately 50% of the soybean acreage in the United States, over 70% of the Canola acreage in Canada, about 20% of the United States corn crop, and about 33% of the United States cotton crop (Ohlrogge, J (1999) Curr. Opin. Plant Biol. 2:121-22).

Various laboratories around the world have attempted to modify triacylglycerol (TAG) content in oilseed crops by manipulating the genes involved in TAG biosynthesis. The TAG biosynthetic pathway involves many enzymatic reactions. An increasing number of the genes that encode these enzymes have been cloned and studied in detail with respect to the quantitative and qualitative contributions they make to the TAG composition of a particular oilseed. There are still several genes in the TAG pathway, however, that have not been cloned and characterized in detail.

Most of the efforts to modify TAG content have focused on either increasing the nutritional characteristics and chemical stability of edible oils or on introducing new and unusual fatty acids into TAGs for use in various industrial applications. Progress has been achieved through over-expression and/or suppression of a modestly small number of genes in the TAG synthesis pathway. However, to date, the alterations in fatty acid content have not been substantial enough to create truly meaningful new oilseed lines.

Thus, there remains a need to identify and characterize additional genes in the TAG synthesis pathway, the manipulation of which can contribute to altered or increased fatty acid content in oilseeds.

SUMMARY OF THE INVENTION

The present invention relates to enzymes involved in lipid metabolism. In particular, the present invention provides coding sequences for Arabidopsis Desaturase (ADS), the encoded ADS polypeptides, and methods for using the sequences and encoded polypeptides, where such methods include decreasing and increasing saturated fatty acid content in plant seed oils.

Thus, in some embodiments, the present invention provides an isolated nucleic acid sequence comprising a first nucleic acid sequence operably linked to a heterologous promoter, wherein the promoter is a seed specific promoter, and wherein the first nucleic acid sequence comprises a nucleic acid sequence which encodes an ADS polypeptide of SEQ ID NOs:2, 4, 6, or 8 or a protein that is at least 90% identical thereto and which has desaturase activity (e.g., SEQ ID NOs: 1, 3, 5, and 7; an antisense sequence to a nucleic acid sequence which encodes an ADS polypeptide; an antisense sequence to a nucleic acid sequence which encodes SEQ ID NOs:2, 4, 6, or 8 or a protein that is at least 90% identical thereto and which has desaturase activity; an antisense sequence to SEQ ID NOs: 1, 3, 5, or 7; a sequence encoding an siRNA targeted to a sequence in a nucleic acid sequence which encodes an ADS polypeptide; a sequence encoding an siRNA targeted to a sequence in a nucleic acid sequence which encodes SEQ ID NOs:2, 4, 6, or 8 or a protein that is at least 90% identical thereto and which has desaturase activity; or a sequence encoding an siRNA targeted to a sequence in SEQ ID NOs: 1, 3, 5, or 7). In further embodiments, the present invention provides an expression vector comprising any of the nucleic acid sequences of the present invention described above. In other further embodiments, the seed specific promoter is selected from the group consisting of a phaseolin promoter, a napin promoter, an oleosin promoter, and a soybean beta conglycin promoter.

In other embodiments, the present invention provides a plant or plant part comprising any of the isolated nucleic acid sequences described above, wherein the plant or plant part is selected from the group consisting of a plant cell, a plant tissue, a plant organ, a plant seed and a plant. In further embodiments, the plant is an oil-producing species. In yet further embodiments, the oil-producing species is selected from the group consisting of soybean, rapeseed and canola, sunflower, cotton, corn, cocoa, safflower, oil palm, coconut palm, flax, castor, and peanut. In other embodiments, the present invention provides oil from the plant or plant part comprising any of the isolated nucleic acid sequences described above.

In other embodiments, the present invention provides a method of decreasing saturated fatty acid (e.g., 16:0 fatty acids) in plant seed oil, comprising providing a plant comprising a heterologous nucleic acid sequence comprising a first nucleic acid sequence operably linked to a seed specific promoter, wherein the first nucleic acid sequence comprises a nucleic acid sequence which encodes an ADS polypeptide or SEQ ID NOs:2, 4, 6, or 8 or a protein that is at least 90% identical thereto and which has desaturase activity (e.g., SEQ ID NOs:1, 3, 5, and 7); and growing the plant under conditions such that the nucleic acid sequence is expressed and saturated fatty acid content in an oil of a seed of the plant is decreased. In some embodiments, the saturated fatty acid is desaturated at position 7; while in other embodiments, it is desaturated at position 9.

In yet other embodiments, the present invention provides a method of decreasing saturated fatty acid in plant seed oil, comprising transforming a plant with a heterologous nucleic acid sequence comprising a first nucleic acid sequence operably linked to a seed specific promoter, wherein the first nucleic acid sequence comprises a nucleic acid which encodes an ADS polypeptide of SEQ ID NOs:2, 4, 6, or 8 or a protein that is at least 90% identical thereto and which has desaturase activity (e.g., SEQ ID NOs:1, 3, 5, and 7), and growing the plant under conditions such that the heterologous nucleic acid sequence is expressed and saturated fatty acid content in an oil of a seed of the plant is decreased.

In yet other embodiments, the present invention provides a method of decreasing palmitic acid and/or stearic acid in plant seed oil, comprising providing a plant comprising a heterologous nucleic acid sequence comprising a first nucleic acid sequence operably linked to a seed specific promoter, wherein the first nucleic acid sequence comprises a nucleic acid which encodes an ADS polypeptide of SEQ ID NOs:2, 4, 6, or 8 or a protein that is at least 90% identical thereto and which has desaturase activity (e.g., SEQ ID NOs:1, 3, 5, and 7), and growing the plant under conditions such that the nucleic acid sequence is expressed and palmitic acid and/or stearic acid in an oil of a seed of the plant is decreased.

In yet other embodiments, the present invention provides a method of increasing saturated fatty acid in plant seed oil, comprising providing a plant comprising a heterologous nucleic acid sequence comprising a first nucleic acid sequence operably linked to a seed specific promoter, wherein the first nucleic acid sequence comprises a nucleic acid which encodes an ADS polypeptide, an antisense sequence to a nucleic acid sequence which encodes SEQ ID NOs:2, 4, 6, or 8 or a protein that is at least 90% identical thereto and which has desaturase activity (e.g., an antisense sequence to SEQ ID NOs: 1, 3, 5, or 7), a sequence encoding an siRNA targeted to a sequence in a nucleic acid sequence which encodes an ADS polypeptide, a sequence encoding an siRNA targeted to a sequence in a nucleic acid sequence which encodes SEQ ID NOs:2, 4, 6, or 8 or a protein that is at least 90% identical thereto and which has desaturase activity (e.g., an siRNA targeted to a sequence in SEQ ID NOs: 1, 3, 5, or 7), and growing the plant under conditions such that the heterologous nucleic acid sequence is expressed and saturated fatty acid content of an oil of a seed of the plant is increased.

In yet other embodiments, the present invention provides a method of increasing saturated fatty acid in plant seed oil, comprising transforming a plant comprising a heterologous nucleic acid sequence comprising a first nucleic acid sequence operably linked to a seed specific promoter, wherein the first nucleic acid sequence comprises a nucleic acid which encodes an ADS polypeptide, an antisense sequence to a nucleic acid sequence which encodes SEQ ID NOs:2, 4, 6, or 8 or a protein that is at least 90% identical thereto and which has desaturase activity (e.g., an antisense sequence to SEQ ID NOs: 1, 3, 5, or 7), a sequence encoding an siRNA targeted to a sequence in a nucleic acid sequence which encodes an ADS polypeptide, a sequence encoding an siRNA targeted to a sequence in to a nucleic acid sequence which encodes SEQ ID NOs:2, 4, 6, or 8 or a protein that is at least 90% identical thereto and which has desaturase activity (e.g., a sequence encoding an siRNA targeted to a sequence in SEQ ID NOs: 1, 3, 5, or 7), and growing the plant under conditions such that the heterologous nucleic acid sequence is expressed and saturated fatty acid content of an oil of a seed of the plant is increased.

In yet other embodiments, the present invention provides a method of increasing unsaturated acid in plant seed oil, comprising providing a plant comprising a heterologous nucleic acid sequence comprising a first nucleic acid sequence operably linked to a seed specific promoter, wherein the first nucleic acid sequence comprises a nucleic acid sequence which encodes an ADS polypeptide, a nucleic acid sequence which encodes SEQ ID NOs:2, 4, 6, or 8 or a protein that is at least 90% identical thereto and which has desaturase activity (e.g., SEQ ID NOs:1, 3, 5, and 7), and growing the plant under conditions such that the heterologous nucleic acid sequence is expressed and unsaturated fatty acid in an oil of a seed of the plant is decreased.

In yet other embodiments, the present invention provides a method of increasing palmitoleic acid and/or vaccenic acid in plant seed oil, comprising providing a plant comprising a heterologous nucleic acid sequence comprising a first nucleic acid sequence operably linked to a seed specific promoter, wherein the first nucleic acid sequence comprises a nucleic acid sequence which encodes an ADS polypeptide, a nucleic acid sequence which encodes SEQ ID NOs:2, 4, 6, or 8 or a protein that is at least 90% identical thereto and which has desaturase activity (e.g., SEQ ID NOs:1, 3, 5, and 7), and growing the plant under conditions such that the heterologous nucleic acid sequence is expressed and palmitoleic acid and/or vaccenic acid in an oil of a seed of the plant is decreased.

DESCRIPTION OF THE FIGURES

FIG. 4 shows ADS1 nucleic acid coding sequence (Panel A, SEQ ID NO:1) and encoded amino acid sequence (Panel B, SEQ ID NO:2).

FIG. 5 shows ADS2 nucleic acid coding sequence (Panel A, SEQ ID NO:3) and encoded amino acid sequence (Panel B, SEQ ID NO:4).

FIG. 6 shows ADS3 nucleic acid coding sequence (Panel A, SEQ ID NO:5) and encoded amino acid sequence (Panel B, SEQ ID NO:6).

FIG. 7 shows ADS3(72-371) nucleic acid coding sequence (Panel A, SEQ ID NO:7) and encoded amino acid sequence (Panel B, SEQ ID NO:8).

FIG. 9 shows the effect of expressing the *Arabidopsis* desaturase gene without transit peptide, ADS1 (9B), ADS2 (9C) and ADS3$^{72-371}$ (9D), and with transit peptide, ADS3$^{1-71}$-ADS 1 (9E), ADS3$^{1-71}$-ADS2 (9F) and ADS3 (9G), on fatty acid accumulation in fab1 fae1 *Arabidopsis* seeds. Fatty acid accumulation in fab1 fae1 Arabidopsis seeds alone is also shown (9A).

DEFINITIONS

Figure 1A:
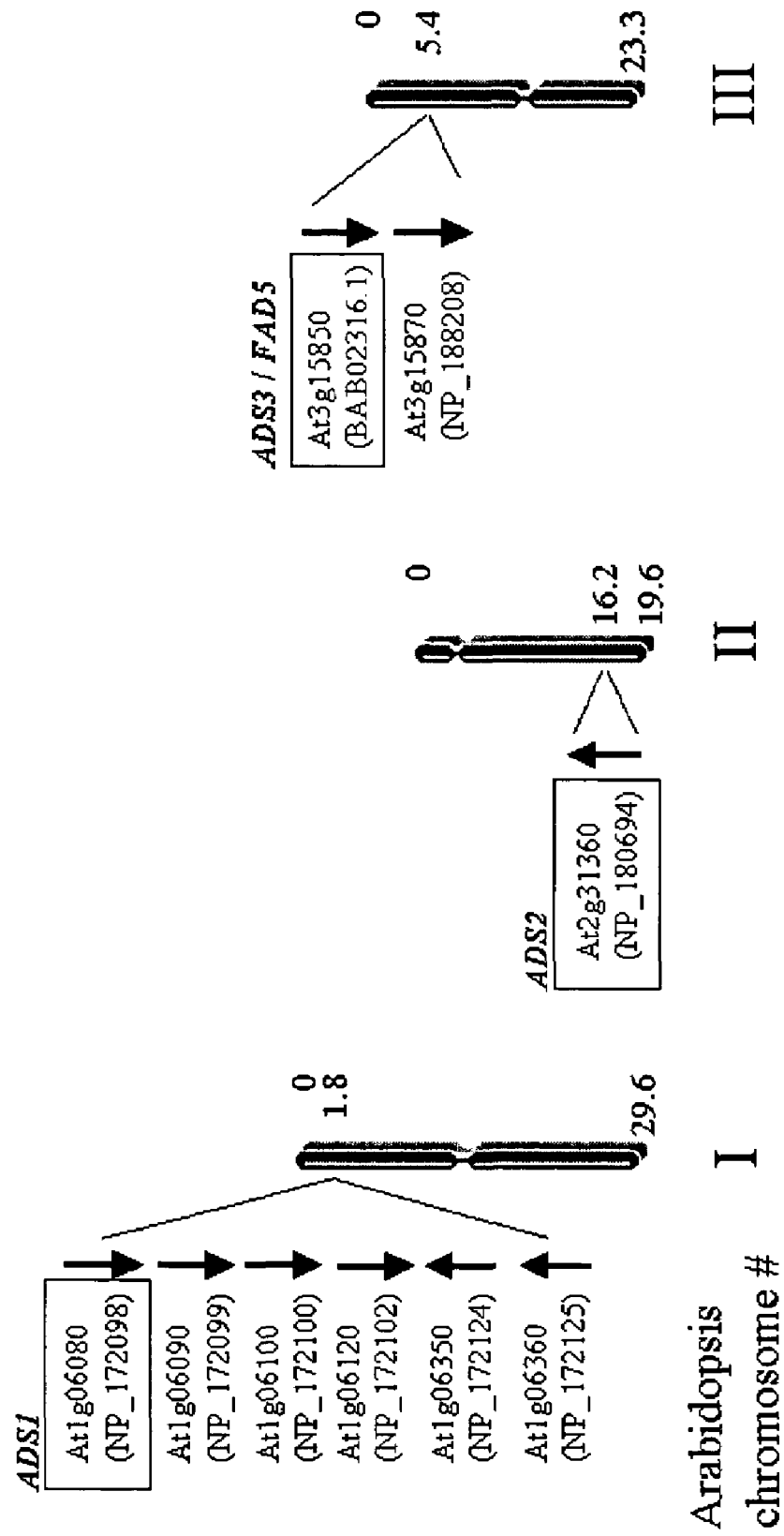
FIG. 1 shows the ADS gene family. Panel A, Location of the ADS genes on *Arabidopsis* chromosomes I, II, and III. ADS1, ADS2, and ADS3 are highlighted by boxes. The numbers indicate the positions of the clusters in Mbp. Arrows indicate orientation 5' to 3'; accession numbers for encoded proteins in brackets. Panel B, Graphical representation of ADS proteins studied in this paper. Numbers indicate amino acid residues.

To facilitate an understanding of the present invention, a number of terms and phrases as used herein are defined below:

The term "plant" is used in it broadest sense. It includes, but is not limited to, any species of woody, ornamental or decorative, crop or cereal, fruit or vegetable plant, and photosynthetic green algae (e.g., *Chlamydomonas reinhardtii*). It also refers to a plurality of plant cells, which are largely differentiated into a structure that is present at any stage of a plant's development. Such structures include, but are not limited to, a fruit, shoot, stem, leaf, flower petal, etc. The term "plant tissue" includes differentiated and undifferentiated tissues of plants including those present in roots, shoots, leaves, pollen, seeds and tumors, as well as cells in culture (e.g., single cells, protoplasts, embryos, callus, etc.). Plant tissue may be in planta, in organ culture, tissue culture, or cell culture. The term "plant part" as used herein refers to a plant structure, a plant organ, or a plant tissue.

The term "crop" or "crop plant" is used in its broadest sense. The term includes, but is not limited to, any species of plant or algae edible by humans or used as a feed for animals or used, or consumed by humans, or any plant or algae used in industry or commerce.

The term "oil-producing species" refers to plant species that produce and store triacylglycerol in specific organs, primarily in seeds. Such species include but are not limited to soybean (*Glycine max*), rapeseed and canola (including *Brassica napus* and *B. campestris*), sunflower (*Helianthus annus*), cotton (*Gossypium hirsutum*), corn (*Zea mays*), cocoa (*Theobrama cacao*), safflower (*Carthamus tinctorius*), oil palm (*Elaeis guineensis*), coconut palm (*Cocos nucifera*), flax (*Linum usitatissimum*), castor (*Ricinus communis*) and peanut (*Arachis hypogaea*). The group also includes non-agronomic species which are useful in developing appropriate expression vectors such as tobacco, rapid cycling *Brassica* species, and *Arabidopsis thaliana*, and wild species which may be a source of unique fatty acids.

The term "*Arabidopsis*" refers to a plant or plants from *Arabidopsis thaliana*.

The term plant cell "compartments or organelles" is used in its broadest sense. The term includes but is not limited to, the endoplasmic reticulum, Golgi apparatus, trans Golgi network, plastids including chloroplasts, proplastids, and leucoplasts, sarcoplasmic reticulum, glyoxysomes, mitochondrial, chloroplast, and nuclear membranes, and the like.

The term "host cell" refers to any cell capable of replicating and/or transcribing and/or translating a heterologous gene.

The terms "diacylglycerol" and "diglyceride" refer to a molecule comprising a glycerol backbone to which two acyl groups are esterified. Typically, the acyl groups are esterified to the sn-1 and sn-2 positions, although the acyl groups may also be esterified to the sn-1 and sn-3 positions, or to the sn-2 and sn-3 positions; the remaining position is unesterified and contains a hydroxyl group. This term may be represented by the abbreviation DAG.

The terms "triacylglycerol" and 'triglyceride" refer to a molecule comprising a glycerol backbone to which three acyl groups are esterified. This term may be represented by the abbreviation TAG.

Fatty acids are referred to in a number of ways. These include, but are not limited to, their common name, and a designation that includes the number of carbon atoms in the chain, the number of double bonds in the fatty acid, and the positions of the double bonds in the fatty acid. For example, oleic acid (the common name) is also referred to as C18:1 delta-9, where the "C18" refers to the number of carbon atoms, the ":1" refers to the number of double bonds, and the "delta-9" refers to the position of the double bond. The terms "delta" and "Δ" are used interchangeably.

The term "*Arabidopsis* desaturase gene" refers to a member of a previously identified but functionally uncharacterized family of nine related *Arabidopsis* desaturase genes with similarity to animal acyl-CoA desaturases, with the capacity to desaturate a saturated fatty acid of preferably 16 or 18 carbons in length. The desaturase is further a delta-7 or a delta-9 desaturase, depending upon the fatty acid substrate and the context of the enzyme activity.

An ADS polypeptide may or may not comprise a transit peptide, and the transit peptide may or may not be naturally occurring. In one non-limiting example, ADS3 comprises a naturally occurring plastid transit peptide, amino acids 1-71 counting from the N-terminus. In another non-limiting example, ADS3 from which the transit peptide has been removed (either naturally, or by a coding sequence which encodes an ADS3 without its naturally occurring transit peptide) is referred to as "ADS3$^{72-371}$" or "ADS3(72-371). The transit peptide of ADS3 is referred to as ADS3$^{1-71}$ or ADS3 (1-71). In yet other non-limiting examples, the ADS3 transit peptide can be added to ADS1 or ADS2, creating fusion proteins; thus, the sequence encoding the ADS transit peptide is fused to ADS1 and ADS2 cDNA fragments (for example, by overlap extension PCR) creating fusion proteins ADS3$^{1-71}$-ADS1 and ADS3$^{1-71}$-ADS2.

The term "ADS-like" refers to a desaturase derived from a plant other than *Arabidopsis*, where the amino acid sequence is highly similar and/or identical to an ADS of the present invention, and which has the same or similar catalytic activity and characteristics as reported here for any of the ADS polypeptides.

The term "transit peptide" refers to a sequence of amino acids (typically a specific N-terminal sequence of amino acids) of a precursor protein (a pre-protein), where the sequence is also referred to as a signal peptide, signal sequence, leader peptide, and where the sequence of amino acids is essential for the initiation of translocation of a protein from its site of synthesis into, or through, a membrane, but where the sequence of amino acids is excised during translocation. Transit peptides are well known in the art, and direct proteins to locations such as the chloroplast, the mitochondria, the endoplasmic reticulum, the tonoplast, the golgi network, and the plasmalemma.

The term "substrate specificity" refers to the range of substrates that an enzyme will act upon to produce a product.

The term "decrease" when used in reference to saturated fatty acid of a plant or plant part and as a result of a treatment of a plant or a plant part refers to a decrease in the saturated fatty acid content, amount, proportion, or composition of a plant or plant part when compared to an untreated plant or plant part of the otherwise same genetic background. A treatment includes but is not limited to a transformed plant or plant part that comprises a heterologous nucleic acid encoding an ADS polypeptide. The decreased saturated fatty acid preferably occurs in the oil of the seeds of the plant. The saturated fatty acid content, amount, proportion, or composition is decreased by about 2%, or about 5%, or about 10%, or about 25%, or about 50%, or about 90% or more of the saturated fatty acid content of an untreated plant.

The term "increase" when used in reference to saturated fatty acid of a plant or plant part and as a result of a treatment of a plant or plant part refers to an increase in the saturated fatty acid content, amount, proportion, or composition of a plant or plant part when compared to an untreated plant or plant part of the otherwise same genetic background. A treatment includes but is not limited to a transformed plant or plant part which comprises a heterologous nucleic acid which results in decreased expression of ADS or an ADS-like polypeptide. The increased saturated fatty acid content, amount, proportion, or composition preferably occurs in the oil of the seeds of the plant. The saturated fatty acid content, amount, proportion, or composition is increased by about 2%, or about 5%, or about 10%, or about 25%, or about 50%, or about 90% or more of the saturated fatty acid content of an untreated plant.

The term "competes for binding" is used in reference to a first polypeptide with enzymatic activity which binds to the same substrate as does a second polypeptide with enzymatic activity, where the second polypeptide is variant of the first polypeptide or a related or dissimilar polypeptide. The efficiency (e.g., kinetics or thermodynamics) of binding by the first polypeptide may be the same as or greater than or less than the efficiency substrate binding by the second polypeptide. For example, the equilibrium binding constants ($K_D$) for binding to the substrate may be different for the two polypeptides.

The terms "protein" and "polypeptide" refer to compounds comprising amino acids joined via peptide bonds and are used interchangeably.

As used herein, "amino acid sequence" refers to an amino acid sequence of a protein molecule. "Amino acid sequence" and like terms, such as "polypeptide" or "protein," are not meant to limit the amino acid sequence to the complete, native amino acid sequence associated with the recited protein molecule. Furthermore, an "amino acid sequence" can be deduced from the nucleic acid sequence encoding the protein.

The term "portion" when used in reference to a protein (as in "a portion of a given protein") refers to fragments of that protein. The fragments may range in size from four amino acid residues to the entire amino sequence minus one amino acid.

The term "homology" when used in relation to amino acids refers to a degree of similarity or identity. There may be partial homology or complete homology (i.e., identity). "Sequence identity" refers to a measure of relatedness between two or more proteins, and is given as a percentage with reference to the total comparison length. The identity calculation takes into account those amino acid residues that are identical and in the same relative positions in their respective larger sequences. Calculations of identity may be performed by algorithms contained within computer programs.

The term "chimera" when used in reference to a polypeptide refers to the expression product of two or more coding sequences obtained from different genes, that have been cloned together and that, after translation, act as a single polypeptide sequence. Chimeric polypeptides are also referred to as "hybrid" polypeptides. The coding sequences include those obtained from the same or from different species of organisms.

The term "fusion" when used in reference to a polypeptide refers to a chimeric protein containing a protein of interest joined to an exogenous protein fragment (the fusion partner). The fusion partner may serve various functions, including enhancement of solubility of the polypeptide of interest, as well as providing an "affinity tag" to allow purification of the recombinant fusion polypeptide from a host cell or from a supernatant or from both. If desired, the fusion partner may be removed from the protein of interest after or during purification.

The term "homolog" or "homologous" when used in reference to a polypeptide refers to a high degree of sequence identity between two polypeptides, or to a high degree of similarity between the three-dimensional structure or to a high degree of similarity between the active site and the mechanism of action. In a preferred embodiment, a homolog has a greater than 60% sequence identity, and more preferable greater than 75% sequence identity, and still more preferably greater than 90% sequence identity, with a reference sequence (e.g., an ADS polypeptide of the present invention including, but not limited to the ADS polypeptides of SEQ ID NOs:6 and 8).

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties (e.g., replacement of leucine with isoleucine). More rarely, a variant may have "non-conservative" changes (e.g., replacement of a glycine with a tryptophan). Similar minor variations may also include amino acid deletions or insertions (in other words, additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on).

The term "gene" refers to a nucleic acid (e.g., DNA or RNA) sequence that comprises coding sequences necessary for the production of an RNA, or a polypeptide or its precursor (e.g., proinsulin). A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "heterologous gene" refers to a gene encoding a factor that is not in its natural environment (i.e., has been altered by the hand of man). For example, a heterologous gene includes a gene from one species introduced into another species. A heterologous gene also includes a gene native to an organism that has been altered in some way (e.g., mutated, added in multiple copies, linked to a non-native promoter or enhancer sequence, etc.). Heterologous genes may comprise plant gene sequences that comprise cDNA forms of a plant gene; the cDNA sequences may be expressed in either a sense (to produce mRNA) or anti-sense orientation (to produce an anti-sense RNA transcript that is complementary to the mRNA transcript). Heterologous genes are distinguished from endogenous plant genes in that the heterologous gene sequences are typically joined to nucleotide sequences comprising regulatory elements such as promoters that are not found naturally associated with the gene for the protein encoded by the heterologous gene or with plant gene sequences in the chromosome, or are associated with portions of the chromosome not found in nature (e.g., genes expressed in loci where the gene is not normally expressed).

The term "oligonucleotide" refers to a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

The term "an oligonucleotide having a nucleotide sequence encoding a gene" or "a nucleic acid sequence encoding" a specified polypeptide refers to a nucleic acid sequence comprising the coding region of a gene or in other words the nucleic acid sequence which encodes a gene product. The coding region may be present in cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The terms "complementary" and "complementarity" refer to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" when used in relation to nucleic acids refers to a degree of complementarity. There may be partial homology or complete homology (i.e., identity). "Sequence identity" refers to a measure of relatedness between two or more nucleic acids, and is given as a percentage with reference to the total comparison length. The identity calculation takes into account those nucleotide residues that are identical and in the same relative positions in their respective larger sequences. Calculations of identity may be performed by algorithms contained within computer programs such as "GAP" (Genetics Computer Group, Madison, Wis.) and "ALIGN" (DNAStar, Madison, Wis.). A partially complementary sequence is one that at least partially inhibits (or competes with) a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a sequence that is completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe which can hybridize to either or both strands of the double-stranded nucleic acid sequence under conditions of low stringency as described infra.

Low stringency conditions when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5× Denhardt's reagent [50× Denhardt's contains per 500 ml: 5 g Ficoll (Type 400, Pharmacia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

High stringency conditions when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1×SSPE, 1.0% SDS at 42° C. when a probe of about 500 nucleotides in length is employed.

It is well known that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low to high stringency as described above.

When used in reference to a single-stranded nucleic acid sequence, the term "substantially homologous" refers to any probe that can hybridize (i.e., it is the complement of) the single-stranded nucleic acid sequence under conditions of low to high stringency as described above.

The term "hybridization" refers to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

The term "$T_m$" refers to the "melting temperature" of a nucleic acid. The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization (1985) in *Nucleic Acid Hybridization*). Other references include more sophisticated computations that take structural as well as sequence characteristics into account for the calculation of $T_m$.

As used herein the term "stringency" refers to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "low" stringency are often required with nucleic acids that are derived from organisms that are genetically diverse, as the frequency of complementary sequences is usually less.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Q β replicase, MDV-1 RNA is the specific template for the replicase (Kacian et al. (1972) Proc. Natl. Acad. Sci. USA, 69:3038). Other nucleic acid will not be replicated by this amplification enzyme. Similarly, in the case of T7 RNA polymerase, this amplification enzyme has a stringent specificity for its own promoters (Chamberlin et al. (1970) Nature, 228:227). In the case of T4 DNA ligase, the enzyme will not ligate the two oligonucleotides or polynucleotides, where there is a mismatch between the oligonucleotide or polynucleotide substrate and the template at the ligation junction (Wu and Wallace (1989) Genomics, 4:560). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.) (1989) *PCR Technology*, Stockton Press).

The term "amplifiable nucleic acid" refers to nucleic acids that may be amplified by any amplification method. It is contemplated that "amplifiable nucleic acid" will usually comprise "sample template."

The term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

The term "polymerase chain reaction" ("PCR") refers to the method of K. B. Mullis U.S. Pat. Nos. 4,683,195, 4,683, 202, and 4,965,188, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

The terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

The term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

The term "reverse-transcriptase" or "RT-PCR" refers to a type of PCR where the starting material is mRNA. The starting mRNA is enzymatically converted to complementary DNA or "cDNA" using a reverse transcriptase enzyme. The cDNA is then used as a "template" for a "PCR" reaction.

The term "RACE" refers to Rapid Amplification of cDNA Ends. Jaen, do you want to expand with 3' and 5' extensions, and some methods and references? Maybe ask Anna?

The term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and into protein, through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

The terms "in operable combination", "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "regulatory element" refers to a genetic element that controls some aspect of the expression of nucleic acid sequences. For example, a promoter is a regulatory element that facilitates the initiation of transcription of an operably linked coding region. Other regulatory elements are splicing signals, polyadenylation signals, termination signals, etc.

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237, 1987). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., Trends Biochem. Sci., 11:287, 1986; and Maniatis, et al., supra 1987).

The terms "promoter element," "promoter," or "promoter sequence" as used herein, refer to a DNA sequence that is located at the 5' end (i.e. precedes) the protein coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

Promoters may be tissue specific or cell specific. The term "tissue specific" as it applies to a promoter refers to a promoter that is capable of directing selective expression of a nucleotide sequence of interest to a specific type of tissue (e.g., seed tissue) in the relative absence of expression of the same nucleotide sequence of interest in a different type of tissue (e.g., leave tissue). Tissue specificity of a promoter may be evaluated by, for example, operably linking a reporter gene to the promoter sequence to generate a reporter construct, introducing the reporter construct into the genome of a plant such that the reporter construct is integrated into every tissue of the resulting transgenic plant, and detecting the expression of the reporter gene (e.g., detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter that is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., immunohistochemical staining. Briefly, tissue sections are embedded in paraffin, and paraffin sections are reacted with a primary antibody that is specific for the polypeptide product encoded by the nucleotide sequence of interest whose expression is controlled by the promoter. A labeled (e.g., peroxidase conjugated) secondary antibody that is specific for the primary antibody is allowed to bind to the sectioned tissue and specific binding detected (e.g., with avidin/biotin) by microscopy.

Promoters may be constitutive or regulatable. The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue. Exemplary constitutive plant promoters include, but are not limited to SD Cauliflower Mosaic Virus (CaMV SD; see e.g., U.S. Pat. No. 5,352,605, incorporated herein by reference), mannopine synthase, octopine synthase (ocs), superpromoter (see e.g., WO 95/14098), and ubi3 (see e.g., Garbarino and Belknap (1994) Plant Mol. Biol. 24:119-127) promoters. Such promoters have been used successfully to direct the expression of heterologous nucleic acid sequences in transformed plant tissue.

In contrast, a "regulatable" promoter is one which is capable of directing a level of transcription of an operably linked nuclei acid sequence in the presence of a stimulus (e.g., heat shock, chemicals, light, etc.) which is different from the level of transcription of the operably linked nucleic acid sequence in the absence of the stimulus.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (i.e., molecular biological techniques) such that transcription of the gene is directed by the linked enhancer or promoter. For example, an endogenous promoter in operable combination with a first gene can be isolated, removed, and placed in operable combination with a second gene, thereby making it a "heterologous promoter" in operable combination with the second gene. A variety of such combinations are contemplated (e.g., the first and second genes can be from the same species, or from different species).

The presence of "splicing signals" on an expression vector often results in higher levels of expression of the recombinant transcript in eukaryotic host cells. Splicing signals mediate the removal of introns from the primary RNA transcript and consist of a splice donor and acceptor site (Sambrook, et al. (1989) *Molecular Cloning: A Laboratory Manual*, 2nd ed., Cold Spring Harbor Laboratory Press, New York, pp. 16.7-16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly (A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly(A) signal. The SV40 poly(A) signal is contained on a 237 bp BamHI/BclI restriction fragment and directs both termination and polyadenylation (Sambrook, supra, at 16.6-16.7).

The term "selectable marker" refers to a gene which encodes an enzyme having an activity that confers resistance to an antibiotic or drug upon the cell in which the selectable marker is expressed, or which confers expression of a trait which can be detected (e.g., luminescence or fluorescence). Selectable markers may be "positive" or "negative." Examples of positive selectable markers include the neomycin phosphotransferase (NPTII) gene that confers resistance to G418 and to kanamycin, and the bacterial hygromycin phosphotransferase gene (hyg), which confers resistance to the antibiotic hygromycin. Negative selectable markers encode an enzymatic activity whose expression is cytotoxic to the cell when grown in an appropriate selective medium. For example, the HSV-tk gene is commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme.

The term "vector refers to nucleic acid molecules that transfer DNA segment(s) from one cell to another. The term "vehicle" is sometimes used interchangeably with "vector."

The terms "expression vector" or "expression cassette" refer to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The term "transfection" refers to the introduction of foreign DNA into cells. Transfection may be accomplished by a variety of means known to the art including calcium phosphate-DNA co-precipitation, DEAE-dextran-mediated transfection, polybrene-mediated transfection, glass beads, electroporation, microinjection, liposome fusion, lipofection, protoplast fusion, viral infection, biolistics (i.e., particle bombardment) and the like.

The terms "infecting" and "infection" when used with a bacterium refer to co-incubation of a target biological sample, (e.g., cell, tissue, etc.) with the bacterium under conditions such that nucleic acid sequences contained within the bacterium are introduced into one or more cells of the target biological sample.

The term "*Agrobacterium*" refers to a soil-borne, Gram-negative, rod-shaped phytopathogenic bacterium that causes crown gall. The term "*Agrobacterium*" includes, but is not limited to, the strains *Agrobacterium tumefaciens*, (which typically causes crown gall in infected plants), and *Agrobacterium rhizogens* (which causes hairy root disease in infected host plants). Infection of a plant cell with *Agrobacterium* generally results in the production of opines (e.g., nopaline, agropine, octopine etc.) by the infected cell. Thus, *Agrobacterium* strains which cause production of nopaline (e.g., strain LBA4301, C58, A208, GV3101) are referred to as "nopaline-type" Agrobacteria; *Agrobacterium* strains which cause production of octopine (e.g., strain LBA4404, Ach5, B6) are referred to as "octopine-type" Agrobacteria; and *Agrobacte-*

*rium* strains which cause production of agropine (e.g., strain EHA105, EHA101, A281) are referred to as "agropine-type" Agrobacteria.

The terms "bombarding, "bombardment," and "biolistic bombardment" refer to the process of accelerating particles towards a target biological sample (e.g., cell, tissue, etc.) to effect wounding of the cell membrane of a cell in the target biological sample and/or entry of the particles into the target biological sample. Methods for biolistic bombardment are known in the art (e.g., U.S. Pat. No. 5,584,807, the contents of which are incorporated herein by reference), and are commercially available (e.g., the helium gas-driven microprojectile accelerator (PDS-1000/He, BioRad).

The term "microwounding" when made in reference to plant tissue refers to the introduction of microscopic wounds in that tissue. Microwounding may be achieved by, for example, particle bombardment as described herein.

The term "transgenic" when used in reference to a plant or fruit or seed (i.e., a "transgenic plant" or "transgenic fruit" or a "transgenic seed") refers to a plant or fruit or seed that contains at least one heterologous gene in one or more of its cells. The term "transgenic plant material" refers broadly to a plant, a plant structure, a plant tissue, a plant seed or a plant cell that contains at least one heterologous gene in one or more of its cells.

The terms "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

The term "wild-type" when made in reference to a gene refers to a gene that has the characteristics of a gene isolated from a naturally occurring source. The term "wild-type" when made in reference to a gene product refers to a gene product, which has the characteristics of a gene product isolated from a naturally occurring source. A wild-type gene is that which is most frequently observed in a population and is thus arbitrarily designated the "normal" or "wild-type" form of the gene. In contrast, the term "modified" or "mutant" when made in reference to a gene or to a gene product refers, respectively, to a gene or to a gene product which displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "antisense" refers to a deoxyribonucleotide sequence whose sequence of deoxyribonucleotide residues is in reverse 5' to 3' orientation in relation to the sequence of deoxyribonucleotide residues in a sense strand of a DNA duplex. A "sense strand" of a DNA duplex refers to a strand in a DNA duplex that is transcribed by a cell in its natural state into a "sense mRNA." Thus an "antisense" sequence is a sequence having the same sequence as the non-coding strand in a DNA duplex. The term "antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, i.e., at the 5' non-coding sequence, 3' non-coding sequence, introns, or the coding sequence. In addition, as used herein, antisense RNA may contain regions of ribozyme sequences that increase the efficacy of antisense RNA to block gene expression. "Ribozyme" refers to a catalytic RNA and includes sequence-specific endoribonucleases. "Antisense inhibition" refers to the production of antisense RNA transcripts capable of preventing the expression of the target protein.

The term "siRNAs" refers to short interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "target RNA molecule" refers to an RNA molecule to which at least one strand of the short double-stranded region of an siRNA is homologous or complementary. Typically, when such homology or complementary is about 100%, the siRNA is able to silence or inhibit expression of the target RNA molecule. Although it is believed that processed mRNA is a target of siRNA, the present invention is not limited to any particular hypothesis, and such hypotheses are not necessary to practice the present invention. Thus, it is contemplated that other RNA molecules may also be targets of siRNA. Such targets include unprocessed mRNA, ribosomal RNA, and viral RNA genomes.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

The term "posttranscriptional gene silencing" or "PTGS" refers to silencing of gene expression in plants after transcription, and appears to involve the specific degradation of mRNAs synthesized from gene repeats.

The term "overexpression" refers to the production of a gene product in transgenic organisms that exceeds levels of production in normal or non-transformed organisms. The term "cosuppression" refers to the expression of a foreign gene that has substantial homology to an endogenous gene resulting in the suppression of expression of both the foreign and the endogenous gene. The term "altered levels" refers to the production of gene product(s) in transgenic organisms in amounts or proportions that differ from that of normal or non-transformed organisms.

The term "recombinant" when made in reference to a nucleic acid molecule refers to a nucleic acid molecule that is comprised of segments of nucleic acid joined together by means of molecular biological techniques. The term "recombinant" when made in reference to a protein or a polypeptide refers to a protein molecule that is expressed using a recombinant nucleic acid molecule.

The terms "Southern blot analysis" and "Southern blot" and "Southern" refer to the analysis of DNA on agarose or acrylamide gels in which DNA is separated or fragmented according to size followed by transfer of the DNA from the gel to a solid support, such as nitrocellulose or a nylon membrane. The immobilized DNA is then exposed to a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al. (1989) *Molecular Cloning: A Laboratory Manual*, Cold Spring Harbor Press, NY, pp 9.31-9.58).

The term "Northern blot analysis" and "Northern blot" and "Northern" as used herein refer to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al. (1989) supra, pp 7.39-7.52).

The terms "Western blot analysis" and "Western blot" and "Western" refers to the analysis of protein(s) (or polypeptides) immobilized onto a support such as nitrocellulose or a membrane. A mixture comprising at least one protein is first separated on an acrylamide gel, and the separated proteins are then transferred from the gel to a solid support, such as nitrocellulose or a nylon membrane. The immobilized proteins are exposed to at least one antibody with reactivity against at least one antigen of interest. The bound antibodies may be detected by various methods, including the use of radiolabeled antibodies.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a plant DAGAT includes, by way of example, such nucleic acid in cells ordinarily expressing a DAGAT, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may single-stranded), but may contain both the sense and anti-sense strands (i.e., the oligonucleotide may be double-stranded).

The term "purified" refers to molecules, either nucleic or amino acid sequences, which are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated. The term "purified" or "to purify" also refer to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "sample" is used in its broadest sense. In one sense it can refer to a plant cell or tissue. In another sense, it is meant to include a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

DESCRIPTION OF THE INVENTION

The present invention relates to enzymes involved in lipid metabolism. In particular, the present invention provides coding sequences for *Arabidopsis* Desaturase (ADS), the encoded ADS polypeptides, and methods for using the sequences and encoded polypeptides, where such methods include decreasing and increasing saturated fatty acid content in plant seed oils.

The description below provides specific, but not limiting, illustrative examples of embodiments of the present invention. This description includes characterization of ADS members of a previously functionally uncharacterized family of nine related *Arabidopsis* desaturase genes with similarity to animal acyl-CoA desaturases. Thus, the present invention provides ADS polypeptides, and in particular ADS1, ADS2, and preferably ADS3 polypeptides, truncated ADS polypeptides, ADS coding sequences, methods of identifying ADS polypeptides and coding sequences, methods of characterizing ADS function, methods of expressing ADS coding sequences, and methods of utilizing ADS coding sequences and polypeptides, including but not limited to methods of manipulating ADS activity in plants and methods of decreasing and increasing saturated fatty acid content of seed oils.

I. Characterization of ADS Genes

Desaturation of plant fatty acids can occur on acyl chains that are esterified in different substrate configurations. In the chloroplast, newly-synthesized saturated fatty acyl-chains bound to acyl-carrier-protein (ACP) are desaturated by a soluble acyl-ACP desaturase, resulting in monounsaturated fatty acid. Most further desaturation to dienoic or trienoic fatty acids occurs by membrane-bound desaturases in the endoplasmic reticulum (ER) after transesterification on acyl-chains esterified in phosphatidyl choline (PC) or, potentially, on acyl-chains esterified to co-enzyme A (CoA), although some further desaturation also occurs in the plastid. Most enzymes in the pathways involved in the generation and interconversion of desaturated fatty acids have previously been cloned and biochemically characterized, often revealing properties with potential for biotechnological applications. Moreover, desaturases differ in both their regioselectivity (also regiospecificity, or where a double bond is formed in a fatty acyl chain), and in their substrate specificity (which fatty acyl group is preferred, and in what form), where substrate specificity is used to classify desaturases.

Based on sequence homology, Fukuchi-Mizutani et al. (Plant Cell. Phisiol. 39:247 (1998)) isolated two cDNA clones from *Arabidopsis* that resemble prokaryotic acyl-CoA/acyl-lipid desaturases and termed them ADS1 and ADS2. ADS1 and ADS2 mRNA was present in petals, and mRNA levels changed differentially with cold-treatment. With a focus on the analysis of expression patterns of the plant genes, no attempt was made by Fukuchi-Mizutani and coworkers to functionally characterize the desaturase-like gene products.

The *Arabidopsis* genome contains nine genes with significant homology to the two cDNAs identified by Fukuchi-Mizutani et al., distributed in two clusters on chromosomes I and III and a single gene on chromosome II (FIG. 1A). These genes are referred to as ADS genes, for *Arabidopsis* desaturase genes. Cloning sequences ADS1 and ADS2 were previously identified, as described above, but not functionally characterized. In another report, a tandem of genes in chromosome 3 that encodes two proteins similar to animal and fungal acyl-CoA desaturase were identified as putative FAD5.1 and FAD5.2 genes (Mekhedov et al. (2000) Plant Physiol 122:389). The fad5 mutation results in decreased desaturation of fatty acids esterified to monogalactosyl diacylglycerol (MGDG) in the plastid, which in the non-mutant plant leads to the production of 16:3 in the plastid (Kunst et al., 1989, Plant Physiol 90:943; Hugly et al. 1991); the fad5 mutation also causes increased susceptibility to photoinhibition compared to wild type plants (Vijayan and Browse, 2002, Plant Physiol 129:876). Thus, the FAD5 gene product is believed to be a Δ7 desaturase, as it is believed to act upon C16:0 esterified to MGDG, resulting in C16:1Δ7 (it is referred to as a MGDG desaturase (palmitate-specific) by Mekhedov et al. (2000), supra). The identification of the two putative FAD5 genes (Mekhedov et al. (2000), supra) was based upon a survey of public plant genomic databases, and upon four criteria that included sequence similarity to acyl-CoA desaturases, presence of transit peptides, chromosomal location, and association with the presence of C16:3 fatty acids. The report further noted that putative FAD5.1 does not have ESTs in *Arabidopsis*. Expression of ADS1 in *Brassica juncea* resulted in a decreased level of total saturated fatty acids (Yao et al., Plant Biotechnology, 1:221 (2003) and US patent publication 20030056246).

To characterize members of this gene family, ADS1 and ADS2 were selected, as well as ADS3, as a representative of the gene cluster on chromosome III (FIG. 1B). ADS3 differs from ADS1 and ADS2 in that it contains a 210 bp sequence at its 5' end, which is predicted to encode a chloroplast transit peptide by ChloroP software (FIG. 1B). It also appears, from the Inventors' results described below, that the ADS3 gene is the locus of the *Arabidopsis* fad5 mutation, and thus may represent an FAD5 gene. Although Mekhedov et al. (2000) (supra) lists two genes, putative FAD5.1 and FAD5.2, which contain a plastid transit peptide, there is no evidence for the presence of a second gene in the *Arabidopsis* genome with homology to a member of the ADS gene family and which contains a transit peptide sequence, other than ADS3.

A gene product of a white spruce cDNA that has sequence similarity to ADS3 has recently been characterized by heterologous expression in yeast; in this system, the spruce gene acts as an 18:0 Δ9 desaturase (Marillia et al., 2002). This activity as an 18:0 Δ9 desaturase is in contradiction to the function of FAD5 (which appears to be ADS3 characterized by the Inventors) as C16:0 Δ7 desaturase as proposed by Mekhedov et al. (2000) (supra). Thus, one objective of the functional characterization of ADS1, ADS2, and ADS3 was to investigate the identity of the ADS3 (or FAD5 gene) through heterologous expression in yeast and over-expression in *Arabidopsis*.

Gene sequences for the three ADS genes were obtained from the from The *Arabidopsis* Information Resource (TAIR) database website (http://godot.ncgr.org/home.html). cDNA coding fragments for all three ADS genes were generated by polymerase chain reaction (PCR) from *Arabidopsis* flower cDNA using primers, as described in Example 1. These cDNA sequences were subsequently isolated and used in the experiments described below and in the Examples; sequencing of the cDNA fragments indicated no discrepancies between the generated cDNA sequences and the database reported sequences.

The results of the investigations demonstrated that when expressed in yeast, the gene products of ADS1, ADS2 and ADS3 exhibited enzymatic activity as fatty acyl desaturases. In all yeast expression experiments, the activities of the three gene products were found to be indistinguishable. The preferred substrate was palmitic acid, although stearic acid was also accepted, and desaturation of fatty acid substrates endogenous to yeast occurred in the Δ9 position. Surprisingly, when expressed in plants, over-expression of the same ADS desaturases in *Arabidopsis* seeds results in the same fatty acid products as were observed in yeast, and an additional fatty acid product, 16:1 Δ7. This is the first report of a discrepancy between the desaturation patterns observed after heterologous expression of fatty acid desaturases in yeast and those observed after expression of the same genes in *Arabidopsis*. These results are described in more detail below.

*Arabidopsis* ADS Gene Family

The ADS gene family is the largest family of desaturases in *Arabidopsis*; these are a functionally uncharacterized family of nine related *Arabidopsis* desaturase genes with similarity to animal acyl-CoA desaturases. Three family members were selected for functional characterization, two of which, ADS1 and ADS2 were identified as ESTs and had previously been shown to have temperature and tissue specific expression, and a third of which, ADS3, is also referred to as putative FAD5 (16:0 Δ7 desaturase), as identified by Mekhedov (2000) (supra), based on its proximity to the mapped location of the fad5 mutation. Only one of the nine, ADS3, encodes an N-terminal transit peptide extension, which suggests a plastidial location for ADS3, but an extraplastidial location for the other eight family members.

ADS Expression in Yeast

Expression of either ADS1, ADS2, or ADS3$^{72-371}$ (encoding ADS3 lacking its transit peptide) in a yeast Δ9 desaturase deletion strain (DTY11A) rescues the unsaturated fatty acid auxotrophy, as any of these ADS genes enabled DTY11A yeast to grow in the absence of unsaturated fatty acid supplementation, indicating they are functional desaturases able to complement the ole1Δ mutation. Fatty acid analyses of the complemented yeast strains showed that all three ADS gene products preferred 16:0 over 18:0 as substrates. The production of palmitoleic (C16:1 Δ9), oleic (C18:1 Δ9), and vaccenic (C18:1 Δ911) acid in yeast indicates desaturation of palmitic (C16:0) and stearic (C18:0) acid at the Δ9 position, with some elongation of palmitoleic to vaccenic acid. These observations of Δ9 desaturation specificity in yeast is consistent with the observations of Marillia et al. (2002), who expressed in yeast a white spruce cDNA clone encoding a desaturase with significant similarity to the ADS desaturase sequences (without attempting functional complementation of an auxotroph). While the publication reported that regiospecificity of the desaturase based on an in vitro assays was Δ9, the chain length specificity was reversed with respect to the specificity observed for the ADS enzymes; in other words, the spruce cDNA product expressed in yeast preferred 18:0 to 16:0. The spruce desaturase was most similar to the ADS3 gene in that it too had an N-terminal transit peptide. However, the ADS3 and spruce constructs differed in that the ADS construct expressed in yeast was an engineered ADS3$^{72-371}$ construct, which removed the transit peptide from ADS3, whereas the publication reports that the transit peptide of the spruce gene was left intact. While it seems unlikely that the presence of a transit peptide would affect the specificity, it may have contributed to the very low activity reported for the expressed product by Marillia et al. (2002).

When the transgenic yeast cultures were supplemented, by supplying saturated fatty acids to DTY11A cultures expressing the ADS desaturases, the addition of palmitic acid resulted in denser growth than that of any other fatty acid, consistent with 16:0 as a preferred substrate. An explanation for these results is that the presentation of exogenous saturated fatty acids has been reported to inhibit endogenous fatty acid synthesis (Choi et al., J. Biol. Chem. 271:3581 (1996)), thereby limiting fatty acids available for desaturation to the ones supplied in the media. Growth in supplemented media in DTY11A expressing ADS genes is slower than that of the parent line expressing the yeast ole1 desaturase, which suggests that unsaturated fatty acids are limiting to growth. As a preferred substrate, palmitic acid therefore supported growth to a degree exceeding that of unsupplemented cultures. This explanation is also consistent with the observation that most fatty acid supplementation inhibited growth compared to unsupplemented cultures. Because ADS3 had previously been proposed to be responsible for plastidial 16:0 Δ7 desaturation by Mekhedov, it was surprising that no Δ7 products were detected in yeast. These yeast expression studies were thus in apparent conflict with the proposal that ADS3 was a putative FAD5, because even with the most sensitive of analysis it was not possible to detect significant accumulation of the FAD5 product, 16:1 Δ7.

ADS Expression in Plants

To further investigate this apparent conflict, ADS genes were expressed in planta. The observation that palmitic acid was a preferred-chain-length substrate for the ADS desaturases in yeast raised the question of whether these enzymes could be used to lower the levels of palmitic acid in plant seeds. ADS1, ADS2, ADS3$^{72-371}$, and ADS3 were thus expressed in developing fab1 fae1 Arabidopsis seeds, where the fab1 fae1 is a double mutant that contains increased levels of 16:0 fatty acids. As a result of the expression of the ADS desaturases in Arabidopsis, palmitic acid levels decreased significantly by a margin of 8-10% of the total fatty acid. This decrease was observed in all transgenic seeds analyzed; there were, however, differences in the patterns of desaturated fatty acids formed between plants expressing ADS1, ADS2, or ADS3$^{72-371}$ and plants expressing ADS3.

Plants expressing ADS1, ADS2, or ADS3$^{72-371}$ desaturases accumulated small amounts of 16:1 Δ7 in addition to 16:1 Δ9, 18:1 Δ9, and 18:1 Δ11, which had previously been observed to accumulate in yeast. Thus, expression of ADS1, ADS2 and ADS3$^{72-371}$ resulted in the accumulation of palmitoleic and vaccenic acids (approximately 9% combined), and (approximately 0.6%) 16:1 Δ7, with concomitant decreases in the level of palmitic acid. Intriguingly, expression of all of these three genes led to reductions of approximately 10% of 18:1 Δ9, and a concomitant increase in the accumulation of 18:3. It was initially hypothesized that this 18:3 was a desaturation product of the introduced ADS, in other words C18:3 delta-7,9,12, but GC-MS analysis showed it to be C18:3 delta-9,12,15. Thus, its accumulation was not directly caused by interaction with the desaturase, but some secondary effect. These transgenic plants also accumulate increased levels of 18:1D11, and it is contemplated that this fatty acid may act as a signal to upregulate Fad2 and Fad3, the downstream desaturases.

As noted above, Arabidopsis seed expression of ADS desaturases lacking transit peptides generated a mixture of Δ9 and Δ7 desaturation products from palmitic acid. The formation of vaccenic acid in transgenic fab1 fae1 seeds implies that palmitoleic acid was elongated despite a knockout mutation in FAE1, which effectively prevented the formation of fatty acids longer than 20 carbons. With elongation taking place in the ER despite the fae1 mutation, C 16:1 Δ7 could in theory be elongated to C18:1 Δ9, which would not distinguishable from C18:1 Δ9 generated in the plastid. However, the fact that the sum of C16:1 Δ7, C16:1 Δ9, and C18:1 Δ11 (approximately 10%) is approximately equal to the loss of C16:0 suggests that any elongation of C16:1Δ7 is very minor component of the accumulated fatty acids.

Fatty acid desaturases generally are highly stereo-specific, both for the binding of their substrates and for the regiospecificity of the respective desaturation catalyzed. When the ADS genes were expressed in yeast, this was indeed the case, with desaturation being confined to the 9-position. When expressed in plants, the ADS3 gene product exhibited a different regiospecificity when expressed with or without a plastid-targeting transit peptide. Thus, expression of the full length ADS3 (with its transit peptide) resulted in the accumulation of 16:1 Δ7 (approximately 3.5%) and 16:1 Δ9 (approximately 1%). The levels of ADS3 activity with, and without, its transit peptide, were similar, in that their products accumulated to about 9% of total fatty acids when expressed without the transit peptide and to about 4.5% total fatty acids with transit peptide intact. However, the regiospecificity was strongly affected by the presence or absence of the transit peptide: the ratio of Δ9:Δ7 desaturation by the ADS1, 2 or ADS3$^{72-371}$ was approximately 15:1, while full length ADS3 accumulated a Δ9:Δ7 ratio of approximately 1:3.5. Thus, expression of ADS1, ADS2 and ADS3$^{72-371}$, which lack a transit peptide, resulted in a predominant regiospecificity for the 9-position, whereas in contrast, expression of full length ADS3, which includes a transit peptide, resulted in a reversed regiospecificity and in favor of the 7-position.

Although it is not necessary to understand the mechanism of the invention, and the invention is not intended to be limited by any particular mechanism, there is more than one interpretation of the data of ADS expression in plants. One interpretation is that ADS is bifunctional, as has been reported for several lipid modification enzymes such as the Lesquerella bifunctional desaturase/hydroxylase (Bruin). An alternate interpretation is that while the majority of the overexpressed ADS3 was successfully imported into plastids, a small fraction accumulated extraplastidially. Support for the latter hypothesis comes from wild type Arabidopsis, in which approximately 15% of the fatty acids in leaf tissue are C16:3 fatty acids derived from C16:1Δ7. In these plants, the combined levels of C16:1Δ9 and C18:1 Δ11 are approximately 1-2%, suggesting that the Fad5 enzyme shows a very strong preference for Δ7 regiospecificity.

A strong preference for Δ7 regiospecificity raises the question as to what factor(s) could result in a switch in regiospecificity of >35 fold, based solely on subcellular location. One likely factor is the significant differences between the lipid environments of the plastid and the ER, others include the presence of different electron donors, cytochrome b5 in the ER as opposed to ferredoxin in the plastid. This lipid environment could influence the desaturase enzyme directly, affecting its regiospecificity, or more likely could result in the presentation of the fatty acid substrate on different head groups because Fad5 has been shown to specifically desaturate 16:0 esterified to MGDG. It is interesting to note that when ADS3 was expressed (without a plastidial targeting transit peptide) in an extraplastidial location, its products accumulated to almost twice the levels that they did in its native plastidial location. This suggests that while the regiospecificity of the desaturase was greatly affected, the efficiency of desaturation was affected little by the presence of alternate head groups and by interaction with a cytochrome b5 in place of ferredoxin. The low level of C16:1 Δ7 accumulation resulting from ADS gene expression in the ER might have occurred with substrate esterified to a small pool of extraplastidial MGDG proposed by Benning.

In summary, an ADS without a transit peptide, such as ADS1, ADS2 and ADS3$^{72-371}$, are functionally equivalent to each other when expressed in either yeast or in *Arabidopsis* because their expression results in accumulation unsaturated of fatty acids to very similar levels and with similar profiles. Moreover, an ADS without a transit peptide, such as ADS1, 2 and ADS3, is capable of Δ7-desaturation with similar levels (approximately 1%) of C16:1Δ7 accumulation in transgenic plants. In contrast, the presence of absence of a transit peptide, such as is observed with full-length or truncated ADS3, is capable of Δ9 and Δ7 regiospecific desaturation depending on the context of expression; Δ9 expression outside the plastid (or without a transit peptide) and Δ7 when expressed inside the plastid (or with its transit peptide intact). It is contemplated that compartment specific factors such as substrate head group or cofactors (in other words, electron donors such as cytochrome b5 in the ER or ferredoxin in the plastid) play a role in modulating regiospecificity. These data are consistent with the proposal that ADS3 is responsible for the Fad5 phenotype.

Results obtained from yeast and plant expression were inconsistent. Because yeast is a commonly used heterologous system to evaluate the specificity of desaturases, the results described above demonstrate that these results can be misleading. Thus, while yeast is a generally useful tool in understanding the function of plant genes, caution should be used in over-interpreting the results of such studies in the absence of confirmatory in planta transgenic analysis.

Changes in Regiospecificity

The functionality, substrate specificity and regiospecificity of enzymes typically evolve by the accumulation of mutations until new properties arise. However, emerging evidence suggests enzyme functionality can also be influenced by metabolic context. Experiments conducted during the course of development of the present invention demonstrated that when the plastidial *Arabidopsis* 16:0-D7-desaturase FAD5 was retargeted to the cytoplasm, regiospecificity shifted 70-fold, D7 to D9. Conversely, retargeting of two related cytoplasmic 16:0-D9-desaturases (ADS1 and ADS2) to the plastid, shifted regiospecificity ~25-fold, D9 to D7. All three desaturases exhibited D9-regiospecificity when expressed in yeast. Coexpression of each enzyme with cucumber monogalactosyldiacylglycerol (MGDG)-synthase conferred D7-desaturation, via presentation of 16:0 on the plastidial lipid MGDG. Positional analysis is consistent with ADS desaturation on MGDG. The finding that a lipid headgroup can act as a molecular switch for desaturase regiospecificity is unprecedented. The present invention is not limited to a particular mechanism (nor is an understanding of the mechanism necessary to practice the present invention). Nonetheless, it is contemplated that the data presented here suggest that FAD5 D7-regiospecificity evolved by retargeting of the enzyme to the plastid via the addition of a plastidial transit peptide to a cytoplasmic desaturase, rather than by the accumulation of changes in the catalytic portion of the enzyme. Retargeting to the plastid provided access to an alternative substrate pool, enabling plants to synthesize 16:1D7, and its abundant metabolite, 16:3D7,10,13. A bioinformatics analysis of the *Arabidopsis* genome was performed to investigate the generality of alternate targeting within other protein families. Using stringent criteria, 239 protein families were identified that contain members with predicted targeting to different subcellular compartments. Because many plant enzymes are capable of accepting various substrates, and because compartments contain distinct complements of metabolites, diversification of enzyme function by alternative subcellular targeting represents a potential, and hereto unrecognized, source of metabolic diversity.

Changes to an enzyme's regiospecificity typically require between two and six specific changes at key locations along the amino acid chain that occur over many generations (Broadwater et al., (2002) J Biol Chem 277, 15613-15620; Cahoon et al., (1997) Proc Natl Acad Sci USA 94, 4872-4877). In order to accumulate mutations at these key sites, many additional mutations also accumulate, which tend to degrade attributes such as stability and turnover of the enzyme (Taverna and Goldstein, (2002) Proteins 46, 105-109). In contrast, insertion or deletion of a transit peptide is a single-step process that is potentially instantaneous and does not necessarily result in a degradation of function. The present invention is not limited to a particular mechanism (indeed, an understanding of the mechanism is not necessary to practice the present invention). Nonetheless, it is contemplated that the Δ$^7$ desaturase, FAD5 (ADS3), evolved from an ancestral Δ$^9$ desaturase by the addition of a transit peptide, because FAD5 (ADS3) retained Δ$^9$ regiospecificity and product accumulation increased by ~50% with the removal of the transit peptide. The observation that FAD5 is active in both compartments is unlikely because the environments of the plastidial and cytoplasmic membranes differ markedly in factors including lipid composition, presence of different electron donors (cytochrome $b_5$ in the ER, ferredoxin in the plastid), redox state, and pH. Several lines of evidence support the view that FAD5 evolved from a cytoplasmic ADS enzyme: the widespread occurrence of Δ$^9$-unsaturated fatty acids in nature compared to Δ$^7$-fatty acids; the occurrence of a single gene in *Arabidopsis* containing the transit peptide versus eight genes lacking one; and that the closest homologs of the ADS enzymes are cyanobacterial desaturases that lack transit peptides. One possible explanation for the efficient functioning of Fad5 in the plastid is that ferredoxin is more electronegative than cytochrome $b_5$, and being a stronger electron donor might overcome less than optimal protein-protein interaction. However, when a cyanobacterial Δ$^6$-desaturase from *Synechocystis* was expressed in plants, it was found to be equally active when targeted to the plastid, endoplasmic reticulum or cytoplasm providing a case in which a ferredoxin dependent enzyme is presumably functional with endoplasmic reticulum electron donors such as cytochrome $b_5$ (Reddy and Thomas, (1996) Nat Biotechnol 14, 639-642). The experimental evidence therefore suggests that for both ADS enzymes and cyanobacterial desaturases, partnering with native electron donors is not essential for function. While the FAD5 desaturase evidently arose by addition of a plastidial targeting sequence to a member of the multigene ADS family, targeting to different compartments can also occur by alternate mRNA splicing of individual genes (Duchene et al., (2001) J Biol Chem 276, 15275-15283. Epub 2001 Feb. 2.).

Functional diversity of enzymes is commonly probed by feeding a spectrum of potential substrates. Such studies on a fatty acid conjugase/desaturase led Dyer and colleagues to hypothesize that multifunctional enzymes could potentially generate different products if expressed in different metabolic contexts (Dyer et al., (2002) Plant Physiol 130, 2027-2038). The results described herein are the first examples of a natural system in which enzymes evolved distinct regiospecificities by alternate subcellular targeting via interaction with different substrates. The experimental observation that switching of regiospecificity resulted from the redirection of a plastidial desaturase to the cytoplasm and of cytoplasmic desaturases to the plastid, respectively, prompted an investigation of whether switching of regiospecificity occurs in other protein classes. For changes in enzyme specificity by alternative targeting to occur, several criteria have to be met. First, individual members of protein families need to be targeted to different locations. A bioinformatics analysis of the *Arabidopsis* genome was performed and 239 encoded protein families with >50% amino acid identity that contain two or more members predicted to localize to different compartments by three independent algorithms were found. Using these very stringent criteria for inclusion it is clear that alternative targeting of members of protein families is a widespread phenomenon in *Arabidopsis*. Second, enzymes need to be capable of accepting two or more alternate substrates for catalysis. A survey of plant lipid modifying enzymes alone yields many examples of bifunctional enzymes, including desaturases, hydroxylases and conjugases (Cahoon et al., (1997) Proc Natl Acad Sci USA 94, 4872-4877; Dyer et al., (2002) Plant Physiol 130, 2027-2038; van de Loo et al., (1995) Proc Natl Acad Sci USA 92, 6743-6747; Broun et al., (1998) Science 282, 1315-1317; Broun et al., (1998) Plant J 13, 201-210; Behrouzian et al., (2002) J Am Chem Soc 124, 3277-3283), suggesting that plants contain many bi- or multifunctional enzymes. Third, compartments contain specific complements of metabolites, a condition that has been experimentally observed for many decades. Members of numerous *Arabidopsis* protein families are exposed to different substrates in alternative subcellular locations, where they may perform different functions. Among the protein families identified as having members in several locations are protein kinases, cytochrome P450s, dehydrogenase/reductases, glycosyl transferases and lipases, enzymes that can be readily envisaged to exhibit modified functionality in alternate subcellular locations as described in the present work for the ADS enzymes.

Spatial or temporal co-localization of enzymes with pools of distinct substrates, as exemplified by the ADS enzymes, circumvents the barriers between eukaryotic subcellular compartments that separate specific sets of metabolites and enzymes and increases the product diversity resulting from a specific set of enzymes.

II. ADS Polypeptides

The present invention provides compositions comprising purified ADS polypeptides as well as compositions comprising variants of ADS, including truncated proteins, proteins with and without subcellular transit peptides, homologs, mutants, fragments, and fusion proteins thereof (as described further below).

In some embodiments of the present invention, the polypeptide is a purified product, obtained from expression of a native gene in a cell, while in other embodiments it may be a product of chemical synthetic procedures, and in still other embodiments it may be produced by recombinant techniques using a prokaryotic or eukaryotic host (e.g., by bacterial, yeast, higher plant, insect and mammalian cells in culture). In some embodiments, depending upon the host employed in a recombinant production procedure, the polypeptide of the present invention may be glycosylated or may be non-glycosylated. In other embodiments, the polypeptides of the invention may also include an initial methionine amino acid residue.

A. Reaction Catalyzed

An ADS is a fatty acid desaturase with the surprising ability to desaturate saturated fatty acids (e.g., 14, 16 and 18 carbons in length) at either the delta-9 or the delta-7 position.

Thus, an ADS polypeptide catalyzes desaturation of a saturated fatty acid at either the $9^{th}$ carbon or, surprisingly, from the $7^{th}$ carbon atom in the hydrocarbon chain, when counting from the carboxyl end, as exemplified by the following reactions:

1. Saturated fatty acid+electron donor$_{reduced}$+$O_2$→delta-9 desaturated fatty acid+electron donor$_{oxidised}$+$H_2O$
2. Saturated fatty acid+electron donor$_{reduced}$+$O_2$→delta-7 desaturated fatty acid+electron donor$_{reduced}$+$H_2O$ Thus, products of an ADS include 16:1 delta-7, 16:1 delta-9 (palmitoleic acid) from C16:0 (palmitic acid), and C18:1 delta-9 (oleic acid) from C18:0 (stearic acid). It is contemplated that the enzyme in situ most likely acts on a fatty acid substrate that is esterified to a glycerol backbone, such as a glycolipid or a phospholipid. However, the enzyme may utilize different substrates under different conditions to differing degrees of activity, and may produce other products as well. Although it is not necessary to understand the underlying mechanism to practice the invention, and the invention is not limited to any particular mechanism, it is contemplated that Reaction 1 is catalyzed in an extraplastidial location by ADS expressed without a transit peptide initially, where the electron donor is cytochrome $b_5$. It is also contemplated that Reaction 2 is catalyzed in a plastidial location by an ADS expressed with a transit peptide initially, where the electron donor is ferredoxin.

Other products of the desaturase include downstream elongation products, such as the elongation of C16:1 delta-7 (palmitoleic acid) to C18:1 delta-11 (vaccenic acid).

It is contemplated that the presence of a plastid transit peptide in an ADS polypeptide increases the proportion of delta-7 desaturated fatty acid products, while the absence of a plastid transit peptide increases the proportions of delta-9 desaturated fatty acid products. It is further contemplated that when present in different lipid environments, an ADS utilizes different fatty acid substrates or exhibits different fatty acid substrate specificities. It is also contemplated that when present in different lipid environments, an ADS utilizes different glycerolipid substrates, for example, galactolipids and/or phospholipids in a plastid, and phospholipids or to lesser extent galactolipids in the ER.

B. ADS Polypeptides

In some embodiments, the polypeptide comprises an ADS polypeptide. In different embodiments, an ADS of the present invention is encoded by a sequence shown in FIGS. 4-7 (SEQ ID Nos 1, 3, 5, and 7); in other embodiments, an ADS polypeptide comprises an amino acid sequence shown in FIGS. 4-7 (SEQ ID Nos:2, 4, 6, and 8).

C. Variant ADS Polypeptides

In other embodiments, the present invention provides isolated variants of the disclosed ADS polypeptides; these variants include mutants, fragments, fusion proteins or functional equivalents of ADS. Exemplary variants are described further below.

D. Assay of ADS Polypeptides

The activity of ADS may be assayed in a number of ways. These include, but are not limited to, in vivo assays and in vitro assays, as described further below.

In some embodiments, enzyme activity is determined in vivo by expressing a nucleic acid sequence encoding an ADS in a transgenic organism and then analyzing the content and composition of the fatty acid fraction present in the transgenic organism. Thus, the activity is measured as the presence of or increase in the amount of endogenous monounsaturated fatty acid, and in particular of C16:1 delta-9, its elongation product 18:1 delta-11 (vaccenic acid), and 18:1 delta-9, in a transgenic organism which comprises an exogenous nucleic acid sequence having a coding sequence of the present invention; such transgenic organisms are obtained as described below. The amount of the products of ADS in a transgenic organism is compared to that present in a non-transgenic organism. The fatty acids products are typically analyzed either from fatty acids extracted and methylated from samples of a transgenic organism, or from lipids extracted from samples of a transgenic organism, as for example as is described in Example 1.

In other embodiments, enzyme activity is determined in vivo by adding exogenous substrates to tissue samples obtained from an organism which may or may not be transgenic (transgenic organisms are described below). For example, in plants, tissue samples include but are not limited to leaf samples (such as discs), stem and root samples, and developing and mature seed embryonic or endosperm tissue. Typically, tissue samples are incubated with [$^{14}$C]fatty acid substrate, such as 16:0, which can be taken up and incorporated into tissue lipids. Incubations generally proceed at room temperature in a buffered solution for a suitable period of time. The samples are then washed in buffer, and the tissue sample fatty acids analyzed as described above. Alternatively, enzyme activity is determined in vivo by adding exogenous substrates to a transgenic microorganism, such as yeast or bacteria.

In yet other embodiments, enzyme activity is determined in vitro in a cell-free homogenate or subcellular fraction obtained from an organism which may or may not be transgenic (transgenic organisms are described below), where the tissue is disrupted and filtered or centrifuged to result in cell-free fractions. For example, in plants, subcellular fractions may be obtained from any of the types of tissues described above, and include whole cell and microsomal membranes, plastids and plastid membrane fractions, or other isolated and purified organelles and membranes such as mitochondria and peroxisomes and plasmalemma. The preparation of such fractions is well-known in the art. The subcellular fraction is then incubated with a fatty acid substrate, typically as $^{14}$C-acyl-CoA, which can be taken up and incorporated into tissue lipids. Additional co-factors for lipid synthesis and desaturase, as required, may be present during the incubation; such co-factors include but are not limited to electron donors, such as cytochrome b5 or ferredoxin. Other reagents which may enhance lipid synthesis and/or desaturase may also be added; such reagents include phospholipid liposomes and lipid transfer proteins. The samples are incubated and the lipids extracted as described above.

In yet other embodiments, enzyme activity is determined from an in-vitro nucleic acid expression system, to which a nucleic acid sequence having a coding sequence of the present invention is added and the encoded enzyme expressed, and the activity of the expressed enzyme determined. Such expression systems are well-known in the art, and include, for example reticulocyte lysate or wheat germ. The enzyme may be stabilized by the presence of TAGs and/or other glycerolipids, by phosphoglycerolipids which produce membrane structures, or by mixtures of lipids and detergents which produce micellar structures; these structures may be included in the mixture and may include the substrate upon which the enzyme might act, and might include the product produced by the enzyme. The activity of newly-expressed enzyme is then analyzed as described above for subcellular fractions.

The extracted fatty acid products of ADS are analyzed by methods well-known in the art. For example, the extracted and methylated fatty acid by GC; double bond position can be analyzed by GC/MC following derivatization by agents such as DMDS.

E. Purification of ADS Polypeptides

In some embodiments of the present invention, an ADS polypeptide purified from organisms is provided; such organisms include transgenic organisms, comprising a heterologous ADS gene, as well as organisms in which ADS occurs naturally. In other embodiments, an ADS polypeptide is purified from an in vitro nucleic acid expression system, which comprises a nucleic acid sequence having a coding sequence of the present invention and from which the expressed ADS can be purified. The present invention provides a purified ADS polypeptide as well as variants, including homologs, mutants, fragments, and fusion proteins thereof (as described further below).

The present invention also provides methods for recovering and purifying plant ADS from an organism or from an in vitro nucleic acid expression system; exemplary organisms include single and multi-cellular organisms. When isolated from an organism, the cells are typically first disrupted and then fractionated before subsequent enzyme purification; disruption and fractionation methods are well-known.

Purification methods are also well-known, and include, but are not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography, and ioselectric focusing. It is contemplated that ADS purified in an active or inactive form may require the presence of detergents to maintain its solubility in aqueous media during fractionation. It is further contemplated that assay of the enzyme activity may require removal of the detergent and reconstitution in liposomes to recover full activity. Such methods are well known (for example see Hjelmeland and Chrambach, Furth et al., and van Renswoude and Kempf (1984) Methods in Enzymology 104, p 305, 318 and 329 respectively).

The present invention further provides nucleic acid sequences having a coding sequence of the present invention fused in frame to a marker sequence that allows for expression alone or both expression and purification of the polypeptide of the present invention. A non-limiting example of a marker sequence is a hexahistidine tag that may be supplied by a vector, for example, a pQE-30 vector which adds a hexahistidine tag to the N terminal of an ADS and which results in expression of the polypeptide in the case of a bacterial host, and in other embodiments by vector PT-23B, which adds a hexahistidine tag to the C terminal of an ADS and which results in improved ease of purification of the polypeptide fused to the marker in the case of a bacterial host, or, for example, the marker sequence may be a hemagglutinin (HA) tag when a mammalian host is used. The HA tag corresponds to an epitope derived from the influenza hemagglutinin protein (Wilson et al. (1984) Cell 37:767). Other examples are described below.

F. Chemical Synthesis of an ADS Polypeptide

In some embodiments of the present invention, an ADS protein is produced using chemical methods to synthesize either an entire ADS amino acid sequence or a portion thereof. For example, peptides are synthesized by solid phase techniques, cleaved from the resin, and purified by preparative high performance liquid chromatography (See e.g., Creighton (1983) *Proteins Structures And Molecular Principles*, W H Freeman and Co, New York N.Y.). In other embodiments of the present invention, the composition of the synthetic peptides is confirmed by amino acid analysis or sequencing (see, for example, Creighton, supra).

Direct peptide synthesis can be performed using various solid-phase techniques (Roberge et al. (1995) Science, 269: 202-204) and automated synthesis may be achieved, for example, using ABI 431A Peptide Synthesizer (Perkin Elmer) in accordance with the instructions provided by the manufacturer. Additionally, an amino acid sequence of an ADS, or any part thereof, may be altered during direct synthesis and/or combined using chemical methods with other sequences to produce a variant polypeptide.

G. Generation of ADS Antibodies

In some embodiments of the present invention, antibodies are generated to allow for the detection and characterization of an ADS protein. The antibodies may be prepared using various immunogens. In one embodiment, the immunogen is an ADS polypeptide or fragments thereof to generate antibodies that recognize ADS. Such antibodies include, but are not limited to polyclonal, monoclonal, chimeric, single chain, Fab fragments, and Fab expression libraries.

Various procedures known in the art may be used for the production of polyclonal antibodies directed against an ADS. For the production of antibody, various host animals can be immunized by injection with the peptide corresponding to an ADS epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels (e.g., aluminum hydroxide), surface active substances (e.g., lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*).

For preparation of monoclonal antibodies directed toward an ADS, it is contemplated that any technique that provides for the production of antibody molecules by continuous cell lines in culture finds use with the present invention (See e.g., Harlow and Lane, *Antibodies: A Laboratory Manual*, Cold Spring Harbor Laboratory Press, Cold Spring Harbor, N.Y.). These include but are not limited to the hybridoma technique originally developed by Köhler and Milstein (Köhler and Milstein (1975) Nature, 256:495-497), as well as the trioma technique, the human B-cell hybridoma technique (See e.g., Kozbor et al. (1983) Immunol. Tod., 4:72), and the EBV-hybridoma technique to produce human monoclonal antibodies (Cole et al. (1985) in *Monoclonal Antibodies and Cancer Therapy*, Alan R. Liss, Inc., pp. 77-96).

In addition, it is contemplated that techniques described for the production of single chain antibodies (U.S. Pat. No. 4,946,778) find use in producing an ADS-specific single chain antibodies. An additional embodiment of the invention utilizes the techniques described for the construction of Fab expression libraries (Huse et al. (1989) Science, 246:1275-1281) to allow rapid and easy identification of monoclonal Fab fragments with the desired specificity for an ADS.

It is contemplated that any technique suitable for producing antibody fragments finds use in generating antibody fragments that contain the idiotype (antigen binding region) of the antibody molecule. For example, such fragments include but are not limited to: F(ab')2 fragment that can be produced by pepsin digestion of the antibody molecule; Fab' fragments that can be generated by reducing the disulfide bridges of the F(ab')2 fragment, and Fab fragments that can be generated by treating the antibody molecule with papain and a reducing agent.

In the production of antibodies, it is contemplated that screening for the desired antibody is accomplished by techniques known in the art (e.g., radioimmunoassay, ELISA (enzyme-linked immunosorbant assay), "sandwich" immunoassays, immunoradiometric assays, gel diffusion precipitin reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention. As is well known in the art, the immunogenic peptide should be provided free of the carrier molecule used in any immunization protocol. For example, if the peptide was conjugated to KLH, it may be conjugated to BSA, or used directly, in a screening assay.

In some embodiments of the present invention, the foregoing antibodies are used in methods known in the art relating to the expression of an ADS (e.g., for Western blotting), measuring levels thereof in appropriate biological samples, etc. The antibodies can be used to detect ADS in a biological sample from a plant. The biological sample can be an extract of a tissue, or a sample fixed for microscopic examination.

The biological samples are then be tested directly for the presence of ADS using an appropriate strategy (e.g., ELISA or radioimmunoassay) and format (e.g., microwells, dipstick (e.g., as described in International Patent Publication WO 93/03367), etc. Alternatively, proteins in the sample can be size separated (e.g., by polyacrylamide gel electrophoresis (PAGE), in the presence or not of sodium dodecyl sulfate (SDS), and the presence of ADS detected by immunoblotting (Western blotting). Immunoblotting techniques are generally more effective with antibodies generated against a peptide corresponding to an epitope of a protein, and hence, are particularly suited to the present invention.

III. ADS Coding Sequences

The present invention provides compositions comprising purified nucleic acid sequences encoding any of the ADS described above or below. Coding sequences include but are not limited to genes, cDNA, and RNA.

Thus, the present invention provides compositions comprising purified nucleic acid sequences encoding an ADS, as well as nucleic acid sequences encoding variants of ADS, including homologs, mutants, or fragments, or fusion proteins thereof, as described above and below. In yet other embodiments, the nucleic acid sequences encode a portion of an ADS which retains some functional characteristic of an ADS. Examples of functional characteristics include the ability to act as an immunogen to produce an antibody which recognizes an ADS.

Coding sequences for ADS include sequences isolated from an organism, which either comprises the coding sequence naturally or is transgenic and comprises a heterologous ADS coding sequence, sequences which are chemically synthesized, as well as sequences which represent a combination of isolated and synthesized (as, for example, where isolated sequences are mutagenized, or where a sequence comprises parts of sequences isolated from different sources and/or synthesized from different sources).

Thus, in some embodiments of the invention, the coding sequence of a ADS is synthesized, whole or in part, using chemical methods well known in the art (See e.g., Caruthers et al. (1980) Nucl. Acids Res. Symp. Ser. 7:215-233; Crea and Horn (1980) Nucl. Acids Res. 9:2331; Matteucci and Caruthers (1980) Tetrahedron Lett. 21:719; and Chow and Kempe (1981) Nucl. Acids Res. 9:2807-2817

A. ADS Coding Sequence

In some embodiments, the sequences encode an ADS; in other embodiments, the sequences encode ADS1, ADS2, ADS3, or ADS(72-731). In some embodiments, the sequences comprise a sequence shown in FIGS. 4-7 (SEQ ID NO:1, 2, 3, or 4); in other embodiments, the sequences encode an amino acid sequence shown in FIGS. 4-7 (SEQ ID Nos:2, 4, 6, and 8).

B. Variant ADS Coding Sequences: Transit Peptides

In other embodiments, the sequences encode a variant of the disclosed ADS polypeptides; these variants include mutants, fragments, fusion proteins or functional equivalents of ADS. In preferred embodiments, variants comprise ADS polypeptides to which non-naturally occurring transit peptides are added, or from which naturally occurring transit peptides are removed, as described in more detail below. Exemplary sequences encoding other variants are also described further below.

IV. Variants of ADS

In some embodiments, the present invention provides isolated variants of the disclosed nucleic acid sequence encoding ADS, and the polypeptides encoded thereby; these variants include mutants, fragments, fusion proteins, or functional equivalents of ADS. Thus, nucleotide sequences of the present invention are engineered in order to alter an ADS coding sequence for a variety of reasons, including but not limited to alterations that modify the cloning, processing and/or expression of the gene product (such alterations include inserting new restriction sites, altering glycosylation patterns, and changing codon preference) as well as varying the enzymatic activity (such changes include but are not limited to differing substrate affinities, differing substrate preferences and utilization, differing inhibitor affinities or effectiveness, differing reaction kinetics, varying subcellular localization, and varying protein processing and/or stability). For example, mutations are introduced which alter the substrate specificity, such that the preferred substrate is changed.

In other embodiments, the present invention provides isolated nucleic acid sequences encoding an ADS, where the encoded desaturase competes for binding to an unsaturated fatty acid substrate with a protein comprising an amino acid sequence of SEQ ID NOs:2, 4, 6, or 8.

A. Transit Peptides

As described above, ADS3 differs from ADS1 and ADS2 in the presence of a plastid transit peptide. This transit peptide comprises about amino acids 1-71 of SEQ ID NO:6. ADS(72-371) lacks a transit peptide, and is in this respect similar to ADS1 and ADS2. The presence of a transit peptide appears to confer an ability of increased synthesis of C16:1 delta-7 when the enzymes are expressed in vivo in transgenic plants.

Thus, in some embodiments, the present invention provides an ADS polypeptide without a transit peptide (exemplary ADS polypeptides include ADS1, ADS2 ADS(72-371). In ADS polypeptides with naturally occurring peptides, the peptide is removed by a number of techniques. In some techniques, the nucleic acid sequence coding for a transit peptide is removed from the coding sequence for the remainder of the ADS polypeptide, and the coding sequence for the ADS polypeptide minus the coding sequence for the transit peptide placed under control of a promoter (as, for example, is described in the Examples).

In other embodiments, the present invention provides an ADS with a transit peptide. In some embodiments, the transit peptide occurs naturally in ADS (as for example ADS3, where the transit peptide comprises amino acids 1-72 of SEQ ID NO:6). In other embodiments, the transit peptide is added to an ADS which does not comprise a naturally occurring transit peptide.

Transit peptides are well known in the art, and direct proteins to locations such as the chloroplast, the mitochondria, the endoplasmic reticulum, the tonoplast, the golgi network, and the plasmalemma.

Thus, in some embodiments, the transit peptide is a plastid peptide. In some further embodiments, the transit peptide occurs naturally in ADS (as for example ADS3, where the transit peptide comprises amino acids 1-72 of SEQ ID NO:6). In other further embodiments, the transit peptide is added to an ADS which lacks a naturally occurring plastid transit peptide. In particular embodiments, the transit peptide of ADS3 is added to ADS1 or ADS2, creating fusion proteins. In other embodiments, the transit peptide is a mitochondrial peptide. In yet other embodiments, the transit peptide targets the endoplasmic reticulum, the tonoplast, the golgi, or the plasmalemma. Transit peptides can be added to an ADS polypeptide as is described below for fusion proteins.

B. Mutants and Homologs of ADS

Some embodiments of the present invention provide mutant forms of ADS (i.e., muteins). In preferred embodiments, variants result from mutation, (i.e., a change in the nucleic acid sequence) and generally produce altered mRNAs or polypeptides whose structure or function may or may not be altered. Any given gene may have none, one, or many mutant forms. Common mutational changes that give rise to variants are generally ascribed to deletions, additions or substitutions of nucleic acids. Each of these types of changes may occur alone, or in combination with the others, and at the rate of one or more times in a given sequence.

Still other embodiments of the present invention provide an isolated nucleic acid sequence encoding ADS homologs, and the polypeptides encoded thereby.

It is contemplated that is possible to modify the structure of a peptide having an activity (for example, for delta-7 or delta-9 desaturase activity) for such purposes as increasing synthetic activity or altering the affinity of the ADS for a substrate, or for increasing stability or turnover or subcellular location of the polypeptide. Such modified peptides are considered functional equivalents of peptides having an activity of an ADS as defined herein. A modified peptide can be produced in which the nucleotide sequence encoding the polypeptide has been altered, such as by substitution, deletion, or addition.

In some preferred embodiments of the present invention, the alteration modifies the amount of a particular mono-unsaturated fatty acid produced. Exemplary alterations include the presence or absence of a plastid transit peptide, as described above. In other embodiments, modifications do not significantly reduce the synthetic activity of the modified enzyme. In other words, construct "X" can be evaluated in order to determine whether it is a member of the genus of modified or variant ADS of the present invention as defined functionally, rather than structurally. In preferred embodiments, the activity of variant ADS is evaluated by the methods described in the Examples. Accordingly, in some embodiments the present invention provides nucleic acids encoding an ADS that complement the coding region of SEQ ID NOs: 1, 3, 5, or 7. In other embodiments, the present invention provides nucleic acids encoding an ADS that compete for the binding of a fatty acid substrate with the protein encoded by SEQ ID NOs: 1, 3, 5, or 7, or comprising SEQ ID NOs: 2, 4, 6, or 8.

In other preferred embodiments of the alteration, the alteration results in intracellular half-lives dramatically different from that of the corresponding wild-type protein. For example, an altered protein is rendered either more stable or less stable to proteolytic degradation or other cellular process that result in destruction of, or otherwise inactivate ADS. Such homologs, and the genes that encode them, can be utilized to alter the activity of ADS by modulating the half-life of the protein. For instance, a short half-life can give rise to more transient ADS biological effects. Other variants have characteristics which are either similar to wild-type ADS, or which differ in one or more respects from wild-type ADS.

As described above, mutant forms of an ADS are also contemplated as being equivalent to those peptides and DNA molecules that are set forth in more detail herein. For example, it is contemplated that isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide variants of an ADS disclosed herein containing conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (e.g., Stryer ed. (1981) *Biochemistry*, pg. 17-21, 2nd ed, WH Freeman and Co.). Whether a change in the amino acid sequence of a peptide results in a functional homolog can be readily determined by assessing the ability of the variant peptide to function in a fashion similar to the wild-type protein. Peptides having more than one replacement can readily be tested in the same manner.

More rarely, a variant includes "nonconservative" changes (e.g., replacement of a glycine with a tryptophan). Analogous minor variations can also include amino acid deletions or insertions, or both. Guidance in determining which amino acid residues can be substituted, inserted, or deleted without abolishing biological activity can be found using computer programs (e.g., LASERGENE software, DNASTAR Inc., Madison, Wis.).

Mutants of an ADS can be generated by any suitable method well known in the art, including but not limited to site-directed mutagenesis, randomized "point" mutagenesis, and domain-swap mutagenesis in which portions of one ADS cDNA are "swapped" with the analogous portion of another ADS cDNA (Back and Chappell (1996) PNAS 93: 6841-6845).

Variants may be produced by methods such as directed evolution or other techniques for producing combinatorial libraries of variants. Thus, the present invention further contemplates a method of generating sets of combinatorial mutants of the present ADS proteins, as well as truncation mutants, and is especially useful for identifying potential variant sequences (in other words, homologs) that possess the biological activity of an ADS of the present invention. In addition, screening such combinatorial libraries is used to generate, for example, novel ADS homologs that possess novel substrate specificities or other biological activities all together; examples of substrate specificities are described above.

It is contemplated that the ADS nucleic acids as described above and below can be utilized as starting nucleic acids for directed evolution. These techniques can be utilized to develop ADS variants having desirable properties such as increased synthetic activity or altered product ratios.

In some embodiments, artificial evolution is performed by random mutagenesis (e.g., by utilizing error-prone PCR to introduce random mutations into a given coding sequence). This method requires that the frequency of mutation be finely tuned. As a general rule, beneficial mutations are rare, while deleterious mutations are common. This is because the combination of a deleterious mutation and a beneficial mutation often results in an inactive enzyme. The ideal number of base substitutions for targeted gene is usually between 1.5 and 5 (Moore and Arnold (1996) Nat. Biotech., 14, 458-67; Leung et al. (1989) Technique, 1:11-15; Eckert and Kunkel (1991) PCR Methods Appl., 1:17-24; Caldwell and Joyce (1992) PCR Methods Appl., 2:28-33; and Zhao and Arnold (1997) Nuc. Acids. Res., 25:1307-08). After mutagenesis, the resulting clones are selected for desirable activity. Successive rounds of mutagenesis and selection are often necessary to develop enzymes with desirable properties. It should be noted that only the useful mutations are carried over to the next round of mutagenesis.

In other embodiments of the present invention, the polynucleotides of the present invention are used in gene shuffling or sexual PCR procedures (e.g., Smith (1994) Nature, 370: 324-25; U.S. Pat. Nos. 5,837,458; 5,830,721; 5,811,238; 5,733,731). Gene shuffling involves random fragmentation of several mutant DNAs followed by their reassembly by PCR into full length molecules. Examples of various gene shuffling procedures include, but are not limited to, assembly following DNase treatment, the staggered extension process (STEP), and random priming in vitro recombination. In the DNase mediated method, DNA segments isolated from a pool of positive mutants are cleaved into random fragments with DNaseI and subjected to multiple rounds of PCR with no added primer. The lengths of random fragments approach that of the uncleaved segment as the PCR cycles proceed, resulting in mutations in present in different clones becoming mixed and accumulating in some of the resulting sequences. Multiple cycles of selection and shuffling have led to the functional enhancement of several enzymes (Stemmer (1994) Nature, 370:398-91; Stemmer (1994) Proc. Natl. Acad. Sci. USA, 91, 10747-10751; Crameri et al. (1996) Nat. Biotech., 14:315-319; Zhang et al. (1997) Proc. Natl. Acad. Sci. USA, 94:4504-09; and Crameri et al. (1997) Nat. Biotech., 15:436-38). Variants produced by directed evolution can be screened for ADS activity by the methods described below and in the Examples.

In some embodiments of a combinatorial mutagenesis approach of the present invention, the amino acid sequences of a population of ADS coding sequences are aligned, preferably to promote the highest homology possible. Such a population of variants can include, for example, ADS homologs from one or more species, or ADS homologs from the same species but which differ due to mutation. Amino acids that appear at each position of the aligned sequences are selected to create a degenerate set of combinatorial sequences.

In preferred embodiments of the present invention, the combinatorial ADS library is produced by way of a degenerate library of genes encoding a library of polypeptides that each include at least a portion of candidate ADS-protein sequences. For example, a mixture of synthetic oligonucleotides is enzymatically ligated into gene sequences such that the degenerate set of candidate ADS sequences are expressible as individual polypeptides, or alternatively, as a set of larger fusion proteins (e.g., for phage display) containing the set of ADS sequences therein.

There are many ways by which the library of potential ADS homologs can be generated from a degenerate oligonucleotide sequence. In some embodiments, chemical synthesis of a degenerate gene sequence is carried out in an automatic DNA synthesizer, and the synthetic genes are ligated into an appropriate gene for expression. The purpose of a degenerate set of genes is to provide, in one mixture, all of the sequences encoding the desired set of potential ADS sequences. The synthesis of degenerate oligonucleotides is well known in the art (See e.g., Narang (1983) Tetrahedron Lett., 39:3-9; Itakura et al. (1981) Recombinant DNA, in Walton (ed.), Proceedings of the 3rd Cleveland Symposium on Macromolecules, Elsevier, Amsterdam, pp 273-289; Itakura et al. (1984) Annu. Rev. Biochem., 53:323; Itakura et al. (1984) Science 198: 1056; Ike et al. (1983) Nucl. Acid Res., 11:477). Such techniques have been employed in the directed evolution of other proteins (See e.g., Scott et al. (1980) Science, 249:386-390; Roberts et al. (1992) Proc. Natl. Acad. Sci. USA, 89:2429-2433; Devlin et al. (1990) Science, 249: 404-406; Cwirla et al. (1990) Proc. Natl. Acad. Sci. USA, 87: 6378-6382; as well as U.S. Pat. Nos. 5,223,409, 5,198,346, and 5,096,815).

C. Truncation Mutants of ADS Polypeptides

In addition, the present invention provides isolated nucleic acid sequences encoding fragments of ADS (in other words, truncation mutants), and the polypeptides encoded by such nucleic acid sequences. In preferred embodiments, the ADS fragment is biologically active.

In some embodiments, a truncation mutant is a mutant in which a naturally occurring transit peptide is removed (for example, ADS(72-371).

In some embodiments of the present invention, when expression of a portion of an ADS protein is desired, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from E. coli (Ben-Bassat et al. (1987) J. Bacteriol., 169:751-757) and Salmonella typhimurium and its in vitro activity has been demonstrated on recombinant proteins (Miller et al. (1990) Proc. Natl. Acad. Sci. USA, 84:2718-1722). Therefore, removal of an N-terminal methionine, if desired, can be achieved either in vivo by expressing such recombinant polypeptides in a host that produces MAP (e.g., E. coli or CM89 or S. cerevisiae), or in vitro by use of purified MAP.

D. Fusion Proteins Containing ADS Polypeptides

The present invention also provides nucleic acid sequences encoding fusion proteins incorporating all or part of ADS, and the polypeptides encoded by such nucleic acid sequences.

In some embodiments, a fusion protein comprises an ADS which does not possess a naturally occurring transit peptide fused to a transit peptide, as described above. In these embodiments of the present invention, chimeric constructs code for fusion proteins containing an ADS gene or portion thereof and a leader or other signal sequences that direct the protein to targeted subcellular locations. Such sequences are well known in the art, and direct proteins to locations such as the chloroplast, the mitochondria, the endoplasmic reticulum, the tonoplast, the golgi network, and the plasmalemma.

In other embodiments, the fusion proteins have an ADS functional domain with a fusion partner. Accordingly, in some embodiments of the present invention, the coding sequences for the polypeptide (for example, an ADS functional domain) is incorporated as a part of a fusion gene including a nucleotide sequence encoding a different polypeptide. In one embodiment, a single fusion product polypeptide has ADS activity.

In some embodiments of the present invention, chimeric constructs code for fusion proteins containing a portion of an ADS and a portion of another gene. In some embodiments, the fusion proteins have biological activity similar to the wild type ADS (for example have at least one desired biological activity of ADS). In other embodiments, the fusion proteins have altered biological activity.

In addition to utilizing fusion proteins to alter biological activity, it is widely appreciated that fusion proteins can also facilitate the expression and/or purification of proteins, such as an ADS protein of the present invention. Accordingly, in some embodiments of the present invention, an ADS is generated as a glutathione-S-transferase (i.e., GST fusion protein). It is contemplated that such GST fusion proteins enables easy purification of an ADS, such as by the use of glutathione-derivatized matrices (See e.g., Ausabel et al. (eds.) (1991) Current Protocols in Molecular Biology, John Wiley & Sons, NY).

In another embodiment of the present invention, a fusion gene coding for a purification leader sequence, such as a poly-(His)/enterokinase cleavage site sequence at the N-terminus of the desired portion of an ADS allows purification of the expressed ADS fusion protein by affinity chromatography using a $Ni^{2+}$ metal resin. In still another embodiment of the present invention, the purification leader sequence is then subsequently removed by treatment with enterokinase (See e.g., Hochuli et al. (1987) J. Chromatogr., 411:177; and Janknecht et al Proc. Natl. Acad. Sci. USA, 88:8972). In yet other embodiments of the present invention, a fusion gene coding for a purification sequence appended to either the N (amino)

or the C (carboxy) terminus allows for affinity purification; one example is addition of a hexahistidine tag to the carboxy terminus of an ADS, which is contemplated to be useful for affinity purification.

Techniques for making fusion genes are well known. Essentially, the joining of various nucleic acid fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment of the present invention, the fusion gene can be synthesized by conventional techniques including automated DNA synthesizers. Alternatively, in other embodiments of the present invention, PCR amplification of gene fragments is carried out using anchor primers that give rise to complementary overhangs between two consecutive gene fragments that can subsequently be annealed to generate a chimeric gene sequence (See e.g., Current Protocols in Molecular Biology, supra). In yet other embodiments of the present invention, epitope tags of ADS are prepared.

V. Expression of Cloned ADS

In other embodiment of the present invention, nucleic acid sequences corresponding to the ADS genes, homologs and mutants as described above may be used to generate recombinant DNA molecules that direct the expression of the encoded protein product in appropriate host cells.

As will be understood by those of skill in the art, it may be advantageous to produce ADS-encoding nucleotide sequences possessing non-naturally occurring codons. Therefore, in some preferred embodiments, codons preferred by a particular prokaryotic or eukaryotic host (Murray et al. (1989) Nucl. Acids Res., 17) can be selected, for example, to increase the rate of ADS expression or to produce recombinant RNA transcripts having desirable properties, such as a longer half-life, than transcripts produced from naturally occurring sequence.

A. Vectors for Production of ADS

The nucleic acid sequences of the present invention may be employed for producing polypeptides by recombinant techniques. Thus, for example, the nucleic acid sequence may be included in any one of a variety of expression vectors for expressing a polypeptide. In some embodiments of the present invention, vectors include, but are not limited to, chromosomal, nonchromosomal and synthetic DNA sequences (e.g., derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host.

In particular, some embodiments of the present invention provide recombinant constructs comprising one or more of the nucleic sequences as broadly described above (for example, SEQ ID NOs: 1, 3, 5 or 7) or encoding one or more of the amino acid sequences as broadly described above (SEQ ID NOs:2, 4, 6, or 8). In some embodiments of the present invention, the constructs comprise a vector, such as a plasmid or viral vector, into which a nucleic acid sequence of the invention has been inserted, in a forward or reverse orientation. In preferred embodiments of the present invention, the appropriate nucleic acid sequence is inserted into the vector using any of a variety of procedures. In general, the nucleic acid sequence is inserted into an appropriate restriction endonuclease site(s) by procedures known in the art.

Large numbers of suitable vectors are known to those of skill in the art, and are commercially available. Such vectors include, but are not limited to, the following vectors: 1) Bacterial—pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia); and 2) Eukaryotic—pWLNEO, pSV2CAT, pOG44, PXT1, pSG (Stratagene) pSVK3, pBPV, pMSG, and pSVL (Pharmacia). Any other plasmid or vector may be used as long as they are replicable and viable in the host. In some preferred embodiments of the present invention, plant expression vectors comprise an origin of replication, a suitable promoter and enhancer, and also any necessary ribosome binding sites, polyadenylation sites, splice donor and acceptor sites, transcriptional termination sequences, and 5' flanking nontranscribed sequences. In other embodiments, DNA sequences derived from the SV40 splice, and polyadenylation sites may be used to provide the required nontranscribed genetic elements.

In certain embodiments of the present invention, a nucleic acid sequence of the present invention within an expression vector is operatively linked to an appropriate expression control sequence(s) (promoter) to direct mRNA synthesis. Promoters useful in the present invention include, but are not limited to, the LTR or SV40 promoter, the $E.\ coli$ lac or trp, the phage lambda $P_L$ and $P_R$, T3 and T7 promoters, and the cytomegalovirus (CMV) immediate early, herpes simplex virus (HSV) thymidine kinase, and mouse metallothionein-I promoters and other promoters known to control expression of gene in prokaryotic or eukaryotic cells or their viruses. In other embodiments of the present invention, recombinant expression vectors include origins of replication and selectable markers permitting transformation of the host cell (e.g., dihydrofolate reductase or neomycin resistance for eukaryotic cell culture, or tetracycline or ampicillin resistance in $E.\ coli$).

In some embodiments of the present invention, transcription of the DNA encoding polypeptides of the present invention by higher eukaryotes is increased by inserting an enhancer sequence into the vector. Enhancers are cis-acting elements of DNA, usually about from 10 to 300 bp that act on a promoter to increase its transcription. Enhancers useful in the present invention include, but are not limited to, the SV40 enhancer on the late side of the replication origin bp 100 to 270, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present invention, the vector may also include appropriate sequences for amplifying expression.

B. Host Cells for Production of ADS

In a further embodiment, the present invention provides host cells containing any of the above-described constructs. In some embodiments of the present invention, the host cell is a higher eukaryotic cell (e.g., a plant cell). In other embodiments of the present invention, the host cell is a lower eukaryotic cell (e.g., a yeast cell). In still other embodiments of the present invention, the host cell can be a prokaryotic cell (e.g., a bacterial cell). Specific examples of host cells include, but are not limited to, *Escherichia coli, Salmonella typhimurium, Bacillus subtilis*, and various species within the genera *Pseudomonas, Streptomyces*, and *Staphylococcus*, as well as *Saccharomycees cerivisiae, Schizosaccharomycees pombe,*

Drosophila S2 cells, Spodoptera Sf9 cells, Chinese hamster ovary (CHO) cells, COS-7 lines of monkey kidney fibroblasts, (Gluzman (1981) Cell 23:175), 293T, C127, 3T3, HeLa and BHK cell lines, NT-1 (tobacco cell culture line), root cell and cultured roots in rhizosecretion (Gleba et al. (1999) Proc Natl Acad Sci USA 96: 5973-5977). Other examples include microspore-derived cultures of oilseed rape (Weselake R J and Taylor D C (1999) Prog. Lipid Res. 38: 401), and transformation of pollen and microspore culture systems. Further examples are described in the Examples.

The constructs in host cells can be used in a conventional manner to produce the gene product encoded by any of the recombinant sequences of the present invention described above. In some embodiments, introduction of the construct into the host cell can be accomplished by calcium phosphate transfection, DEAE-Dextran mediated transfection, or electroporation (See e.g., Davis et al. (1986) Basic Methods in Molecular Biology). Alternatively, in some embodiments of the present invention, a polypeptide of the invention can be synthetically produced by conventional peptide synthesizers.

Proteins can be expressed in eukaryotic cells, yeast, bacteria, or other cells under the control of appropriate promoters. Cell-free translation systems can also be employed to produce such proteins using RNAs derived from a DNA construct of the present invention. Appropriate cloning and expression vectors for use with prokaryotic and eukaryotic hosts are described by Sambrook, et al. (1989) *Molecular Cloning: A Laboratory Manual*, Second Edition, Cold Spring Harbor, N.Y.

In some embodiments of the present invention, following transformation of a suitable host strain and growth of the host strain to an appropriate cell density, the selected promoter is induced by appropriate means (e.g., temperature shift or chemical induction) and cells are cultured for an additional period. In other embodiments of the present invention, cells are typically harvested by centrifugation, disrupted by physical or chemical means, and the resulting crude extract retained for further purification. In still other embodiments of the present invention, microbial cells employed in expression of proteins can be disrupted by any convenient method, including freeze-thaw cycling, sonication, mechanical disruption, or use of cell lysing agents.

VI. Manipulation of ADS Activity and Fatty Acid Composition in Cells

It is contemplated that the nucleic acids encoding an ADS of the present invention may be utilized to either increase or decrease the level of ADS mRNA and/or protein in transfected cells as compared to the levels in wild-type cells. It is further contemplated that changes in the level of ADS results in changes in the content, amount, proportion, or composition of saturated to unsaturated fatty acid content in a cell.

For example, C16:0 C18:0 are considered undesirable fatty acids in food oils, as they are saturated fatty acids, and saturated fatty acids are associated with undesirable health effects. Thus, in particular embodiments, expression or overexpression of ADS in transgenic plant seeds results in a decrease in the content, amount, proportion, or composition of C16:0 and/or C18:0, with a concomitant increase in monounsaturated fatty acids and/or polyunsaturated fatty acids, which would be downstream products of the monounsaturated fatty acids produced by overexpression of ADS.

Moreover, C16:1 delta-9 (palmitoleic acid), and it's elongation product C18:1 delta-11 (vaccenic acid), are useful in the chemical industry as industrial feed stocks. Thus, in particular embodiments, expression or overexpression of ADS in transgenic plant seeds results in an increase in the content, amount, proportion, or composition of C16:1 delta-9 (palmitoleic acid), and it's elongation product C18:1 delta-11 (vaccenic acid).

Illustrative examples of transgenic organisms are described below and provided in the Examples.

A. Increasing ADS Activity in Cells

In some embodiments of the present invention, saturated fatty acids are decreased, and/or unsaturated fatty acids are increased, by providing an organism transformed with a heterologous gene encoding an ADS of the present invention and growing the transgenic organism under conditions sufficient to modify the fatty acid composition. In other embodiments of the present invention, saturated fatty acids are decreased, and/or unsaturated fatty acids are increased, by transforming an organism with a heterologous gene encoding an ADS of the present invention and growing the transgenic organism under conditions sufficient to modify the fatty acid composition.

Organisms which are transformed with a heterologous gene encoding an ADS of the present invention include preferably those which naturally synthesize and store in some manner triacylglycerols (TAGs), and those which are commercially feasible to grow and suitable for harvesting large amounts of the TAG products. Such organisms include but are not limited to, oleaginous yeast and algae, and plants and animals. Examples of yeasts include oleaginous yeast, which include but are not limited to the genera *Lipomyces, Candida, Rhodotorula, Rhodosporidium* and *Cryptococcus*, which can be grown in commercial-scale fermenters. Examples of plants include preferably oil-producing plants, such as soybean, rapeseed and canola, sunflower, cotton, corn, cocoa, safflower, oil palm, coconut palm, flax, castor, and peanut. Many commercial cultivars can be transformed with heterologous genes. In cases where that is not possible, non-commercial cultivars of plants can be transformed, and the trait for expression of ADS of the present invention moved to commercial cultivars by breeding techniques well-known in the art.

A heterologous gene encoding an ADS of the present invention, which includes variants of an ADS, includes any suitable sequence of the invention which encodes an ADS as described above. Preferably, the heterologous gene is provided within an expression vector such that transformation with the vector results in expression of the polypeptide; suitable vectors are described above and following.

A transgenic organism is grown under conditions sufficient to modify fatty acid composition. In some embodiments of the present invention, a transgenic organism is supplied with exogenous substrates of the ADS (as, for example, in a fermenter). Such substrates can comprise sugars as carbon sources for fatty acid synthesis, fatty acids and glycerol used directly for the production of DAG and TAG, DAG itself, and acetic acid which will both provide a general carbon source and be used for the production of fatty acids diacylglycerols (DAGs). Substrates may be supplied in various forms as are well known in the art; such forms include aqueous suspensions prepared by sonication, aqueous suspensions prepared with detergents and other surfactants, dissolution of the substrate into a solvent, and dried powders of substrates. Such forms may be added to organisms or cultured cells or tissues grown in fermenters.

In yet other embodiments of the present invention, a transgenic organism comprises a heterologous gene encoding an ADS of the present invention operably linked to an inducible promoter, and is grown either in the presence of the an inducing agent, or is grown and then exposed to an inducing agent.

In still other embodiments of the present invention, a transgenic organism comprises a heterologous gene encoding an ADS of the present invention operably linked to a promoter which is either tissue specific or developmentally specific, and is grown to the point at which the tissue is developed or the developmental stage at which the developmentally-specific promoter is activated. Such promoters include seed specific promoters.

In other embodiments of the present invention, the methods for modifying fatty acid composition further comprise collecting the fatty acids produced. Such methods are known generally in the art, and include harvesting the transgenic organisms and extracting the fatty acids (see, for example, Christie, W. W. (1982) *Lipid Analysis*, 2$^{nd}$ Edition (Pergamon Press, Oxford); and Kates, M (1986) *Techniques of Lipidology* (Elsevier, Amsterdam)). Extraction procedures preferably include solvent extraction, and typically include disrupting cells, as by chopping, mincing, grinding, and/or sonicating, prior to solvent extraction. In one embodiment, lipids are extracted from the tissue according to the method of Bligh and Dyer (1959) (Can J Biochem Physiol 37: 911-917). In yet other embodiments of the present invention, the fatty acids are further purified, as for example by thin layer liquid chromatography, gas-liquid chromatography, counter current chromatography or high performance liquid chromatography.

1. Transgenic Plant Cells, Plant Tissues, Plant Seeds, and Plants

Thus, in particular embodiments, the present invention provides methods to decrease saturated fatty acid of a transgenic plant cell, a transgenic plant tissue, a transgenic plant organ (such as a seed), or a transgenic plant by expressing or overexpressing ADS coding sequences in the transgenic plant cell, the transgenic plant tissue, the transgenic plant organ (such as a seed), or the transgenic plant. In some embodiments, expressing or overexpressing ADS is achieved by the presence of a heterologous ADS coding sequence, where a heterologous ADS coding sequence includes but is not limited to an ADS coding sequence obtained from a source different from the transgenic plant cell, plant tissue, plant seed, or plant, or an endogenous ADS coding sequence (in other words, naturally occurring) operably linked to a heterologous promoter.

The present invention also provides methods to increase unsaturated fatty acid of a transgenic plant cell, a transgenic plant tissue, a transgenic plant organ (such as a seed), or a transgenic plant by expressing or overexpressing ADS coding sequences in the transgenic plant cell, the transgenic plant tissue, the transgenic plant organ (such as a seed), or the transgenic plant. In some embodiments, expressing or overexpressing ADS is achieved by the presence of a heterologous ADS coding sequence, where a heterologous ADS coding sequence includes but is not limited to an ADS coding sequence obtained from a source different from the transgenic plant cell, plant tissue, plant seed, or plant, or an endogenous ADS coding sequence (in other words, naturally occurring) operably linked to a heterologous promoter.

Accordingly, in some embodiments, expression in plants of nucleic acid sequences encoding an ADS of the present invention leads to the overexpression of ADS in transgenic plant cells, transgenic plant tissues, transgenic plant organs (such as seeds), or transgenic plants. In particular embodiments, the expression of an ADS without a transit peptide (for example, ADS1, ADS2, or ADS3(72-371) and operably linked to a seed promoter in a plant seed is utilized to modify fatty acid of seed oils. In other particular embodiments, the expression of an ADS with a transit peptide, either naturally occurring in the ADS (for example, ADS3), or in a fusion protein (for example, ADS3(1-71)-ADS1 and ADS3(1071)-ADS2) and operably linked to a seed promoter in a plant seed is utilized to modify fatty acid of seed oils.

Plants are transformed with at least a heterologous gene encoding an ADS of the present invention according to procedures well known in the art. It is contemplated that the heterologous gene is utilized to increase the level of the enzyme activities encoded by the heterologous gene.

a. Plants

The methods of the present invention are not limited to any particular plant. Indeed, a variety of plants are contemplated, including but not limited to tomato, potato, tobacco, pepper, rice, corn, barley, wheat, *Brassica*, *Arabidopsis*, sunflower, soybean, poplar, and pine. Preferred plants include oil-producing species, which are plant species that produce and store triacylglycerol in specific organs, primarily in seeds. Such species include but are not limited to soybean (*Glycine max*), rapeseed and canola (including *Brassica napus* and *B. campestris*), sunflower (*Helianthus annus*), cotton (*Gossypium hirsutum*), corn (*Zea mays*), cocoa (*Theobrama cacao*), safflower (*Carthamus tinctorius*), oil palm (*Elaeis guineensis*), coconut palm (*Cocos nucifera*), flax (*Linum usitatissimum*), castor (*Ricinus communis*) and peanut (*Arachis hypogaea*). The group also includes non-agronomic species which are useful in developing appropriate expression vectors such as tobacco, rapid cycling *Brassica* species, and *Arabidopsis thaliana*, and wild species undergoing domestication, such as *Vernonia* and *Cuphea*, which may be a source of unique fatty acids.

b. Vectors

The methods of the present invention contemplate the use of at least a heterologous gene encoding an ADS of the present invention, as described above.

Heterologous genes intended for expression in plants are first assembled in expression cassettes comprising a promoter. Methods that are well known to those skilled in the art may be used to construct expression vectors containing a heterologous gene and appropriate transcriptional and translational control elements. These methods include in vitro recombinant DNA techniques, synthetic techniques, and in vivo genetic recombination. Such techniques are widely described in the art (See e.g., Sambrook. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y).

In general, these vectors comprise a nucleic acid sequence of the invention encoding an ADS of the present invention (as described above) operably linked to a promoter and other regulatory sequences (e.g., enhancers, polyadenylation signals, etc.) required for expression in a plant.

Promoters include but are not limited to constitutive promoters, tissue-, organ-, and developmentally-specific promoters, and inducible promoters. Examples of promoters include but are not limited to: constitutive promoter 35S of cauliflower mosaic virus; a wound-inducible promoter from tomato, leucine amino peptidase ("LAP," Chao et al. (1999) Plant Physiol 120: 979-992); a chemically-inducible promoter from tobacco, Pathogenesis-Related 1 (PR1) (induced by salicylic acid and BTH (benzothiadiazole-7-carbothioic acid S-methyl ester)); a tomato proteinase inhibitor II promoter (PIN2) or LAP promoter (both inducible with methyl jasmonate); a heat shock promoter (U.S. Pat. No. 5,187,267); a tetracycline-inducible promoter (U.S. Pat. No. 5,057,422); and seed-specific promoters, such as those for seed storage proteins (e.g., phaseolin, napin, oleosin, and a promoter for soybean beta conglycin (Beachy et al. (1985) EMBO J. 4: 3047-3053)). In some preferred embodiments, the promoter is a phaseolin promoter. All references cited herein are incorporated in their entirety.

The expression cassettes may further comprise any sequences required for expression of mRNA. Such sequences include, but are not limited to transcription terminators, enhancers such as introns, viral sequences, and sequences intended for the targeting of the gene product to specific organelles and cell compartments.

A variety of transcriptional terminators are available for use in expression of sequences using the promoters of the present invention. Transcriptional terminators are responsible for the termination of transcription beyond the transcript and its correct polyadenylation. Appropriate transcriptional terminators and those which are known to function in plants include, but are not limited to, the CaMV 35S terminator, the tml terminator, the pea rbcS E9 terminator, and the nopaline and octopine synthase terminator (See e.g., Odell et al. (1985) Nature 313:810; Rosenberg et al. (1987) Gene, 56:125; Guerineau et al. (1991) Mol. Gen. Genet., 262:141; Proudfoot (1991) Cell, 64:671; Sanfacon et al. Genes Dev., 5:141; Mogen et al. (1990) Plant Cell, 2:1261; Munroe et al. (1990) Gene, 91:151; Ballad et al. (1989) Nucleic Acids Res. 17:7891; Joshi et al. (1987) Nucleic Acid Res., 15:9627).

In addition, in some embodiments, constructs for expression of the gene of interest include one or more of sequences found to enhance gene expression from within the transcriptional unit. These sequences can be used in conjunction with the nucleic acid sequence of interest to increase expression in plants. Various intron sequences have been shown to enhance expression, particularly in monocotyledonous cells. For example, the introns of the maize Adh1 gene have been found to significantly enhance the expression of the wild-type gene under its cognate promoter when introduced into maize cells (Calais et al. (1987) Genes Develop. 1: 1183). Intron sequences have been routinely incorporated into plant transformation vectors, typically within the non-translated leader.

In some embodiments of the present invention, the construct for expression of the nucleic acid sequence of interest also includes a regulator such as a nuclear localization signal (Calderone et al. (1984) Cell 39:499; Lassoer et al. (1991) Plant Molecular Biology 17:229), a plant translational consensus sequence (Joshi (1987) Nucleic Acids Research 15:6643), an intron (Luehrsen and Walbot (1991) Mol. Gen. Genet. 225:81), and the like, operably linked to the nucleic acid sequence encoding ADS.

In preparing a construct comprising a nucleic acid sequence encoding ADS of the present invention, various DNA fragments can be manipulated, so as to provide for the DNA sequences in the desired orientation (e.g., sense or antisense) orientation and, as appropriate, in the desired reading frame. For example, adapters or linkers can be employed to join the DNA fragments or other manipulations can be used to provide for convenient restriction sites, removal of superfluous DNA, removal of restriction sites, or the like. For this purpose, in vitro mutagenesis, primer repair, restriction, annealing, resection, ligation, or the like is preferably employed, where insertions, deletions or substitutions (e.g., transitions and transversions) are involved.

Numerous transformation vectors are available for plant transformation. The selection of a vector for use will depend upon the preferred transformation technique and the target species for transformation. For certain target species, different antibiotic or herbicide selection markers are preferred. Selection markers used routinely in transformation include the nptII gene which confers resistance to kanamycin and related antibiotics (Messing and Vierra (1982) Gene 19: 259; Bevan et al. (1983) Nature 304:184), the bar gene which confers resistance to the herbicide phosphinothricin (White et al. (1990) Nucl Acids Res. 18:1062; Spencer et al. (1990) Theor. Appl. Genet. 79:625), the hph gene which confers resistance to the antibiotic hygromycin (Blochlinger and Diggelmann (1984) Mol. Cell. Biol. 4:2929), and the dhfr gene, which confers resistance to methotrexate (Bourouis et al. (1983) EMBO J., 2:1099).

In some preferred embodiments, the vector is adapted for use in an *Agrobacterium* mediated transfection process (See e.g., U.S. Pat. Nos. 5,981,839; 6,051,757; 5,981,840; 5,824,877; and 4,940,838; all of which are incorporated herein by reference). Construction of recombinant Ti and Ri plasmids in general follows methods typically used with the more common bacterial vectors, such as pBR322. Additional use can be made of accessory genetic elements sometimes found with the native plasmids and sometimes constructed from foreign sequences. These may include but are not limited to structural genes for antibiotic resistance as selection genes.

There are two systems of recombinant Ti and Ri plasmid vector systems now in use. The first system is called the "cointegrate" system. In this system, the shuttle vector containing the gene of interest is inserted by genetic recombination into a non-oncogenic Ti plasmid that contains both the cis-acting and trans-acting elements required for plant transformation as, for example, in the pMLJ1 shuttle vector and the non-oncogenic Ti plasmid pGV3850. The second system is called the "binary" system in which two plasmids are used; the gene of interest is inserted into a shuttle vector containing the cis-acting elements required for plant transformation. The other necessary functions are provided in trans by the non-oncogenic Ti plasmid as exemplified by the pBIN19 shuttle vector and the non-oncogenic Ti plasmid PAL4404. Some of these vectors are commercially available.

In other embodiments of the invention, the nucleic acid sequence of interest is targeted to a particular locus on the plant genome. Site-directed integration of the nucleic acid sequence of interest into the plant cell genome may be achieved by, for example, homologous recombination using *Agrobacterium*-derived sequences. Generally, plant cells are incubated with a strain of *Agrobacterium* which contains a targeting vector in which sequences that are homologous to a DNA sequence inside the target locus are flanked by *Agrobacterium* transfer-DNA (T-DNA) sequences, as previously described (U.S. Pat. No. 5,501,967). One of skill in the art knows that homologous recombination may be achieved using targeting vectors that contain sequences that are homologous to any part of the targeted plant gene, whether belonging to the regulatory elements of the gene, or the coding regions of the gene. Homologous recombination may be achieved at any region of a plant gene so long as the nucleic acid sequence of regions flanking the site to be targeted is known.

In yet other embodiments, the nucleic acids of the present invention are utilized to construct vectors derived from plant (+) RNA viruses (e.g., brome mosaic virus, tobacco mosaic virus, alfalfa mosaic virus, cucumber mosaic virus, tomato mosaic virus, and combinations and hybrids thereof). Generally, the inserted ADS polynucleotide of the present invention can be expressed from these vectors as a fusion protein (e.g., coat protein fusion protein) or from its own subgenomic promoter or other promoter. Methods for the construction and use of such viruses are described in U.S. Pat. Nos. 5,846,795; 5,500,360; 5,173,410; 5,965,794; 5,977,438; and 5,866,785, all of which are incorporated herein by reference.

In some embodiments of the present invention the nucleic acid sequence of interest is introduced directly into a plant. One vector useful for direct gene transfer techniques in combination with selection by the herbicide Basta (or phosphinothricin) is a modified version of the plasmid pCIB246, with a CaMV 35S promoter in operational fusion to the *E. coli* GUS gene and the CaMV 35S transcriptional terminator (WO 93/07278).

C. Transformation Techniques

Once a nucleic acid sequence encoding an ADS of the present invention is operatively linked to an appropriate promoter and inserted into a suitable vector for the particular transformation technique utilized (e.g., one of the vectors described above), the recombinant DNA described above can be introduced into the plant cell in a number of art-recognized ways. Those skilled in the art will appreciate that the choice of method might depend on the type of plant targeted for transformation. In some embodiments, the vector is maintained episomally. In other embodiments, the vector is integrated into the genome.

In some embodiments, direct transformation in the plastid genome is used to introduce the vector into the plant cell (See e.g., U.S. Pat. Nos. 5,451,513; 5,545,817; 5,545,818; PCT application WO 95/16783). The basic technique for chloroplast transformation involves introducing regions of cloned plastid DNA flanking a selectable marker together with the nucleic acid encoding the RNA sequences of interest into a suitable target tissue (e.g., using biolistics or protoplast transformation with calcium chloride or PEG). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab et al. (1990) PNAS, 87:8526; Staub and Maliga, (1992) Plant Cell, 4:39). The presence of cloning sites between these markers allowed creation of a plastid targeting vector introduction of foreign DNA molecules (Staub and Maliga (1993) EMBO J., 12:601). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab and Maliga (1993) PNAS, 90:913). Other selectable markers useful for plastid transformation are known in the art and encompassed within the scope of the present invention. Plants homoplasmic for plastid genomes containing the two nucleic acid sequences separated by a promoter of the present invention are obtained, and are preferentially capable of high expression of the RNAs encoded by the DNA molecule.

In other embodiments, vectors useful in the practice of the present invention are microinjected directly into plant cells by use of micropipettes to mechanically transfer the recombinant DNA (Crossway (1985) Mol. Gen. Genet, 202:179). In still other embodiments, the vector is transferred into the plant cell by using polyethylene glycol (Krens et al. (1982) Nature, 296:72; Crossway et al. (1986) BioTechniques, 4:320); fusion of protoplasts with other entities, either minicells, cells, lysosomes or other fusible lipid-surfaced bodies (Fraley et al. (1982) Proc. Natl. Acad. Sci., USA, 79:1859); protoplast transformation (EP 0 292 435); direct gene transfer (Paszkowski et al. (1984) EMBO J., 3:2717; Hayashimoto et al. (1990) Plant Physiol. 93:857).

In still further embodiments, the vector may also be introduced into the plant cells by electroporation (Fromm, et al. (1985) Proc. Natl. Acad. Sci. USA 82:5824; Riggs et al. (1986) Proc. Natl. Acad. Sci. USA 83:5602). In this technique, plant protoplasts are electroporated in the presence of plasmids containing the gene construct. Electrical impulses of high field strength reversibly permeabilize biomembranes allowing the introduction of the plasmids. Electroporated plant protoplasts reform the cell wall, divide, and form plant callus.

In yet other embodiments, the vector is introduced through ballistic particle acceleration using devices (e.g., available from Agracetus, Inc., Madison, Wis. and Dupont, Inc., Wilmington, Del). (See e.g., U.S. Pat. No. 4,945,050; and McCabe et al. (1988) Biotechnology 6:923). See also, Weissinger et al. (1988) Annual Rev. Genet. 22:421; Sanford et al. (1987) Particulate Science and Technology, 5:27 (onion); Svab et al. (1990) Proc. Natl. Acad. Sci. USA, 87:8526 (tobacco chloroplast); Christou et al. (1988) Plant Physiol., 87:671 (soybean); McCabe et al. (1988) Bio/Technology 6:923 (soybean); Klein et al. (1988) Proc. Natl. Acad. Sci. USA, 85:4305 (maize); Klein et al. (1988) Bio/Technology, 6:559 (maize); Klein et al. (1988) Plant Physiol., 91:4404 (maize); Fromm et al. (1990) Bio/Technology, 8:833; and Gordon-Kamm et al (1990) Plant Cell, 2:603 (maize); Koziel et al. (1993) Biotechnology, 11:194 (maize); Hill et al. (1995) Euphytica, 85:119 and Koziel et al. (1996) Annals of the New York Academy of Sciences 792:164; Shimamoto et al. (1989) Nature 338: 274 (rice); Christou et al. (1991) Biotechnology, 9:957 (rice); Datta et al. (1990) Bio/Technology 8:736 (rice); European Patent Application EP 0 332 581 (orchardgrass and other Pooideae); Vasil et al. (1993) Biotechnology, 11: 1553 (wheat); Weeks et al. (1993) Plant Physiol., 102: 1077 (wheat); Wan et al. (1994) Plant Physiol. 104: 37 (barley); Jahne et al. (1994) Theor. Appl. Genet. 89:525 (barley); Knudsen and Muller (1991) Planta, 185:330 (barley); Umbeck et al. (1987) Bio/Technology 5: 263 (cotton); Casas et al. (1993) Proc. Natl. Acad. Sci. USA 90:11212 (sorghum); Somers et al. (1992) Bio/Technology 10: 1589 (oat); Torbert et al. (1995) Plant Cell Reports, 14:635 (oat); Weeks et al. (1993) Plant Physiol., 102:1077 (wheat); Chang et al., WO 94/13822 (wheat) and Nehra et al. (1994) The Plant Journal, 5:285 (wheat).

In addition to direct transformation, in some embodiments, the vectors comprising a nucleic acid sequence encoding an ADS of the present invention are transferred using *Agrobacterium*-mediated transformation (Hinchee et al. (1988) Biotechnology, 6:915; Ishida et al. (1996) Nature Biotechnology 14:745). *Agrobacterium* is a representative genus of the gram-negative family Rhizobiaceae. Its species are responsible for plant tumors such as crown gall and hairy root disease. In the dedifferentiated tissue characteristic of the tumors, amino acid derivatives known as opines are produced and catabolized. The bacterial genes responsible for expression of opines are a convenient source of control elements for chimeric expression cassettes. Heterologous genetic sequences (e.g., nucleic acid sequences operatively linked to a promoter of the present invention), can be introduced into appropriate plant cells, by means of the Ti plasmid of *Agrobacterium tumefaciens*. The Ti plasmid is transmitted to plant cells on infection by *Agrobacterium tumefaciens*, and is stably integrated into the plant genome (Schell (1987) Science, 237: 1176). Species that are susceptible to infection by *Agrobacterium* may be transformed in vitro. Alternatively, plants may be transformed in vivo, such as by transformation of a whole plant by Agrobacteria infiltration of adult plants, as in a "floral dip" method (Bechtold N, Ellis J, Pelletier G (1993) Cr. Acad. Sci. III—Vie 316: 1194-1199).

d. Regeneration

After selecting for transformed plant material that can express the heterologous gene encoding an ADS of the present invention, whole plants are regenerated. Plant regeneration from cultured protoplasts is described in Evans et al. (1983) Handbook of Plant Cell Cultures, Vol. 1: (MacMillan Publishing Co. New York); and Vasil I. R. (ed.), Cell Culture and Somatic Cell Genetics of Plants, Acad. Press, Orlando, Vol. I (1984), and Vol. III (1986). It is known that many plants can be regenerated from cultured cells or tissues, including but not limited to all major species of sugarcane, sugar beet, cotton, fruit and other trees, legumes and vegetables, and monocots (e.g., the plants described above). Means for regeneration vary from species to species of plants, but generally a suspension of transformed protoplasts containing copies of the heterologous gene is first provided. Callus tissue is formed and shoots may be induced from callus and subsequently rooted.

Alternatively, embryo formation can be induced from the protoplast suspension. These embryos germinate and form mature plants. The culture media will generally contain various amino acids and hormones, such as auxin and cytokinins. Shoots and roots normally develop simultaneously. Efficient regeneration will depend on the medium, on the genotype, and on the history of the culture. The reproducibility of regeneration depends on the control of these variables.

e. Generation of Transgenic Lines

Transgenic lines are established from transgenic plants by tissue culture propagation. The presence of nucleic acid sequences encoding a heterologous ADS of the present invention (including mutants or variants thereof) may be transferred to related varieties by traditional plant breeding techniques.

These transgenic lines are then utilized for evaluation of oil production and other agronomic traits.

B. Decreasing ADS Activity in Cells

In other embodiments of the present invention, saturated fatty acids are increased, and/or unsaturated fatty acids are decreased, by providing an organism transformed with a heterologous gene encoding a product which decreases expression of ADS of the present invention or an ADS-like activity and growing the transgenic organism under conditions sufficient to modify the fatty acid composition. In other embodiments of the present invention, saturated fatty acids are increased, and/or unsaturated fatty acids are decreased, by transforming an organism with a heterologous gene encoding a product which decreases expression of ADS of the present invention or an ADS-like activity, and growing the transgenic organism under conditions sufficient to modify the fatty acid composition.

It is contemplated that desaturases with characteristics similar to the ADS genes of the present invention are present in other plants; these desaturases are referred to as "ADS-like." It is also contemplated that these "ADS-like" desaturases will be homologous to ADS of the present invention, with at least about 45% amino acid identity, or at least about 50% amino acid identity, or at least about 55% amino acid identity (see, for example, Marilla, E-F et al. (2002) FEBS Let 526:49). Thus, in particular embodiments, antisense sequences to ADS coding sequences of the present invention, and siRNAs targeted to ADS coding sequences of the present invention, are contemplated to decrease expression of ADS-like desaturases in plants other than *Arabidopsis*.

It is further contemplated that "ADS-like" desaturases will share regions of high amino acid similarity and/or identity with ADS of the present invention, for example in the three histidine-rich motifs that are highly conserved among membrane bound acyl-CoA and acyl-lipid desaturases and believed to correspond to a diriron active site of the enzyme (Marilla, E-F et al. (2002), supra). It is further contemplated that "ADS-like" desaturases will share regions of high amino acid similarity and/or identity with ADS of the present invention, where the highly similar regions of the ADS-like desaturases are essentially specific to these desaturases. Amino acid comparisons are made by well known methods which include aligning the amino acid sequences, and determining which regions share the highest identity or similarity. These regions of high similarity and/or identity which are essentially specific to ADS-like desaturases are contemplated to be particularly suitable target sequences for decreasing expression of ADS or ADS-like desaturases in plant cells, plant tissues, plant organs (such as seeds), and plants. Thus, in other particular embodiments, antisense sequences coding sequences for amino acid regions of high similarity and/or identity which are essentially specific to ADS-like desaturases, and siRNAs sequences targeted to coding sequences for amino acid regions of high similarity and/or identity which are essentially specific to ADS-like desaturases, are contemplated to decreased expression of ADS-like desaturases in plants other than *Arabidopsis*.

Organisms which are transformed with a heterologous gene encoding a product which decreases expression of ADS of the present invention or an ADS-like activity include preferably those which naturally synthesize and store in some manner triacylglycerols (TAGs), and those which are commercially feasible to grow and suitable for harvesting large amounts of the TAG products. Such organisms include but are not limited to, oleaginous yeast and algae, and plants and animals. Examples of yeasts include oleaginous yeast, which include but are not limited to the genera *Lipomyces, Candida, Rhodotorula, Rhodosporidium* and *Cryptococcus*, which can be grown in commercial-scale fermenters. Examples of plants include preferably oil-producing plants, such as soybean, rapeseed and canola, sunflower, cotton, corn, cocoa, safflower, oil palm, coconut palm, flax, castor, and peanut. Many commercial cultivars can be transformed with heterologous genes. In cases where that is not possible, non-commercial cultivars of plants can be transformed, and the trait for expression of ADS of the present invention or modified fatty acid composition moved to commercial cultivars by breeding techniques well-known in the art.

A heterologous gene encoding a product that decreases expression of ADS of the present invention or an ADS-like activity is described below. In particular embodiments, the gene product is a nucleic acid targeted to a sequence in an ADS of the present invention as described above or an ADS-like activity. Preferably, the heterologous gene is provided within an expression vector such that transformation with the vector results in expression of the polypeptide; suitable vectors are described above and following.

A transgenic organism is grown under conditions sufficient to modify fatty acid composition, as described above.

In yet other embodiments of the present invention, a transgenic organism comprises a heterologous gene encoding a product which decreases expression of ADS of the present invention, where the heterologous gene is operably linked to an inducible promoter, and is grown either in the presence of the an inducing agent, or is grown and then exposed to an inducing agent. In still other embodiments of the present invention, a transgenic organism comprises a heterologous gene encoding a product which decreases expression of ADS of the present invention or an ADS-like activity operably linked to a promoter which is either tissue specific or developmentally specific, and is grown to the point at which the tissue is developed or the developmental stage at which the developmentally-specific promoter is activated. Such promoters include seed specific promoters.

In other embodiments of the present invention, the methods for modifying fatty acid composition further comprise collecting the fatty acids produced. Such methods are known generally in the art, and are described above.

1. Transgenic Plant Cells, Plant Tissues, Plant Seeds, and Plants

Thus, in particular embodiments, the present invention provides methods to increase saturated fatty acid of a transgenic plant cell, a transgenic plant tissue, a transgenic plant organ (such as a seed), or a transgenic plant by decreasing expression of an ADS or ADS-like coding sequences in the transgenic plant cell, the transgenic plant tissue, the transgenic plant organ (such as a seed), or the transgenic plant. In some embodiments, decreasing expression of ADS or an ADS-like coding sequence is achieved by the presence of a heterologous gene encoding a nucleic acid product which targets an ADS or ADS-like coding sequence.

The present invention also provides methods to increase saturated fatty acid of a transgenic plant cell, a transgenic plant tissue, a transgenic plant organ (such as a seed), or a transgenic plant by decreasing expression of ADS or ADS-like coding sequences in the transgenic plant cell, the transgenic plant tissue, the transgenic plant organ (such as a seed), or the transgenic plant. In some embodiments, decreasing expression ADS or ADS-like coding sequence is achieved by the presence of a heterologous the presence of a heterologous gene encoding a nucleic acid product which targets an ADS or ADS-like coding sequence.

Thus, in some embodiments of the present invention, ADS or ADS-like coding sequences are utilized to decrease the level of ADS protein or mRNA in transgenic plants, plant tissues, or plant cells as compared to wild-type plants, plant tissues, or plant cells, thereby resulting in modified fatty acid composition. One method of reducing ADS expression utilizes expression of antisense transcripts. Antisense RNA has been used to inhibit plant target genes in a tissue-specific manner (e.g., van der Krol et al. (1988) Biotechniques 6:958-976). Antisense inhibition has been shown using the entire cDNA sequence as well as a partial cDNA sequence (e.g., Sheehy et al. (1988) Proc. Natl. Acad. Sci. USA 85:8805-8809; Cannon et al. (1990) Plant Mol. Biol. 15:39-47). There is also evidence that 3' non-coding sequence fragment and 5' coding sequence fragments, containing as few as 41 basepairs of a 1.87 kb cDNA, can play important roles in antisense inhibition (Ch'ng et al. (1989) Proc. Natl. Acad. Sci. USA 86:10006-10010).

Accordingly, in some embodiments, an ADS encoding-nucleic acid of the present invention (for example, SEQ ID NOs:1, 3, 5, and 7, and fragments and variants thereof) are oriented in a vector and expressed so as to produce antisense transcripts. To accomplish this, a nucleic acid segment from the desired gene is cloned and operably linked to a promoter such that the antisense strand of RNA will be transcribed. The expression cassette is then transformed into plants and the antisense strand of RNA is produced. The nucleic acid segment to be introduced generally will be substantially identical to at least a portion of the endogenous gene or genes to be repressed. The sequence, however, need not be perfectly identical to inhibit expression. The vectors of the present invention can be designed such that the inhibitory effect applies to other proteins within a family of genes exhibiting homology or substantial homology to the target gene.

Furthermore, for antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of at least about 500 nucleotides is especially preferred.

Catalytic RNA molecules or ribozymes can also be used to inhibit expression of the target gene or genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs that are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, *Solanum nodiflorum* mottle virus and subterranean clover mottle virus. The design and use of target RNA-specific ribozymes is described in Haseloff, et al. (1988) Nature 334:585-591. Ribozymes targeted to the mRNA of a lipid biosynthetic gene, resulting in a heritable increase of the target enzyme substrate, have also been described (Merlo A O et al. (1998) Plant Cell 10: 1603-1621).

Another method of reducing ADS expression utilizes the phenomenon of cosuppression or gene silencing (See e.g., U.S. Pat. No. 6,063,947, incorporated herein by reference). The phenomenon of cosuppression has also been used to inhibit plant target genes in a tissue-specific manner. Cosuppression of an endogenous gene using a full-length cDNA sequence as well as a partial cDNA sequence (730 bp of a 1770 bp cDNA) are known (e.g., Napoli et al. (1990) Plant Cell 2:279-289; van der Krol et al. (1990) Plant Cell 2:291-299; Smith et al. (1990) Mol. Gen. Genetics 224:477-481). Accordingly, in some embodiments the nucleic acid sequences encoding an ADS of the present invention (e.g. including SEQ ID NOs: 1, 3, 5, and 7, and fragments and variants thereof) are expressed in another species of plant to effect cosuppression of a homologous gene.

Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For cosuppression, the introduced sequence in the expression cassette, needing less than absolute identity, also need not be full length, relative to either the primary transcription product or fully processed mRNA. This may be preferred to avoid concurrent production of some plants that are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used.

An effective method to down regulate a gene is by hairpin RNA constructs. Guidance to the design of such constructs for efficient, effective and high throughput gene silencing have been described (Wesley SV et al. (2001) Plant J. 27: 581-590). Another method to decrease expression of a gene (either endogenous or exogenous) is via siRNAs. siRNAs can be applied to a plant and taken up by plant cells; alternatively, siRNAs can be expressed in vivo from an expression cassette. Exemplary techniques for lipid gene antisense using hairpin RNA include Stoutjesdijk et al. (2002) Plant Physiol. 129: 1723; Liu et al. (2002) Plant Physiol. 129: 1732).

An advantage of siRNAs is the short length of the mRNA that is targeted; this allows preferential targeting of a first sequence that is very similar to a second sequence, while allowing expression of the second, non-targeted sequence. Thus, it is contemplated that ADS is specifically targeted, but not a related desaturase.

The methods of the present invention include promoters, vectors, plants, transformation, regeneration, and establishment of plant lines as described above.

VI. Production of Unsaturated Fatty Acids In Vitro

In other embodiments, the present invention provides methods for producing unsaturated fatty acids in vitro, from either nucleic acid sequences encoding an ADS of the present invention or from polypeptides exhibiting an ADS activity.

A. Using Nucleic Acid Sequences Encoding ADS

In some embodiments of the present invention, methods for producing unsaturated fatty acids comprise adding an isolated nucleic acid sequence encoding an ADS of the present invention to in vitro expression systems under conditions sufficient to cause production of unsaturated fatty acids. The isolated nucleic acid sequence encoding an ADS is any suitable sequence of the invention as described above, and preferably is provided within an expression vector such that addition of the vector to an in vitro transcription/translation system results in expression of the polypeptide. Furthermore, the system contemplated is specific for the translation and function of eukaryotic membrane proteins, that is, it is a microsomal system. The system further comprises the substrates for fatty acid desaturation, as previously described. Alternatively, the system further comprises the means for generating the substrates for an fatty acid desaturation of the present invention. Such means include but are not limited to those previously described.

In other embodiments of the present invention, the methods for producing large quantities of unsaturated fatty acids further comprise collecting the unsaturated fatty acids produced. Such methods are known generally in the art, and described briefly above. In yet other embodiments of the present invention, the unsaturated fatty acids are further purified, as for example by thin layer liquid chromatography, gas-liquid chromatography, high pressure liquid chromatography, crystallization and/or vacuum distillation.

B. Using ADS Polypeptides

In some embodiments of the present invention, methods for producing of unsaturated fatty acids comprise incubating an ADS of the present invention under conditions sufficient to result in the synthesis of unsaturated fatty acids.

An ADS polypeptide of the present invention, as described above, is obtained by purification of either naturally occurring ADS or recombinant ADS from an organism transformed with heterologous gene encoding an ADS, as described above. A source of naturally occurring ADS is contemplated to include *Arabidopsis*. A source of recombinant ADS is either plant, bacterial or other transgenic organisms, transformed with heterologous gene encoding ADS of the present invention, as described above. The recombinant ADS may include means for improving purification, as for example a 6×-His tag added to the C-terminus of the protein as described above. Alternatively, ADS is chemically synthesized.

The incubation mixture further comprises the substrates for ADS, as described above. Alternatively, the mixture further comprises the means for generating the substrates for ADS.

In other embodiments of the present invention, the methods for producing unsaturated fatty acids further comprise collecting the unsaturated fatty acids produced; such methods are described above.

EXPERIMENTAL

The following examples are provided in order to demonstrate and further illustrate certain preferred embodiments and aspects of the present invention and are not to be construed as limiting the scope thereof.

In the experimental disclosures which follow, the following abbreviations apply: N (normal); M (molar); mM (millimolar); 1M (micromolar); mol (moles); mmol (millimoles); μmol (micromoles); nmol (nanomoles); pmol (picomoles); g (grams); mg (milligrams); μg (micrograms); ng (nanograms); l or L (liters); ml (milliliters); μl (microliters); cm (centimeters); mm (millimeters); μm (micrometers); nm (nanometers); ° C. (degrees Centigrade); SC-ura (synthetic complete medium without uracil); SC-ura+FA (SC-ura was supplemented with 5 mM each of palmitoleic and oleic acid in final 0.1% (w/w) tergitol); OD (optical density); fab1 (an *Arabidopsis* mutant resulting in elevated levels of palmitic acid); fae1 (an *Arabidopsis* mutant resulting in the absence of fatty acids with more than 18 carbons) fad2 (an *Arabidopsis* mutant resulting in the absence of dienoic and trienoic acids) fad5 (an *Arabidopsis* mutant resulting in reduced desaturation of 16-carbon fatty acids in monogalactosyl diacylglycerol); BASTA (aorosolic ammonium glufosinate); GC (gas chromatography or gas chromatograph, depending upon the context); MS (mass spectrometry or mass spectrometer, depending upon the context); TMSH (trimethylsulfoniumhydroxide/methanol); DMDS (dimethyldisulfide);

Example 1

Materials and Methods

This example describes the materials and methods used in the characterization of ADS genes.

Yeast Growth and Transformation

The DTY10A-derived yeast strain DTY11A disrupted in the OLE1 gene and exhibiting no endogenous fatty acid desaturation was used as a host for complementation experiments. Cultures were initiated from single colonies and grown at 30° C. in synthetic complete medium without uracil, pH 6, containing 4% (w/w) glycerol and 0.8% (w/w) glucose (SC-ura). For growth of DTY11A, SC-ura was supplemented with 5 mM each of palmitoleic and oleic acid in final 0.1% (w/w) tergitol (SC-ura+FA). Solid media contained 1.2% (w/w) agar, 18% (w/w) sorbitol, and 1% (w/w) tergitol.

For growth experiments, 5-ml DTY11A cultures were grown in SC-ura+FA over night at 30° C. shaking at 150 rpm up to an optical density (OD) of approximately 2. Cells were pelleted by centrifugation, washed once in SC-ura and carefully resuspended. With the obtained cell material, 20-ml SC-ura cultures were inoculated at OD of about 0.5, and the growth was monitored. Pre-cultures transformed with pYES2 constructs were grown in SC-ura+FA in which glycerol/glucose was replaced by 4% raffinose. Cells were washed, resuspended and grown in induction media consisting of SC-ura plus 1% (w/w) galactose, with no raffinose, palmitoleic or oleic acid supplements added. All media were sterilized by filtration (0.2 um pore size; Nalgene, Rochester, N.Y., USA) prior to use. Growth was monitored at 600 nm, using a spectrophotometer (DU640, Beckmann).

For supplementation experiments, yeast DTY11A cultures expressing ADS genes were grown in 5 ml volume of induction media containing 10 mM of saturated fatty acids of varying chain length in final 0.1% tergitol (w/w). Growth was monitored over a period of 56 h. Data presented in Table 1 were obtained during logarithmic growth at 20 h, prior to entering the stationary phase. Yeast transformation was carried out according to Gietz and Woods, ((1994) In molecular genetics of yeast: practical approaches (Johnston J A, ed.), Oxford University Press, pp. 21-134).

Plant Growth and Transformation

*Arabidopsis* plants were grown in soil under exposure to about 300 uE of light in controlled environment growth chambers. As hosts for seed expression of the ADS genes, *Arabidopsis* plants mutated in a number of genes related to fatty acid metabolism were used as a genetic background. The mutations were in fab1, resulting in elevated levels of palmitic acid (compare James and Dooner, (1991) Theor Appl Genet 82:409); in fae1, resulting in the absence of fatty acids with more than 18 carbons (James and Dooner, 1991, supra); in fad2, resulting in the absence of dienoic and trienoic acids; in fad5 resulting in reduced desaturation of 16-carbon fatty acids in monogalactosyl diacylglycerol (Kunst et al., 1989, supra).

*Agrobacterium tumefaciens* cells were transformed with the respective pBBV PHAS or pBAR1 constructs by electroporation. Bacterial cultures were grown in LB medium containing 35 ug/l each of Rifampicin, Gentamicin and Spectinomycin over night in 300 ml cultures at 30° C. Cells were harvested by centrifugation and cell pellets were resuspended in 300 ml each of 5% (w/w) sucrose containing 0.5% Silwet L-77. Seven week-old *Arabidopsis* plants were transformed using the floral dip method (Clough and Bent, Plant J 16:735 (1998)) by submerging developing flowers four times for 5 s in *Agrobacterium* solution over a one-week period. The resulting transgenic plants were selected in soil for aorosolic ammonium glufosinate (BASTA) resistance.

cDNA Constructs cDNA-fragments of ADS1, ADS2 and ADS3 minus the sequence encoding the transit peptide (ADS3$^{72-371}$) were generated by polymerase chain reaction (PCR) from *Arabidopsis* flower cDNA using the primer combinations 5'-GCCTGGATCCATGTCATTGTCAGCCTCGGAGAAGG-3' (Primer A; SEQ ID NO:9)/5'-CAGTGAGCTCCGAGACGTCGTTCCATATCTTCAACG-3' (Primer B; SEQ ID NO:10), 5'-GCCTGGATCCATGTCGGTGACAT-CAACGGTGG-3' (Primer C; SEQ ID NO:11)/5'-CAGTGAGCTCTCAACGAACTATAGCCATACGACG-3' (Primer D; SEQ ID NO:12), and 5'-GCATGGATCCATGGGAGATTACAGAAGGATA-3' (Primer E; SEQ ID NO:13)/ 5'-CAGTGAATTCATACCTTTAAGTAAACA-CAAAAAAGC-3' (Primer F; SEQ ID NO:14), respectively. In the process, ADS3 codon72 (glu) was changed to atg (met). In addition, ADS3 including the sequence encoding the transit peptide was amplified from *Arabidopsis* flower cDNA using the primer combination 5'-CAGTGGATCCTAAGT-TAAGGGTTTAAGCCTCTTCTC-3' (Primer G; SEQ ID NO:15)/Primer F. The amplification protocol for ADS genes included an initial 2-min denaturation step at 94° C., 25 cycles of 30 s denaturation at 94° C., 30 s annealing at 57° C. and 2 min extension at 72° C., followed by 15 min extension at 72° C. For yeast complementation assays, the plasmid Yep352YOPR (Shanklin et al., 1994, Biochemistry 33:12787) was digested with BamHI and SacI, the vector band was gel-purified, creating Yep352YOP, and the BamHI/SacI cDNA fragments ADS1, ADS2, and ADS3$^{72-371}$ were moved into BamHI/SacI sites.

In order to check for DTY11A complementation under the stronger GAL1 promoter, ADS1, ADS2 and ADS3$^{72-371}$ cDNA fragments were excised from Yep352YOP with BamHI and EcoRI, and were moved into BamHI/EcoRI sites of the plasmid pYES2. The ADS3 cDNA fragment obtained in the initial step was also cloned into pYES2 in this fashion.

The binary expression vector pBBV PHAS was used for *Agrobacterium*-mediated transformation into *Arabidopsis* and expression in seeds under the phaseolin promoter. cDNA fragments for ADS1 and ADS3 were amplified from the respective pYES2 constructs using the primer combinations 5'-GATCTTAATTAAATGTCATTGTCAGCCTCG-3' (Primer H; SEQ ID NO:16)/5'- GATCGGCGCGCCTC-CGAGACGTCGTTCCATATC-3' (Primer I; SEQ ID NO:17) and 5'-GATCTTAATTAAATGGCTTCTCTTCTAACA-3' (Primer L; SEQ ID NO:18)/ 5'-GATCGGCGCGCCT-CAGTCGCTGGTGAATGC-3' (Primer M; SEQ ID NO:19).

The resulting PacI/AscI cDNA fragments were moved into PacI/AscI sites of pBBV PHAS. ADS2 and ADS3$^{72-371}$ cDNA fragments were excised from pYES2 with BamHI and XhoI, the BamHI sites were blunted and the fragments moved into PmeI/XhoI sites of pBBV PHAS.

The binary expression vector pBAR1 was used for *Agrobacterium*-mediated transformation into *Arabidopsis* and expression in leaves under the endogenous ADS3 promoter. The sequence encoding the ADS3 transit peptide was fused to ADS1 and ADS2 cDNA fragments by overlap extension PCR, creating ADS3$^{1-71}$-ADS1 and ADS3$^{1-71}$-ADS2. Step 1: ADS1 and ADS2 cDNA fragments were amplified from the respective pYES2 constructs using the primer combinations 5'-GCTGCTGCAGCGACGTTGTCATTGTCAGCC-3' (Primer P; SEQ ID NO:20)/5'-GATCTCTAGATC-CGAGACGTCGTTCCATATC-3' (Primer J; SEQ ID NO:21) and 5'-GCTGCTGCAGCGACGTTGTCGGTGACAT-CAACGG-3' (Primer S; SEQ ID NO:22)/5'-GATCTCTA-GATCAACGAACTATAGCCATACG-3'(Primer K; SEQ ID NO:23), respectively. ADS3$^{1-71}$ was amplified from pYES2-ADS3 using the primer combination 5'-GATCTTAAT-TAAATGGCTTCTCTTCTAACA-3' (Primer O; SEQ ID NO:24)/5'-GGCTGACAATGACAACGTCGCTGCAG-CAGC-3' (Primer Q; SEQ ID NO:25) or Primer O/5'-CCGT-TGATGTCACCGACAACGTCGCTGC-3' (Primer T; SEQ ID NO:26), respectively. The first step amplification protocol included 2 min denaturation at 94° C., 10 min annealing at 45° C. and 10 min extension at 72° C., followed by 29 cycles of 1 min denaturation at 94° C., 1 min annealing at 50° C., and 1 min extension at 72° C., followed by 15 min extension at 72° C. Step 2: The products from step 1 were gel-purified and fused using the primer combinations Primer O/Primer J and Primer O/Primer K, respectively. Second step amplification was carried out as described above for amplification of the ADS genes.

The genomic 600 bp non-translated region up-stream of ADS3 was amplified from *Arabidopsis* genomic DNA using the primer combination 5'-GATCGAATTCGGATTTTTCA-CACCACA-3' (Primer X; SEQ ID NO:27)/5'-GATCTTAAT-TAATATCGATGTGATGGCTAA-3' (Primer W; SEQ ID NO:28). The resulting PCR fragment was digested with PacI and ligated to each of the PacI-digested ADS3$^{1-71}$-ADS1, ADS3$^{1-71}$-ADS2 and ADS/FAD53 cDNA fragments. The ligation products of approx. 1,800 bp were gel-purified and directly amplified by PCR using the primer combinations Primer X/Primer J, Primer X/Primer K, and Primer X/5'-GATCTCTAGATCAGTCGCTGGTGAATGC-3' (Primer N; SEQ ID NO:29), respectively. The resulting EcoRI/XbaI cDNA fragments were moved into EcoRI/XbaI sites of pBAR1.

All amplifications were carried out using Advantage HF2 Taq-polymerase (Clontech). All restriction endonucleases and T4 DNA ligase were from New England Biolabs. Sequences of all constructs were verified prior to transformation.

Fatty Acid Derivatization and Analysis

Yeast cultures were harvested by centrifugation and the cell pellets dried under $N_2$. Fatty acids were extracted and methylated by adding 200 μl Boron trichloride ($BCl_3$) directly to the pellets and incubating for 30 min at 80° C. Fatty acid methyl esters were subsequently extracted according to Bligh and Dyer (Can. J. Biochem. Physiol. 37:911 (1959)). Fatty acids were analyzed using a Hewlett-Packard 5890 GC, fitted with a 30-m×320 um Omegawax 320 column (Supelco). The oven temperature was raised from 100 to 240° C. at a rate of 15° C. min−1, and held at 240° C. for 7 min. Total running time was 16.3 min. The double bond positions of monounsaturated fatty acid methyl esters were determined by GC-MS of dimethyl-disulfide adducts (Yamamoto et al., 1991 Chem Phys. Lipids 60:39). The fatty acid content of single seeds obtained from T1 plants was determined by GC analysis. Fatty acid methyl esters were prepared by homogenization of single seeds in 50 ul of trimethylsulfoniumhydroxide/methanol (TMSH) in a 100 ul-autosampler vial. After a 15-min incubation period at room temperature, samples were dried under $N_2$, resuspended in 35 ul of hexane, and analyzed by GC.

Example 2

Characterization of ADS Genes

This example describes the results of experiments characterizing ADS genes.

Expression of ADS1, ADS2 and ADS3$^{72-371}$ in the Yeast Unsaturated Fatty Acid Auxotroph DTY11A Overcomes the Requirement for Unsaturated Fatty Acid Supplementation.

Figure 2:
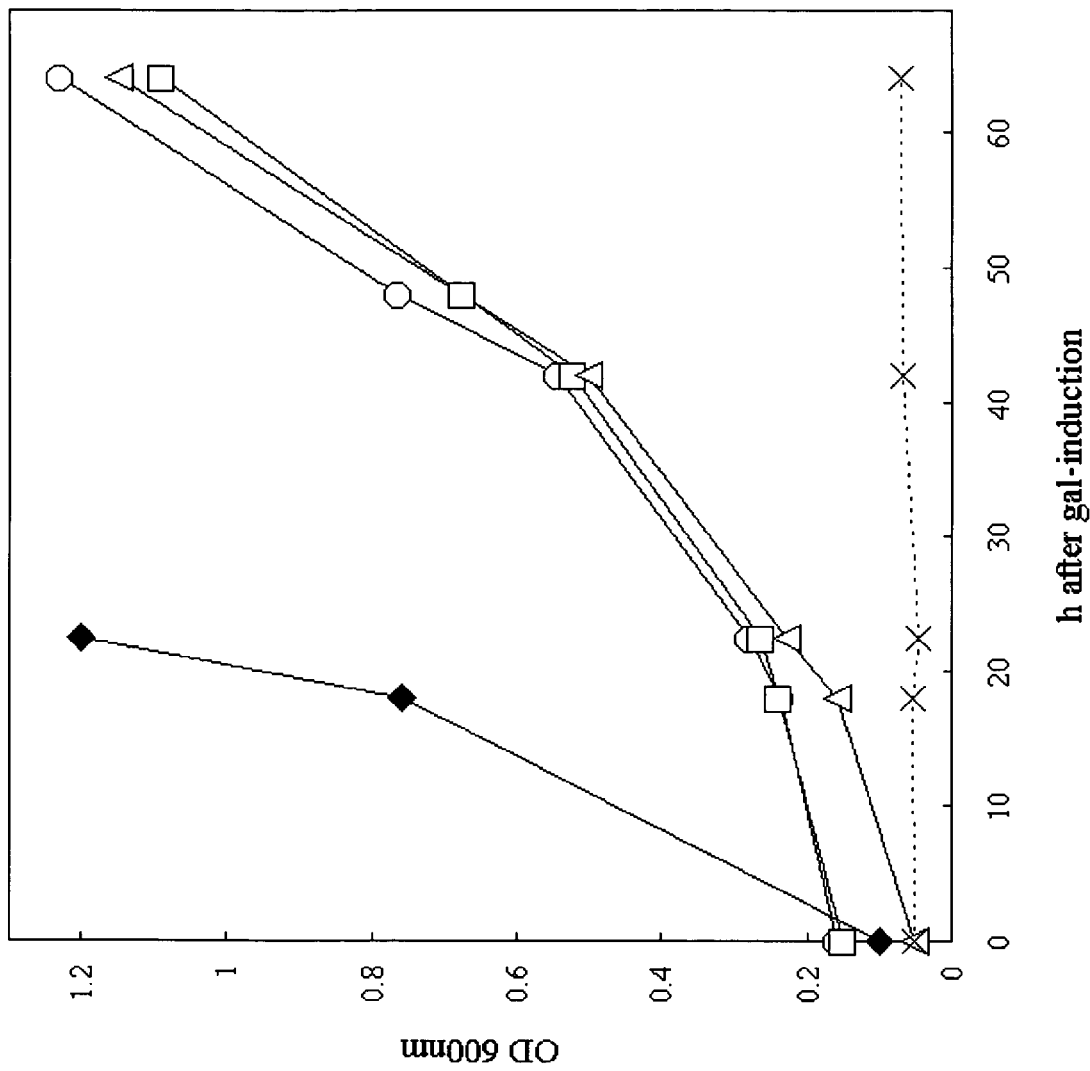
FIG. 2 shows complementation of the yeast ole1Δ mutation by the ADS desaturases. Open symbols, growth of DTY11A expressing ADS desaturases. Circles, ADS1; triangles, ADS2; squares, ADS3$^{72-371}$. Growth of DTY10A and of non-transformed DTY11A is indicated by closed diamonds and crosses, respectively.

In order to functionally test the ADS desaturases, whether they would complement an unsaturated fatty acid auxotroph DTY11A, a yeast strain in which the Δ9-stearoyl-CoA desaturase had been deleted, was examined. ADS1, ADS2 and ADS3 minus its transit peptide (ADS3$^{72-371}$) were expressed under the GAL1 promoter. Functional complementation was observed with all three constructs, because significant growth was observed in the absence of desaturated fatty acid supplementation (FIG. 2). The growth rates observed were slower that those for parental lines containing the endogenous yeast desaturase. Rates were somewhat variable between experiments, and complementation was not observed on solid media. Expression of Yep352YOP constructs driven by the yeast-endogenous OLE1 promoter did not result in significant complementation.

In Yeast, ADS1, ADS2, and ADS3$^{72-371}$ Generate Fatty Acids Desaturated in the Δ9 Position.

Fatty acids were extracted from complemented DTY11A cultures analyzed by GC/MS to characterize the products of the ADS desaturases (Table 1).

TABLE 1

Products generated by the ADS desaturases in yeast. The data were obtained from GC-traces for fatty acids extracted from DTY10A and from DTY11A expressing ADS desaturases.

| culture | 16:0 | 16:1Δ9 | 18:0 | 18:1Δ9 |
|---|---|---|---|---|
| | % of total fatty acids | | | |
| DTY10A (parent) | 11.2 | 47.4 | 3.8 | 37.6 |
| DTY11A ADS1 | 59.8 | 24.2 | 10.6 | 3.2 |
| DTY11A ADS2 | 53.2 | 28.7 | 10.4 | 4.8 |
| DTY11A ADS3 72-371 | 63.9 | 15.4 | 15.0 | 2.5 |

The main desaturated fatty acids present were palmitoleic, oleic, and vaccenic acid (Table 1). Double bond positions were identified by mass spectrometric analysis of dimethyldisulfide (DMDS) adducts of the desaturated products. Because genetic studies by Mekhedov et al. (2000) (supra) suggested FAD5 activity for ADS3, single ion monitoring for the 189 amu ion diagnostic for the presence of the 16:1 Δ7 monoene was performed. No significant amount of the DMDS adduct corresponding to 16:1 Δ7 was observed. The total level of unsaturates in typical ADS expressing culture of DTY11A was approximately 25%.

In Yeast, Palmitic Acid is a Preferred Substrate for ADS1, ADS2 and ADS3$^{72-371}$ Characterization of desaturation products that accumulate in yeast (Table 1) suggested a preference of the ADS desaturases for palmitic acid. In these experiments, DTY11A cultures expressing ADS1, ADS2 or ADS3$^{72-371}$ were supplied exogenously with a variety of saturated fatty acids, and the resulting growth was monitored. Under these conditions, fatty acid biosynthesis is down regulated, and the ability to continue growth should depend on the ability of the heterologously expressed ADS to desaturate the exogenously supplied substrate. Thus, with fatty acid desaturation as a factor limiting growth of DTY11A, a culture exhibiting significantly increased growth may indicate that the presented fatty acid is utilized as a substrate for desaturation by the expressed ADS desaturase. Table 2 shows that exogenous palmitate facilitates the most growth, followed by stearic acid as the next highest; the same rank order as for the accumulation of 16:1 and 18:1 shown in Table 1.

TABLE 2

Chain length specificity of ADS desaturases expressed in yeast. DTY11A cultures expressing ADS1, ADS2, or ADS3[72-371] were supplied with detergent alone (none), or with saturated fatty acids as indicated, and the growth was monitored. The growth of unsupplemented DTY10A (parent) and of non-transformed DTY11A (non-trans) are shown as controls.

| culture | none | 12:0 | 14:0 | 16:0 | 18:0 | 20:0 | parent | non-transformed |
|---|---|---|---|---|---|---|---|---|
| | | optical density after 20 h | | | | | | |
| DTY11A ADS1 | 0.48 | 0.18 | 0.24 | 0.74 | 0.49 | 0.19 | 0.74 | 0.06 |
| DTY11A ADS2 | 0.46 | 0.19 | 0.25 | 0.76 | 0.39 | 0.24 | 0.74 | 0.08 |
| DTY11A ADS3 72-371 | 0.48 | 0.18 | 0.28 | 0.66 | 0.44 | 0.18 | 0.76 | 0.15 |

In *Arabidopsis*, Expression of ADS1, ADS2, ADS3 and ADS3[72-371] Result in the Accumulation of 16:Δ7, a Fatty Acid that is not Present in Yeast Upon Expression of the Same Genes.

The regiospecificity determined for ADS3 in the yeast complementation experiments conflicted with Mekhedov's prediction that the enzyme would encode a Δ7 desaturase. Thus, the question of whether the observations described above were a result of heterologous expression was examined. To address this question, ADS1, ADS2, ADS3, and ADS3[72-371] were expressed in fab1 fae1 *Arabidopsis* plants under a seed-specific promoter. The fab1 fae1 genetic background was chosen in order to provide the enzymes with optimal substrate availability through elevated palmitic acid levels, and to facilitate the interpretation of resulting fatty acid patterns, because the seeds are impaired in fatty acid elongation beyond 18-carbon fatty acids (which elongated fatty acids would potentially interfere with data analysis).

When transgenic T2 seeds were analyzed by GC/MS for the resulting fatty acids, in addition to the fatty acids found in the equivalent transgenic yeast strains (see Table 1), an additional 16-carbon desaturated fatty acid was observed (Table 3). GC/MS analysis of the DMDS derivatives of desaturated 16-carbon fatty acids from the transgenic seeds showed, that the seeds contained between 1-1.5% (ADS1, ADS2, ADS3[72-371]) and approximately 4% (ADS3) of 16:1 Δ7 in addition to palmitoleic acid (Table 3).

TABLE 3

Generation of 16:1 Δ7 in *Arabidopsis* seeds expressing ADS desaturases. The data below were obtained from GC-traces of fatty acids extracted from non-transformed fab1 fae1 seeds, or from seeds expressing ADS desaturases.

| seeds | 16:0 | 16:1Δ7 | 16:1Δ9 |
|---|---|---|---|
| | % of total fatty acids | | |
| fab1 fae1 | 25.1 | not det. | 1.8 |
| fab1 fae1 ADS1 | 14.7 | 0.7 | 5.2 |
| fab1 fae1 ADS2 | 13.9 | 0.8 | 5.6 |
| fab1 fae1 ADS3 | 17.6 | 4.1 | 1.0 |
| fab1 fae1 ADS3 72-371 | 16.8 | 0.8 | 3.7 |

The T2 seed fatty acid profiles showed several differences from the fab1 fae1 background. Notably, in seeds expressing ADS1, ADS2, or ADS3[72-371], the relative amounts of oleic acid were decreased by 6-9%, whereas those of vaccenic acid were increased by approximately 6%. The levels of 18:2 were unaltered, whereas 18:3 levels were increased by approximately 7-8%. Effects on 18-carbon fatty acids were largely absent from plants expressing the plastid-targeted ADS3.

Figure 3A:
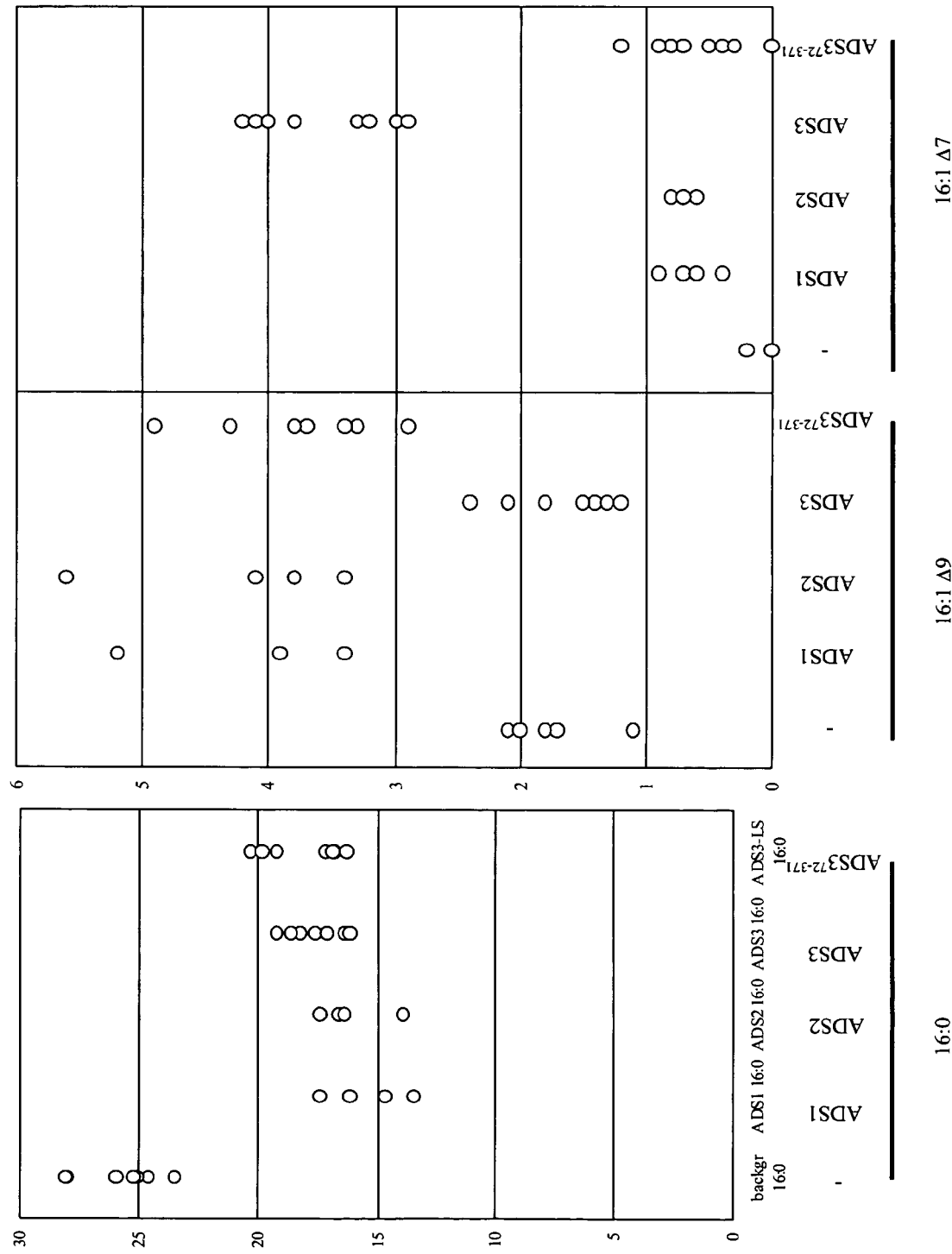
FIG. 3 shows quantitation of fatty acid patterns during expression of ADS desaturases in fab1 fae1 *Arabidopsis* seeds. Panel A, Levels of 16:0, 16:1 Δ9, and 16:1 Δ7. Panel B, Levels of 18:1 Δ9, 18:1 Δ11 and of 18:3. Numbers represent percent of total fatty acids.
Figure 3B:
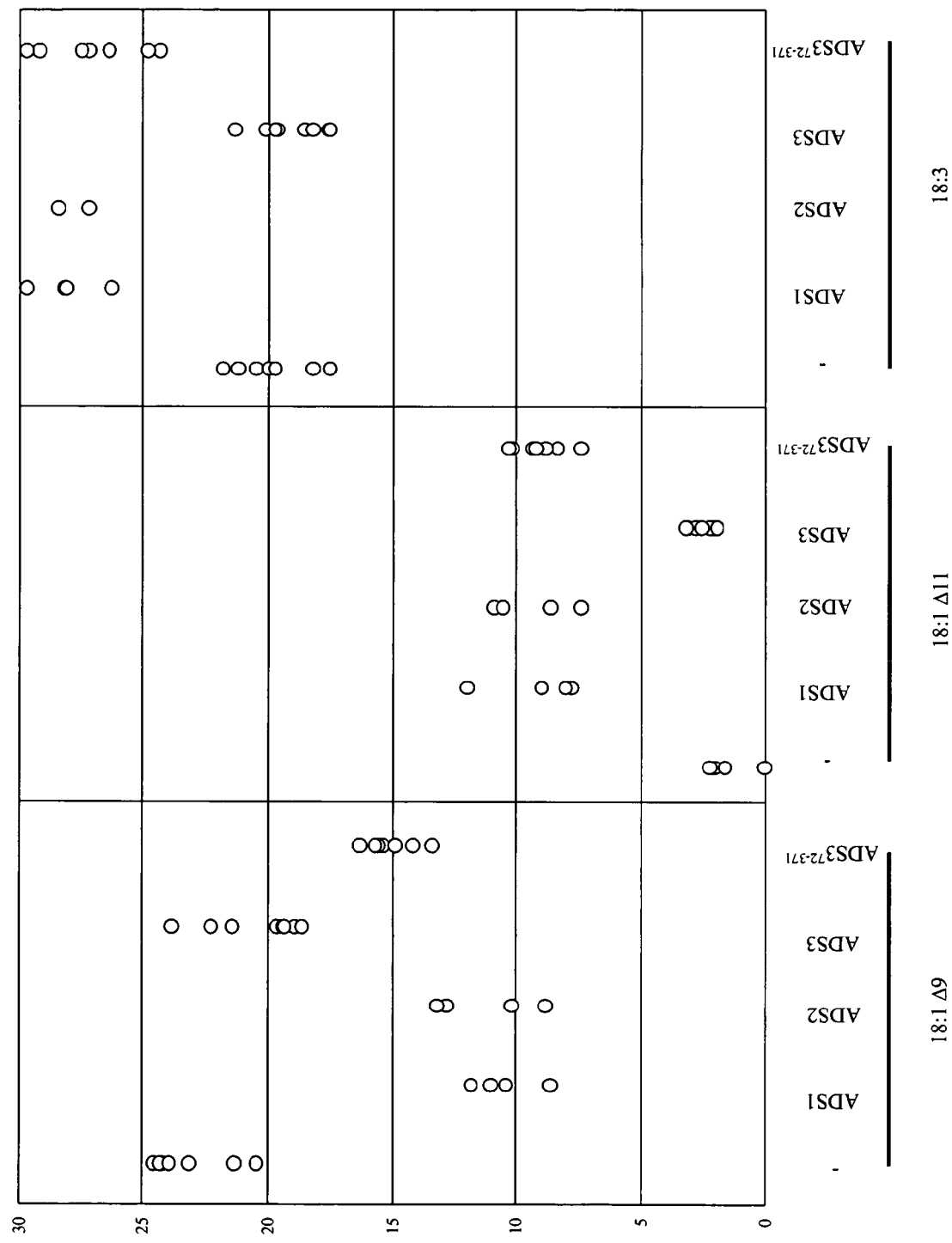

FIG. 3 provides an overview of changes in relative amounts of significant fatty acids in fab1 fae1 seeds expressing the ADS desaturases.

Example 3

Switching of Desaturase Specificity

A. Materials and Methods cDNA Constructs

For yeast expression, cDNAs for ADS1, ADS2 and ADS3 lacking a transit peptide coding sequence (i.e. ADS3[72-371]) were generated by polymerase chain reaction (PCR) from *Arabidopsis* flower cDNA using the primer combinations 5'-GCCTGGATCCATGTCATTGTCAGCCTCG-GAGAAGG-3' (SEQ ID NO:30)/5'-CAGTGAGCTC-CGAGACGTCGTTCCATATCTTCAACG-3'(SEQ ID NO:31), 5'-GCCTGGATCCATGTCGGTGACATCAACG-GTGG-3' (SEQ ID NO:32)/5'-CAGTGAGCTCTCAAC-GAACTATAGCCATACGACG-3' (SEQ ID NO:33), and 5'-GCATGGATCCATGGGAGATTACAGAAGGATA-3' (SEQ ID NO:34)/5'-CAGTGAATTCATACCTTTAAG-TAAACACAAAAAAGC-3' (Primer A; SEQ ID NO:35), respectively. The complete ADS3 coding region was amplified using the primer combination 5'-CAGTGGATC-CTAAGTTAAGGGTTTAAGCCTCTTCTC-3' (SEQ ID NO:36)/Primer A. ADS1, ADS2, and ADS3[72-371] were inserted as BamHI/SacI fragments into Yep352YOPR (Shanklin et al., (1994) Biochemistry 33, 12787-12794) and as BamHI/EcoRI fragments into the yeast expression plasmid pYES2 (Invitrogen). For seed expression, ADS1 and ADS3 were amplified from the respective pYES2 constructs using the primer combinations 5'-GATCTTAATTAAATGTCAT-TGTCAGCCTCG-3' (SEQ ID NO:37)/5'-GATCG-GCGCGCCTCCGAGACGTCGTTCCATATC-3' (SEQ ID NO:38) and 5'-GATCTTAATTAAATGGCTTCTCT-TCTAACA-3' (SEQ ID NO:39)/5'-GATCGGCGCGCCT-CAGTCGCTGGTGAATGC-3' (SEQ ID NO:40), and inserted as PacI/AscI fragments into the plant transformation vector, pBBV-PHAS. ADS2 and ADS3[72-371] sequences in pYES2 were restricted with BamHI, blunted with T4 DNA polymerase, restricted again with XhoI, and then ligated into PmeI/XhoI-restricted pBBV-PHAS. The sequence encoding the ADS3 transit peptide was fused to ADS1 and ADS2 cDNA fragments, creating ADS3[1-71]-ADS1 and ADS3[1-71]-ADS2. First, ADS1 and ADS2 cDNA fragments were amplified from the respective pYES2 constructs using the primer combinations 5'-GCTGCTGCAGCGACGTTGTCATTGT-CAGCC-3' (SEQ ID NO:41)/5'-GGGGACCACTTTGTA-CAAGAAAGCTGGGTTCCGAGACGTCGTTCCATATC-3' (Primer B; (SEQ ID NO:42)) and 5'-GCTGCTGCAGCGACGTTGTCGGTGACAT-CAACGG-3' (SEQ ID NO:43)/5'-GGGGACCACTTTGTA-CAAGAAAGCTGGGTTCAACGAACTATAGCCAT-3' (SEQ ID NO:44) (Primer C), respectively. From an ADS3 template, transit peptide cDNA was amplified for fusion to the ADS1 or ADS2 fragments using the primers 5'-GGGGA-CAAGTTTGTACAAAAAAGCAGGCTATG-GCTTCTCTTCTAACA-3' (Primer D; SEQ ID NO:45)/5'-GGCTGACAATGACAACGTCGCTGCAGCAGC-3' (SEQ ID NO:46) or Primer D/5'-CCGTTGATGTCACCGA-CAACGTCGCTGC-3' (SEQ ID NO:47), respectively. Products were fused by overlap-extension PCR, using Primer D/Primer B and Primer D/Primer C, respectively. The resulting cDNA fragments were moved into PacI/AscI sites of pBBV PHAS.

A *Cucumis sativus* MGDG synthase-glutathione S transferase fusion (15) was used as a template to amplify MGDG synthase cDNA with the primer pair 5'-GATCATCGATATG-GCTTCGTTAGGTGGTGTTTC-3' (SEQ ID NO:48)/5'-GATCGAGCTCTCAGCCGGAATATTGTGGT-3' (SEQ ID NO:49). The cDNA fragment was moved into ClaI/SacI sites of multiple cloning site 1 of pESC-His (Stratagene). All amplifications were carried out with Advantage HF2 DNA polymerase (Clontech). All restriction endonucleases and T4 DNA polymerase were purchased from New England Biolabs.

Transformation and Culture

Yeast transformation was carried out according to Gietz and Woods (Gietz and Woods, R. (1994) in Molecular genetics of yeast: practical approaches., ed. Johnston, J. (Oxford University Press, Oxford, UK), pp. 121-134.). Yeast non-auxotrophic for unsaturated fatty acids (DTY10A) (Toke and Martin, (1996) J Biol Chem 271, 18413-18422) carrying pYES2 constructs were grown at 30° C. in synthetic complete medium without uracil (SC minus ura), pH 6, containing 2% (w/w) raffinose. For ole1Δ (ole1(HPAΔ::LEU2)), 0.5 mM each of palmitoleic and oleic acids was added in final 0.1% (w/w) tergitol. Solid media contained 1.2% (w/w) agar, 18% (w/w) sorbitol, and 1% (w/w) tergitol. For induction, cells were washed in media consisting of SC minus ura plus 2% (w/w) galactose, with no raffinose, palmitoleic or oleic acid supplements, and cultures were inoculated at OD ~0.5. Media were sterilized by filtration (0.2 μm pore size; Nalgene). Growth was monitored at 600 nm, using a spectrophotometer (DU640, Beckmann). For coexpression of MGDG synthase with ADS enzymes, DTY10A cells were transformed simultaneously with MGDG synthase cDNA in pESC-His and with ADS1, ADS2, or ADS3$^{72-371}$ in pYES2. Double transformants were incubated for 5 d at 30° C. on SC minus ura minus his solid media containing 2% (w/w) glucose and subsequently grown in liquid SC minus ura minus his plus 2% (w/w) galactose for 48 h at 30° C., with shaking at 25 rpm.

*Arabidopsis* plants were grown in soil under continuous exposure to ~300 μE of light in controlled environment growth chambers. Seven week-old *Arabidopsis* plants were transformed according to Clough and Bent (Clough and Bent, (1998) Plant J 16, 735-743) using *Agrobacterium tumefaciens* strain GV3101. Plants carrying the transgenes were selected for resistance to ammonium glufosinate (AgrEvo).

Lipid and Fatty Acid Analysis

Lipids were extracted from *Arabidopsis* seeds or yeast cultures according to Bligh and Dyer (Bligh and Dyer, (1959) Can J Biochem Physiol 37, 911-917). Thin layer chromatography (TLC) was performed and lipids visualized (Hartel et al., (2000) Proc Natl Acad Sci USA 97, 10649-10654). MGDG was scraped from TLC plates and redissolved in $CHCl_3$/methanol (2:1, v/v). Positional analysis of fatty acids esterified to MGDG was performed using *Rhizopus arrhizus* lipase (EC.3.1.1.3, Sigma) (Fischer et al., (1973) Z Physiol Chem 354, 1115-1123; Christie, W. W. (2003) Lipid Analysis: Isolation, Separation, Identification and Structural Analysis of Lipids (Barnes and Associates, Bridgewater)). The ensuing lyso-MGDG and free fatty acid fractions were scraped from TLC plates, and redissolved in $CHCl_3$/methanol (2:1, v/v). Fatty acids from purified MGDG or lyso-MGDG were directly methylated using $NaOCH_3$ as described (Domergue et al., (2003) J Biol Chem 278, 35115-35126). Free fatty acids were methylated using 1 ml of 2% (v/v) of $H_2SO_4$ in methanol, incubating for 30 min at 80° C. Fatty acids were extracted from dry cell pellets and methylated by adding 200 μl Boron trichloride ($BCl_3$) directly and incubating for 30 min at 80° C. Fatty acid methyl esters (FAMEs) were re-extracted with 2 ml of hexane and dried under $N_2$. FAMEs of single *Arabidopsis* seeds were prepared according to Butte et al., (Butte et al., (1982) Anal. Lett. 15, 841-850). FAMEs were analyzed using an HP5890 gas chromatograph (Hewlett-Packard) fitted with a 60-m×250 μm SP-2340 capillary column (Supelco). The oven temperature was raised from 100° C. to 240° C. at a rate of 15° C. $min^{-1}$ with a flow rate of 1.1 ml $min^{-1}$. Mass spectrometry was performed with an HP5973 mass selective detector (Hewlett-Packard). Double bond positions of monounsaturated FAMEs were determined (Yamamoto et al., (1991) Chem Phys Lipids 60, 39-50).

Genomic Analysis and Targeting Predictions

All predicted proteins of the *Arabidopsis* genome (2003 annotation of The Institute for Genomic Research) were clustered with the BLASTCLUST program from NCBI using 50% sequence identity and 50% overlap as minimum criteria for proteins to join clusters. To avoid over-clustering, low-complexity regions were masked before this procedure. Three different protein targeting prediction programs were used to estimate putative sub-cellular locations of proteins within each cluster: iPSORT (Nakai and Horton, (1999) Trends Biochem Sci 24, 34-36), Predotar and TargetP) (Emanuelsson et al., (2000) J Mol Biol 300, 1005-1016). Predictions were used when all three programs suggested the same location. Cytosolic localization was assumed when none of the three targeting programs predicted signal or transit peptides and no membrane domains could be predicted with any of the following three prediction programs: HMMTOP (Tusnady and Simon, (2001) Bioinformatics 17, 849-850), Thumbup, and TMHMM (Krogh et al., (2001) J Mol Biol 305, 567-580). The present invention is not limited to a particular mechanism. Indeed, an understanding of the mechanism is not necessary to practice the present invention. Nonetheless, it is contemplated that although computer prediction of protein targeting will likely generate some false positives, the criterion of including only families identified by all three localization prediction algorithms was designed to make the analysis as conservative as possible and therefore, the outcome is an underestimate of the true number. Indeed, in this context the ADS enzyme family is not included in the list, because ADS3 is only predicted to have plastidial targeting by two out of three algorithms, providing a clear example of a false negative.

B. Results

Figure 8:
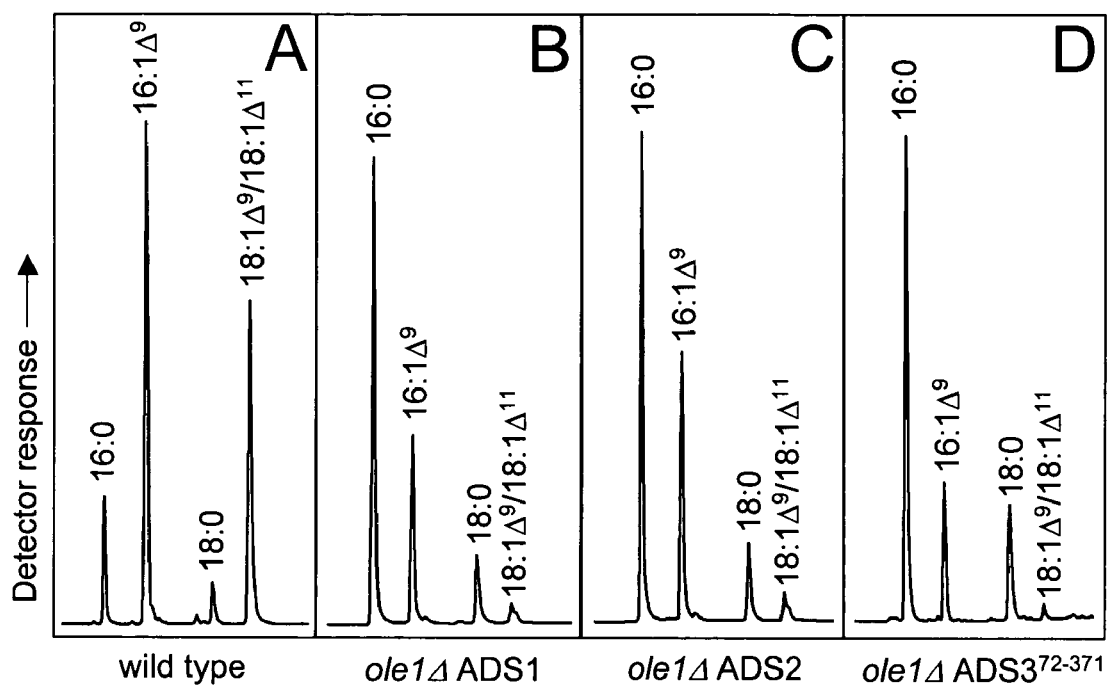
FIG. 8 shows the effect of expressing the *Arabidopsis* desaturase gene ADS 1 (panel B), ADS2 (panel C) or ADS3 (panel D) on fatty acid accumulation in a yeast OLE1 disruption strain grown without unsaturated fatty acid supplementation. Fatty acid accumulation in wild type yeast serves as a control (8A).

Expression of *Arabidopsis* ADS1, ADS2 or ADS3$^{72-371}$ in a yeast OLE1 (Stukey et al., (1989) J Biol Chem 264, 16537-16544) disruption strain restored the ability to grow without unsaturated fatty acid supplementation. Monoenes accumulated to approximately 18-25% of the total fatty acids with palmitoleic, oleic and vaccenic acids being the only detected unsaturates (FIG. 8). The observation of $\Delta^9$- and not $\Delta^7$-desaturation in yeast led to the further characterization of the three ADS genes by expression in *Arabidopsis* plants under the control of a seed-specific promoter. The fab1fae1 genetic background (James and Dooner, (1991) Theor Appl Genet 82, 409-412) was chosen as a host to provide the desaturases with elevated palmitic acid substrate, and to simplify analysis by reducing fatty acid elongation beyond 18-carbons. In contrast to the phenotype observed in yeast, expression of each of the three desaturases, ADS1, ADS2, or ADS3$^{72-371}$, in fab1fae1 *Arabidopsis* seeds resulted in accumulation of 16:1$\Delta^7$ to ~0.7% of the total fatty acids (FIG. 9B-D and Table 4) in addition to an ~9% increase in 16:1$\Delta^9$ and 16:1$\Delta^9$-derived vaccenic acid. A ~6% increase in the elongation product 18:1$\Delta^{11}$, which was likely formed either in the endoplasmic reticulum after desaturation, or by reimport of the 16:1$\Delta^9$ into the plastid was seen. fae1 plants contain some 20-carbon fatty acids (James and Dooner, (1991) Theor Appl Genet 82, 409-412), suggesting either that the fae1 enzyme possesses residual activity or that there is another fae1-like activity. While fab1 plants possess residual plastidial elongation activity it seems unlikely that the 16:1$\Delta^9$ would become esterified to ACP in the plastid in order to become a substrate for fab1. It is possible that the source of this 18-carbon elongation exhibits higher elongation rates with 16- than with 18-carbon substrates.

Expression of ADS3, with its plastidial transit peptide intact, in fab1fae1 seeds resulted in the accumulation of 3.6% 16:1$\Delta^7$ (FIG. 9G), a level 5-fold higher than seen with expression of any ADS enzyme lacking a transit peptide and only an ~1% increase in $\Delta^9$-derived vaccenic acid. This observation raised the question whether targeting of the cytoplasmic ADS1 or ADS2 to the plastid would shift their regiospecificity from $\Delta^9$ to $\Delta^7$. To address this, the DNA encoding the ADS3 transit peptide (ADS3$^{1-71}$) was fused in frame to the ADS1 or ADS2 cDNA fragments, respectively. Expression of ADS3$^{1-71}$-ADS1 and ADS3$^{1-71}$-ADS2 in fab1fae1 seeds resulted in patterns similar to those observed with the expression of full-length ADS3 (FIG. 9E, F) and included increased accumulation of 16:1$\Delta^7$ (~2.5%) in the seeds with only a small increase in 16:1$\Delta^9$-derived vaccenic acid (Table 4). The data indicate an overall 25-70-fold switch in regiospecificity resulting from alternate targeting, with $\Delta^7$:$\Delta^9$ product ratios of ~1:13 (ADS1 and ADS2) to ~1:14 (ADS3$^{72-371}$) when the desaturases were expressed without a transit peptide, and of ~2:1 (ADS3$^{1-71}$-ADS1 and ADS3$^{1-71}$-ADS2) to ~5:1 (ADS3) when they were expressed with a transit peptide. From these experiments it appears that in plants ADS enzymes are capable of functioning within or outside the plastid, that they are bifunctional for the $\Delta^7$- and $\Delta^9$-positions of palmitic acid, and that the ratio of accumulating products depends on their expression with or without a transit peptide rather than on the substantial differences in primary sequence of the catalytic portion of ADS1, ADS2 and ADS3.

Figure 10:
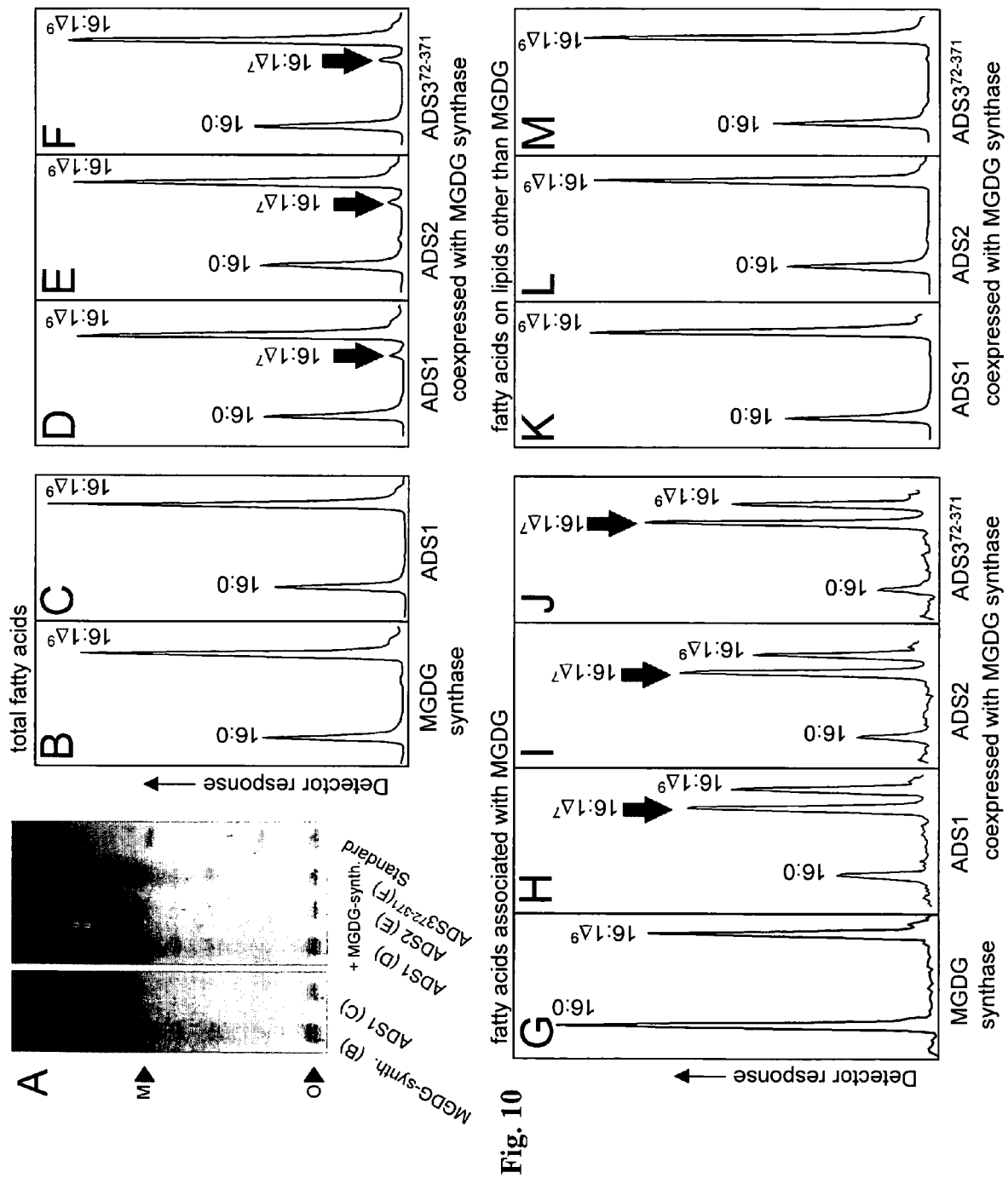
FIG. 10 shows the effect MGDG accumulation on yeast fatty acid regiospecificity by introducing a cucumber MGDG-synthase into the yeast strain DTY10A. Expression of MGDG-synthase is shown (9A). Fatty acid analysis of transgenic yeast lines expressing MGDG-synthase alone (10B and 10G) and expressing the ADS enzyme alone (10C) is shown. The effect of co-expressing ADS1 (10D, 10H, 10K), ADS2 (10E, 10I, 10L) or ADS3$^{72-371}$ (10F, 10J, 10M) with MGDG-synthase on total yeast fatty acids is shown.

The present invention is not limited to a particular mechanism. Indeed, an understanding of the mechanism is not necessary to practice the present invention. Nonetheless, because genetic evidence implies FAD5 desaturates palmitic acid on MGDG in the plastid (Kunst et al., (1989) Plant Physiology 90, 943-947), the possibility that the presentation of palmitic acid on MGDG could modulate regiospecificity and predispose $\Delta^7$-regiospecificity for ADS enzymes was investigated. Yeast were engineered to accumulate MGDG by introducing a cucumber (*Cucumis sativus*) MGDG-synthase (Shimojima et al., (1997) Proc Natl Acad Sci USA 94, 333-337) into the yeast strain DTY10A. Expression of the MGDG-synthase resulted in the appearance of a compound that comigrated with plant MGDG (FIG. 10A) and accumulated to ~1-3 mol % of the total lipid. The identity of this compound was confirmed as MGDG by electrospray ionization tandem mass spectrometry (Kansas Lipidomics Research Center, Kansas State University, Manhattan, Kans.). Fatty acid analysis of transgenic yeast lines indicated that 16:1$\Delta^7$ was absent from cultures expressing the MGDG synthase alone (FIG. 10B, G), from cultures expressing the ADS enzymes alone (e.g., FIG. 10C), and from vector-containing controls. When ADS1, ADS2, or ADS3$^{72-371}$ was coexpressed with MGDG synthase, 16:1$\Delta^7$ accumulated to ~0.8% (ADS1, 2) to 1.5% (ADS3) of the total yeast fatty acids (FIG. 10D-F). While the accumulation of 16:1$\Delta^7$ was less than the increase in the level of 16:1$\Delta^9$-derived vaccenic acid in these yeast strains, it was comparable to the level of accumulation of MGDG itself. Notably, when fatty acids hydrolyzed from the isolated MGDG fraction were analyzed, 16:1$\Delta^7$ was enriched ~15-fold and ~20-fold (ADS1/ADS2 and ADS3$^{72-371}$, respectively) over that of the total lipid fraction with a concomitant decrease in 16:0 (Table 5; and FIG. 10 compare D-F with H-J). No 16:1$\Delta^7$ was detected in total lipid extract after removal of the MGDG fraction (FIG. 10K-M), suggesting that, within detection limits, 16:1$\Delta^7$ occurred exclusively on MGDG.

In 16:3 plants such as *Arabidopsis* and spinach, the successive desaturation of 16:0 to 16:1$\Delta^7$ and further to 16:3 occurs almost exclusively on the sn-2 position of MGDG (Roughan et al., (1979) Biochem J 184, 571-574). However, in yeast, 16:0 is reported to occur almost exclusively on the sn-1 position of all lipids (Wagner, S. and Paltauf, F. (1994) Yeast 10, 1429-1437). In order to determine the position(s) of 16:0 and 16:1$\Delta^7$ on the non-native yeast lipid MDGD, positional analysis was performed on MGDG isolated from yeast expressing the MGDG synthase alone, and from yeast coexpressing MGDG synthase with ADS1, ADS2, or ADS3$^{72-371}$ (Table 5). In a pattern similar to that reported for native yeast lipid species (33), 16:0 and 18:0 were located almost exclusively on the sn-1 position, 18:1 was found almost exclusively on the sn-2 position, and 16:1$\Delta^9$ on both the sn-1 and sn-2 positions of MGDG formed in the transgenic yeast. When ADS1, ADS2 or ADS372-371 was coexpressed with MGDG synthase, the resulting 16:1 $\Delta^7$ was found almost exclusively on the sn-1 position of MGDG (Table 5).

In yeast, the correlation of the formation of 16:1$\Delta^7$ with the synthesis of MGDG raises the question as to whether 16:1$\Delta^7$ formation occurs on MGDG. The following lines of evidence are consistent with desaturation of 16:0 esterified to MGDG: 1) 16:1$\Delta^7$ is formed only in yeast expressing ADS enzymes and containing MGDG (compare FIG. 10C with D-F), 2) The 16:1$\Delta^7$ formed is located exclusively on MGDG and not on other, native yeast lipids, 3) 16:1$\Delta^7$ is restricted to the sn-1 position of MGDG and, 16:1$\Delta^7$-production is accompanied by a concomitant loss of 16:0 (compare FIG. 10G with H-J) at that position. 4) While highly enriched on MGDG, 16:1$\Delta^7$ represents a very minor fraction of the total cellular fatty acid pool (FIG. 10D-F), and therefore the substantial loss of 16:0 specifically from sn-1 of MGDG is most easily explained by 16:0 desaturation directly on the sn-1 position of that lipid. While it is formally possible that 16:0-desaturation to 16:1$\Delta^7$ could take place on CoA, it is difficult to explain why 16:1$\Delta^7$-occurrence would be strictly dependent on the presence of MGDG. If 16:1$\Delta^7$ were synthesized on CoA, it would be expected to be transferred to all yeast lipids, and occur there on both sn-1 and sn-2 positions, based on the distribution of the $\Delta^9$ isomer of 16:1, which is presumably formed by the desaturation of 16:0 esterified to CoA by the yeast-endogenous OLE1 acyl-CoA desaturase (Sperling, P. and Heinz, E. (2001) European J. Lipid Sci. Technol. 103, 158-180). Further, conversion of CoA-bound 16:0 to 16:1$\Delta^7$ would not be expected to cause a substantial concomitant decrease in the global 16:0 pool that would be required to cause the observed 16:0 loss from MGDG (FIG. 10G-J).

In yeast, 16:1$\Delta^7$ occurs almost exclusively on sn-1 of MGDG, whereas in plants 16:1$\Delta^7$-derived 16:3 is found almost exclusively on the sn-2 position of the same lipid. The data suggest that the position on which 16:1$\Delta^7$ will be found in MGDG is a consequence of the position the 16:0 substrate takes on the MGDG glycerol backbone, i.e., the sn-1 position in yeast, and sn-2 in plants, and that the ADS enzymes do not exhibit sn-positional selectivity. Roughan et al., reported that when radiolabeled palmitic acid was supplied to spinach leaves, $\Delta^7$-16:0-desaturation and formation of 16:3 occurred efficiently on the sn-1 position (Roughan et al., (1987) Arch. Biochem. Biophys. 259, 481-496).

The yeast coexpression experiments show that MGDG is both necessary and sufficient to alter the regiospecificity of palmitic acid desaturation by ADS enzymes from $\Delta^9$ to $\Delta^7$. Changes in catalytic rate, but not in regiospecificity, were previously reported for the soluble class of desaturases when substrates were presented on different acyl carrier proteins (Suh et al., (1999) Plant J 17, 679-688). The finding that a lipid head group can act as a molecular switch for desaturase regiospecificity is novel and suggests that assignments of function based solely on heterologous expression in yeast may be inaccurate. While no 16:1$\Delta^7$ accumulation was observed in yeast with the expression of ADS1, ADS2 or ADS3$^{72-371}$ in the absence of MGDG synthase, the low level of 16:1$\Delta^7$ accumulating with extraplastidial targeting of ADS enzymes in fab1fae1 Arabidopsis seeds (FIG. 9B-D) may be explained by the occurrence of low levels of extraplastidial galactolipids in Arabidopsis discussed by Härtel et al. (Hartel et al., (2000) Proc Natl Acad Sci USA 97, 10649-10654); however, it is possible that a fraction of the extraplastidially targeted ADS enzymes acts in the plastid.

TABLE 4

Fatty acid patterns of fab1 fae1 Arabidopsis seeds expressing ADS constructs.

| Fatty Acid | fab1fae1 | ADS1 | ADS2 | ADS3$^{72-371}$ | ADS3$^{1-71}$ – ADS1 | ADS3$^{1-71}$ – ADS2 | ADS3 |
|---|---|---|---|---|---|---|---|
| | | | | mol % ± SD | | | |
| 16:0 | 25.8 ± 1.7 | 15.5 ± 1.7 | 16.1 ± 1.5 | 18.1 ± 1.6 | 18.7 ± 1.9 | 19.2 ± 1.9 | 17.6 ± 1.1 |
| 16:1$\Delta^7$ | n.d. | 0.7 ± 0.2 | 0.7 ± 0.1 | 0.6 ± 0.4 | 2.4 ± 0.5 | 2.6 ± 0.4 | 3.6 ± 0.5 |
| 16:1$\Delta^9$ | 1.8 ± 0.3 | 4.4 ± 0.9 | 4.2 ± 1.0 | 3.8 ± 0.6 | 1.9 ± 0.4 | 1.9 ± 0.4 | 1.7 ± 0.4 |
| 18:0 | 2.6 ± 0.7 | 2.7 ± 0.6 | 2.5 ± 0.8 | 2.4 ± 0.6 | 2.8 ± 0.7 | 2.7 ± 0.5 | 2.9 ± 0.8 |
| 18:1$\Delta^9$ | 23.1 ± 1.6 | 10.5 ± 1.4 | 11.3 ± 2.1 | 15.2 ± 1.0 | 19.8 ± 1.6 | 20.1 ± 1.9 | 20.4 ± 1.9 |
| 18:1$\Delta^{11}$ | 2.8 ± 1.0 | 9.2 ± 1.9 | 9.4 ± 1.6 | 9.1 ± 1.0 | 3.9 ± 0.6 | 4.1 ± 0.8 | 3.6 ± 0.5 |
| 18:2 | 24.9 ± 2.1 | 24.6 ± 2.0 | 26.6 ± 1.8 | 23.1 ± 1.8 | 28.2 ± 2.0 | 28.3 ± 1.9 | 27.9 ± 2.1 |
| 18:3 | 19.8 ± 1.6 | 28.1 ± 1.4 | 28.6 ± 1.2 | 26.9 ± 1.9 | 19.8 ± 1.9 | 19.7 ± 2.0 | 19.1 ± 1.3 |

Data ± standard deviation (SD);
n.d., not detected

TABLE 5

Positional distribution as mol % of fatty acids on MGDG in DTY10A expressing Cucumis sativus MGDG synthase and ADS enzymes as indicated.

| Fatty acid | | | | +ADS1 | | | +ADS2 | | | +ADS3$^{72-371}$ | | |
|---|---|---|---|---|---|---|---|---|---|---|---|---|
| | total | sn-1 | sn-2 | total | sn-1 | sn-2 | total | sn-1 | sn-2 | total | sn-1 | sn-2 |
| 16:0 | 16.4 | 15.1 | 1.5 | 0.5 | 0.7 | n.d. | 1.1 | 0.4 | n.d. | 0.8 | 0.8 | n.d. |
| 16:1$\Delta^7$ | n.d. | n.d. | n.d. | 15.3 | 14.7 | n.d. | 14.4 | 13.7 | n.d. | 17.4 | 16.8 | n.d. |
| 16:1$\Delta^9$ | 12.4 | 6.1 | 6.7 | 13.2 | 6.1 | 7.5 | 14.7 | 7.1 | 7.7 | 13.5 | 3.6 | 8.6 |
| 18:0 | 31.8 | 28.0 | 2.0 | 27.7 | 27.0 | 1.4 | 29.2 | 27.8 | 0.7 | 24.9 | 23.2 | 0.4 |
| 18:1 | 39.5 | 3.2 | 36.6 | 40.1 | 1.3 | 38.7 | 38.9 | 1.8 | 37.1 | 40.2 | 1.4 | 38.1 | n.d., not detectable

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in chemistry, and molecular biology or related fields are intended to be within the scope of the following claims.

We claim:

1. A method of decreasing saturated fatty acid in plant seed oil, comprising:
   a) providing a plant or plant part comprising a heterologous nucleic acid sequence comprising a first nucleic acid sequence operably linked to a seed specific promoter, wherein the first nucleic acid sequence encodes SEQ ID NO: 6 or a protein that is at least 90% identical thereto and which has delta-7 and delta-9 desaturase activity and includes a transit peptide, and
   b) growing the plant or plant part under conditions such that the nucleic acid sequence is expressed such that at least a portion of the saturated fatty acid content in an oil of said plant or plant part becomes desaturated.

2. The method of claim 1, wherein said nucleic acid sequence is SEQ ID NO: 5.

3. The method of claim 1, wherein said saturated fatty acid is palmitic acid or stearic acid.

4. The method of claim 1, wherein said saturated fatty acid is both palmitic acid and stearic acid.

5. The method of claim 1, wherein the concentration of palmitoleic acid and/or vaccenic acid is increased in said plant or plant part.

6. The method of claim 1, wherein said seed specific promoter is selected from the group consisting of a phaseolin promoter, a napin promoter, an oleosin promoter, and a soybean beta conglycin promoter.

7. The method of claim 1, wherein said plant or plant part is selected from the group consisting of a plant cell, a plant tissue, a plant organ, a plant seed and a whole plant.

8. The method of claim 1, wherein said plant is an oil-producing species.

9. The method of claim 8, wherein the oil-producing species is selected from the group consisting of soybean, rapeseed and canola, sunflower, cotton, corn, cocoa, safflower, oil palm, coconut palm, flax, castor, and peanut.

10. The method of claim 1, wherein said saturated fatty acid is a 16:0 fatty acid.

11. The method of claim 1, wherein said saturated fatty acid becomes desaturated at position 7.

12. The method of claim 2, wherein said saturated fatty acid becomes desaturated at position 9.

* * * * *

UNITED STATES PATENT AND TRADEMARK OFFICE
CERTIFICATE OF CORRECTION

PATENT NO. : 7,655,833 B2
APPLICATION NO. : 10/857765
DATED : February 2, 2010
INVENTOR(S) : Heilmann et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 982 days.

Signed and Sealed this

Thirtieth Day of November, 2010

David J. Kappos
*Director of the United States Patent and Trademark Office*

SEQUENCE LISTING

<160> NUMBER OF SEQ ID NOS: 49

<210> SEQ ID NO 1
<211> LENGTH: 918
<212> TYPE: DNA
<213> ORGANISM: Arabidopsis thaliana

<400> SEQUENCE: 1

```
atgtcattgt cagcctcgga gaaggaggag aataacaaga aaatggcagc ggacaaggct      60
gagatgggga ggaagaagag ggcaatgtgg gaaagaaagt ggaagagatt ggacattgtg     120
aaagcttttg catctctctt tgtccatttc ctctgtctct tggcgccttt caatttcact     180
tggccggctt taagagtcgc cctcattgtc tatacggtgg gtgggctcgg tatcaccgtc     240
tcttaccacc gaaatttggc tcaccggagc ttcaaagtcc ctaaatggct cgagtatttc     300
ttcgcttatt gcggccttct tgccattcag ggagatccga ttgattgggt gagcacacat     360
cgataccatc accagtttac agattcggat agggacccac atagtcctaa cgaaggattt     420
tggttcagtc acctcctatg gctatttgat accggttatc ttgtagaaaa gtgtggaaga     480
aggacaaatg tggaggactt aaagaggcag tggtactata aattcctcca agaacagtc      540
ctttaccaca ttctaacatt tggtttcctc ctctattact ttggtggttt gtcttttctt     600
acttggggaa tgggtattgg ggtagcaatg gagcatcatg tgacttgcct cataaactct     660
ctttgccatg tttggggaag ccgaacttgg aagactaatg cacttcccg taacgtttgg      720
tggctatcag tattctcgtt tggagagagc tggcacaaca atcaccacgc cttcgaatcc     780
tcggcgagac aaggcttaga atggtggcaa atcgacattt cttggtatat tgtccgcttt     840
ctcgagatta tcggtttggc tactgatgtt aagttgcctt ccgagagtca acgtcgtcgt     900
atggcaatgg ttcgttga                                                   918
```

<210> SEQ ID NO 2
<211> LENGTH: 305
<212> TYPE: PRT
<213> ORGANISM: Arabidopsis thaliana

<400> SEQUENCE: 2

```
Met Ser Leu Ser Ala Ser Glu Lys Glu Glu Asn Asn Lys Lys Met Ala
1               5                   10                  15

Ala Asp Lys Ala Glu Met Gly Arg Lys Lys Arg Ala Met Trp Glu Arg
            20                  25                  30

Lys Trp Lys Arg Leu Asp Ile Val Lys Ala Phe Ala Ser Leu Phe Val
        35                  40                  45

His Phe Leu Cys Leu Leu Ala Pro Phe Asn Phe Thr Trp Pro Ala Leu
    50                  55                  60

Arg Val Ala Leu Ile Val Tyr Thr Val Gly Gly Leu Gly Ile Thr Val
65                  70                  75                  80

Ser Tyr His Arg Asn Leu Ala His Arg Ser Phe Lys Val Pro Lys Trp
                85                  90                  95
```

-continued

```
Leu Glu Tyr Phe Phe Ala Tyr Cys Gly Leu Leu Ala Ile Gln Gly Asp
                100                 105                 110

Pro Ile Asp Trp Val Ser Thr His Arg Tyr His Gln Phe Thr Asp
    115                 120                 125

Ser Asp Arg Asp Pro His Ser Pro Asn Glu Gly Phe Trp Phe Ser His
    130                 135                 140

Leu Leu Trp Leu Phe Asp Thr Gly Tyr Leu Val Glu Lys Cys Gly Arg
145                 150                 155                 160

Arg Thr Asn Val Glu Asp Leu Lys Arg Gln Trp Tyr Tyr Lys Phe Leu
                165                 170                 175

Gln Arg Thr Val Leu Tyr His Ile Leu Thr Phe Gly Phe Leu Leu Tyr
            180                 185                 190

Tyr Phe Gly Gly Leu Ser Phe Leu Thr Trp Gly Met Gly Ile Gly Val
        195                 200                 205

Ala Met Glu His His Val Thr Cys Leu Ile Asn Ser Leu Cys His Val
    210                 215                 220

Trp Gly Ser Arg Thr Trp Lys Thr Asn Asp Thr Ser Arg Asn Val Trp
225                 230                 235                 240

Trp Leu Ser Val Phe Ser Phe Gly Glu Ser Trp His Asn Asn His His
                245                 250                 255

Ala Phe Glu Ser Ser Ala Arg Gln Gly Leu Glu Trp Trp Gln Ile Asp
            260                 265                 270

Ile Ser Trp Tyr Ile Val Arg Phe Leu Glu Ile Ile Gly Leu Ala Thr
        275                 280                 285

Asp Val Lys Leu Pro Ser Glu Ser Gln Arg Arg Met Ala Met Val
    290                 295                 300

Arg
305

<210> SEQ ID NO 3
<211> LENGTH: 924
<212> TYPE: DNA
<213> ORGANISM: Arabidopsis thaliana

<400> SEQUENCE: 3
atgtcggtga catcaacggt ggaggagaac caccagaaaa atccatcaac gccggcggcg      60
gtggaggaga agaagaagag gagatgggtg ttttgggata aaggtggag gagattagat      120 tatgtgaaat tctcagcttc tttcactgtt cattctcttg ctctcttggc tccgttttat      180
ttcacttggt cggctctttg ggttacgttt ttgttttaca ccatcggtgg tcttggtatc      240
accgtctctt atcatcgcaa cttggctcac cggagtttca agtccctaa atggcttgag      300 tatctcttag cctattgtgc ccttctcgct attcaggag atccgattga ttgggtgagt      360
acacatcgtt accatcacca gttcacggat tcagaacgtg atccacatag tcctaaggaa      420 ggttttggt ttagtcatct tctttggatc tatgactctg cctatcttgt ttcaaagtgt      480
ggaagaagag caaacgtgga ggatttgaag aggcaatggt tttataggtt tcttcagaaa      540
acagtgctat ttcacatttt aggattgggt ttctttctct tctaccttgg tgcatgtcc      600 ttcgttactt ggggaatggg ggtaggagca gcattggaag tgcacgtgac ttgcctcata      660
aattcactct gccatatttg gggcactcga acttggaaga ccaatgacac ttctcgtaat      720
gtttggtggt tatcggtatt tcatttgga gagagttggc acaacaatca tcatgcgttc      780
gagtcatcgg ctagacaagg acttgaatgg tggcaaatag acatttcgtg gtacattgtt      840
```

```
cggtttttcg aaattatcgg tttagcgacc gatgtgaaag tgccaacgga ggctcaacga    900
cgtcgtatgg ctatagttcg ttga                                            924
```

<210> SEQ ID NO 4
<211> LENGTH: 307
<212> TYPE: PRT
<213> ORGANISM: Arabidopsis thaliana

<400> SEQUENCE: 4

```
Met Ser Val Thr Ser Thr Val Glu Glu Asn His Gln Lys Asn Pro Ser
1               5                   10                  15

Thr Pro Ala Ala Val Glu Glu Lys Lys Lys Arg Arg Trp Val Phe Trp
            20                  25                  30

Asp Arg Arg Trp Arg Arg Leu Asp Tyr Val Lys Phe Ser Ala Ser Phe
        35                  40                  45

Thr Val His Ser Leu Ala Leu Leu Ala Pro Phe Tyr Phe Thr Trp Ser
    50                  55                  60

Ala Leu Trp Val Thr Phe Leu Phe Tyr Thr Ile Gly Gly Leu Gly Ile
65                  70                  75                  80

Thr Val Ser Tyr His Arg Asn Leu Ala His Arg Ser Phe Lys Val Pro
                85                  90                  95

Lys Trp Leu Glu Tyr Leu Leu Ala Tyr Cys Ala Leu Leu Ala Ile Gln
            100                 105                 110

Gly Asp Pro Ile Asp Trp Val Ser Thr His Arg Tyr His His Gln Phe
        115                 120                 125

Thr Asp Ser Glu Arg Asp Pro His Ser Pro Lys Glu Gly Phe Trp Phe
    130                 135                 140

Ser His Leu Leu Trp Ile Tyr Asp Ser Ala Tyr Leu Val Ser Lys Cys
145                 150                 155                 160

Gly Arg Arg Ala Asn Val Glu Asp Leu Lys Arg Gln Trp Phe Tyr Arg
                165                 170                 175

Phe Leu Gln Lys Thr Val Leu Phe His Ile Leu Gly Leu Gly Phe Phe
            180                 185                 190

Leu Phe Tyr Leu Gly Gly Met Ser Phe Val Thr Trp Gly Met Gly Val
        195                 200                 205

Gly Ala Ala Leu Glu Val His Val Thr Cys Leu Ile Asn Ser Leu Cys
    210                 215                 220

His Ile Trp Gly Thr Arg Thr Trp Lys Thr Asn Asp Thr Ser Arg Asn
225                 230                 235                 240

Val Trp Trp Leu Ser Val Phe Ser Phe Gly Glu Ser Trp His Asn Asn
                245                 250                 255

His His Ala Phe Glu Ser Ser Ala Arg Gln Gly Leu Glu Trp Trp Gln
            260                 265                 270

Ile Asp Ile Ser Trp Tyr Ile Val Arg Phe Phe Glu Ile Ile Gly Leu
        275                 280                 285

Ala Thr Asp Val Lys Val Pro Thr Glu Ala Gln Arg Arg Met Ala
    290                 295                 300

Ile Val Arg
305
```

<210> SEQ ID NO 5
<211> LENGTH: 1116
<212> TYPE: DNA
<213> ORGANISM: Arabidopsis thaliana

<400> SEQUENCE: 5

```
atggcttctc ttctaacaaa acccaaaccc gttttcctct gttcaccatc gttatctcca      60
agaactttga acacagcaac accgtcattg aatttcacca gaatttcatt cacccatcac     120
caaaagcttg ctcctttcaa gcctcctagt ctcgttgttg cattctctga aagggtttg      180
aagagagatg tcaccacagc tgctgcagcg acggagggag attacagaag gataatgtta     240
tctgatgtgt tggtgaagaa gaaggaaaaa gtagtttggt gggagagaga atggaaagct     300
atggactttg agctgttgc tgtcgttttg tctatgcatt tgcttagtct tttggctccg      360
tttcaattca attggagagc tgtttcggtt gcttttgggc tttatatcgt tacaggtctt     420
ctggggatta ctctgtcttt ccataggaat ctttctcata aagccttcaa gctacctaaa     480
tggcttgagt acttgtttgc ttattgtgga gctcaagctc ttcagggaaa cccaattgat     540
tgggtgagta cacataggta ccatcatcag ttttgtgatt cagacagaga ccctcatagc     600
ccacttgatg ggttttggtt cggtcacatg aattggatgt ttgataccaa tacaatcacc     660
caaaggtgtg gagagcctaa taatgttggg gacttggaga gcagccatt ctatcgattc      720
cttcgaacca cctacatttt gcatccgctg gctctagcgg ttgctttata cgcaatgggt     780
ggctttccat tcatcgtttg gggaatgggg gtaagaatag tatgggtata tcatataact     840
tggctagtga actcagcttg tcatgtatgg ggaaaacaag catggaacac aggcgatttg     900
tctaagaaca actggtgggt agcagctcta gcattcgggg aaggatggca caacaatcac     960
catgcttttg agttctcagc tcgacacggc ttagaatggt ggcaacttga tatgacttgg    1020
tacgtcgtta agttccttca agccatcggt ttagcaactg atgtcaagct cccatcggaa    1080
gctcagaaac aaagaatggc attcaccagc gactga                              1116
```

<210> SEQ ID NO 6
<211> LENGTH: 371
<212> TYPE: PRT
<213> ORGANISM: Arabidopsis thaliana

<400> SEQUENCE: 6

```
Met Ala Ser Leu Leu Thr Lys Pro Lys Pro Val Phe Leu Cys Ser Pro
1               5                   10                  15

Ser Leu Ser Pro Arg Thr Leu Asn Thr Ala Thr Pro Ser Leu Asn Phe
            20                  25                  30

Thr Arg Ile Ser Phe Thr His His Gln Lys Leu Ala Pro Phe Lys Pro
        35                  40                  45

Pro Ser Leu Val Val Ala Phe Ser Glu Lys Gly Leu Lys Arg Asp Val
    50                  55                  60

Thr Thr Ala Ala Ala Thr Glu Gly Asp Tyr Arg Arg Ile Met Leu
65                  70                  75                  80

Ser Asp Val Leu Val Lys Lys Glu Lys Val Val Trp Trp Glu Arg
                85                  90                  95

Glu Trp Lys Ala Met Asp Phe Gly Ala Val Ala Val Leu Ser Met
            100                 105                 110

His Leu Leu Ser Leu Leu Ala Pro Phe Gln Phe Asn Trp Arg Ala Val
        115                 120                 125

Ser Val Ala Phe Gly Leu Tyr Ile Val Thr Gly Leu Leu Gly Ile Thr
    130                 135                 140

Leu Ser Phe His Arg Asn Leu Ser His Lys Ala Phe Lys Leu Pro Lys
145                 150                 155                 160

Trp Leu Glu Tyr Leu Phe Ala Tyr Cys Gly Ala Gln Ala Leu Gln Gly
                165                 170                 175
```

Asn Pro Ile Asp Trp Val Ser Thr His Arg Tyr His His Gln Phe Cys
            180                 185                 190

Asp Ser Asp Arg Asp Pro His Ser Pro Leu Asp Gly Phe Trp Phe Gly
            195                 200                 205

His Met Asn Trp Met Phe Asp Thr Asn Thr Ile Thr Gln Arg Cys Gly
            210                 215                 220

Glu Pro Asn Asn Val Gly Asp Leu Glu Lys Gln Pro Phe Tyr Arg Phe
225                 230                 235                 240

Leu Arg Thr Thr Tyr Ile Leu His Pro Leu Ala Leu Ala Val Ala Leu
            245                 250                 255

Tyr Ala Met Gly Gly Phe Pro Phe Ile Val Trp Gly Met Gly Val Arg
            260                 265                 270

Ile Val Trp Val Tyr His Ile Thr Trp Leu Val Asn Ser Ala Cys His
            275                 280                 285

Val Trp Gly Lys Gln Ala Trp Asn Thr Gly Asp Leu Ser Lys Asn Asn
            290                 295                 300

Trp Trp Val Ala Ala Leu Ala Phe Gly Glu Gly Trp His Asn Asn His
305                 310                 315                 320

His Ala Phe Glu Phe Ser Ala Arg His Gly Leu Glu Trp Trp Gln Leu
            325                 330                 335

Asp Met Thr Trp Tyr Val Val Lys Phe Leu Gln Ala Ile Gly Leu Ala
            340                 345                 350

Thr Asp Val Lys Leu Pro Ser Glu Ala Gln Lys Gln Arg Met Ala Phe
            355                 360                 365

Thr Ser Asp
    370

<210> SEQ ID NO 7
<211> LENGTH: 903
<212> TYPE: DNA
<213> ORGANISM: Arabidopsis thaliana

<400> SEQUENCE: 7
atgggagatt acagaaggat aatgttatct gatgtgttgg tgaagaagaa ggaaaaagta      60
gtttggtggg agagagaatg gaaagctatg gactttggag ctgttgctgt cgttttgtct     120
atgcatttgc ttagtctttt ggctccgttt caattcaatt ggagagctgt ttcggttgct     180
tttgggcttt atatcgttac aggtcttctg gggattactc tgtctttcca taggaatctt     240
tctcataaag ccttcaagct acctaaatgg cttgagtact gtttgctta ttgtggagct      300 caagctcttc agggaaaccc aattgattgg gtgagtacac ataggtacca tcatcagttt     360
tgtgattcag acagagaccc tcatagccca cttgatgggt tttggttcgg tcacatgaat     420
tggatgtttg ataccaatac aatcacccaa aggtgtggag agcctaataa tgttggggac     480
ttggagaagc agccattcta tcgattcctt cgaaccacct acattttgca tccgctggct     540
ctagcggttg ctttatacgc aatgggtggc tttccattca tcgtttgggg aatgggtgta     600
agaatagtat gggtatatca tataacttgg ctagtgaact cagcttgtca tgtatgggga     660
aaacaagcat ggaacacagg cgatttgtct aagaacaact ggtgggtagc agctctagca     720
ttcggggaag gatggcacaa caatcaccat gcttttgagt tctcagctcg acacggctta     780
gaatggtggc aacttgatat gacttggtac gtcgttaagt tccttcaagc catcggttta     840
gcaactgatg tcaagctccc atcggaagct cagaaacaaa gaatggcatt caccagcgac     900
tga                                                                    903

```
<210> SEQ ID NO 8
<211> LENGTH: 300
<212> TYPE: PRT
<213> ORGANISM: Arabidopsis thaliana

<400> SEQUENCE: 8

Met Gly Asp Tyr Arg Arg Ile Met Leu Ser Asp Val Leu Val Lys Lys
1               5                   10                  15

Lys Glu Lys Val Val Trp Trp Glu Arg Glu Trp Lys Ala Met Asp Phe
            20                  25                  30

Gly Ala Val Ala Val Leu Ser Met His Leu Leu Ser Leu Leu Ala
        35                  40                  45

Pro Phe Gln Phe Asn Trp Arg Ala Val Ser Val Ala Phe Gly Leu Tyr
    50                  55                  60

Ile Val Thr Gly Leu Leu Gly Ile Thr Leu Ser Phe His Arg Asn Leu
65                  70                  75                  80

Ser His Lys Ala Phe Lys Leu Pro Lys Trp Leu Glu Tyr Leu Phe Ala
                85                  90                  95

Tyr Cys Gly Ala Gln Ala Leu Gln Gly Asn Pro Ile Asp Trp Val Ser
            100                 105                 110

Thr His Arg Tyr His His Gln Phe Cys Asp Ser Asp Arg Asp Pro His
        115                 120                 125

Ser Pro Leu Asp Gly Phe Trp Phe Gly His Met Asn Trp Met Phe Asp
    130                 135                 140

Thr Asn Thr Ile Thr Gln Arg Cys Gly Glu Pro Asn Asn Val Gly Asp
145                 150                 155                 160

Leu Glu Lys Gln Pro Phe Tyr Arg Phe Leu Arg Thr Thr Tyr Ile Leu
                165                 170                 175

His Pro Leu Ala Leu Ala Val Ala Leu Tyr Ala Met Gly Gly Phe Pro
            180                 185                 190

Phe Ile Val Trp Gly Met Gly Val Arg Ile Val Trp Val Tyr His Ile
        195                 200                 205

Thr Trp Leu Val Asn Ser Ala Cys His Val Trp Gly Lys Gln Ala Trp
    210                 215                 220

Asn Thr Gly Asp Leu Ser Lys Asn Asn Trp Trp Val Ala Ala Leu Ala
225                 230                 235                 240

Phe Gly Glu Gly Trp His Asn Asn His His Ala Phe Glu Phe Ser Ala
                245                 250                 255

Arg His Gly Leu Glu Trp Trp Gln Leu Asp Met Thr Trp Tyr Val Val
            260                 265                 270

Lys Phe Leu Gln Ala Ile Gly Leu Ala Thr Asp Val Lys Leu Pro Ser
        275                 280                 285

Glu Ala Gln Lys Gln Arg Met Ala Phe Thr Ser Asp
    290                 295                 300

<210> SEQ ID NO 9
<211> LENGTH: 35
<212> TYPE: DNA
<213> ORGANISM: Artificial Sequence
<220> FEATURE:
<223> OTHER INFORMATION: Synthetic

<400> SEQUENCE: 9
gcctggatcc atgtcattgt cagcctcgga gaagg                             35
```

```
<210> SEQ ID NO 10
<211> LENGTH: 36
<212> TYPE: DNA
<213> ORGANISM: Artificial Sequence
<220> FEATURE:
<223> OTHER INFORMATION: Synthetic

<400> SEQUENCE: 10
cagtgagctc cgagacgtcg ttccatatct tcaacg                              36

<210> SEQ ID NO 11
<211> LENGTH: 32
<212> TYPE: DNA
<213> ORGANISM: Artificial Sequence
<220> FEATURE:
<223> OTHER INFORMATION: Synthetic

<400> SEQUENCE: 11
gcctggatcc atgtcggtga catcaacggt gg                                  32

<210> SEQ ID NO 12
<211> LENGTH: 34
<212> TYPE: DNA
<213> ORGANISM: Artificial Sequence
<220> FEATURE:
<223> OTHER INFORMATION: Synthetic

<400> SEQUENCE: 12
cagtgagctc tcaacgaact atagccatac gacg                                34

<210> SEQ ID NO 13
<211> LENGTH: 31
<212> TYPE: DNA
<213> ORGANISM: Artificial Sequence
<220> FEATURE:
<223> OTHER INFORMATION: Synthetic

<400> SEQUENCE: 13
gcatggatcc atgggagatt acagaaggat a                                   31

<210> SEQ ID NO 14
<211> LENGTH: 36
<212> TYPE: DNA
<213> ORGANISM: Artificial Sequence
<220> FEATURE:
<223> OTHER INFORMATION: Synthetic

<400> SEQUENCE: 14
cagtgaattc ataccttaa gtaaacacaa aaaagc                               36

<210> SEQ ID NO 15
<211> LENGTH: 36
<212> TYPE: DNA
<213> ORGANISM: Artificial Sequence
<220> FEATURE:
<223> OTHER INFORMATION: Synthetic

<400> SEQUENCE: 15
cagtggatcc taagttaagg gtttaagcct cttctc                              36

<210> SEQ ID NO 16
<211> LENGTH: 30
<212> TYPE: DNA
<213> ORGANISM: Artificial Sequence
<220> FEATURE:
<223> OTHER INFORMATION: Synthetic
```

```
<400> SEQUENCE: 16
gatcttaatt aaatgtcatt gtcagcctcg                                        30

<210> SEQ ID NO 17
<211> LENGTH: 33
<212> TYPE: DNA
<213> ORGANISM: Artificial Sequence
<220> FEATURE:
<223> OTHER INFORMATION: Synthetic

<400> SEQUENCE: 17
gatcggcgcg cctccgagac gtcgttccat atc                                    33

<210> SEQ ID NO 18
<211> LENGTH: 30
<212> TYPE: DNA
<213> ORGANISM: Artificial Sequence
<220> FEATURE:
<223> OTHER INFORMATION: Synthetic

<400> SEQUENCE: 18
gatcttaatt aaatggcttc tcttctaaca                                        30

<210> SEQ ID NO 19
<211> LENGTH: 30
<212> TYPE: DNA
<213> ORGANISM: Artificial Sequence
<220> FEATURE:
<223> OTHER INFORMATION: Synthetic

<400> SEQUENCE: 19
gatcggcgcg cctcagtcgc tggtgaatgc                                        30

<210> SEQ ID NO 20
<211> LENGTH: 30
<212> TYPE: DNA
<213> ORGANISM: Artificial Sequence
<220> FEATURE:
<223> OTHER INFORMATION: Synthetic

<400> SEQUENCE: 20
gctgctgcag cgacgttgtc attgtcagcc                                        30

<210> SEQ ID NO 21
<211> LENGTH: 31
<212> TYPE: DNA
<213> ORGANISM: Artificial Sequence
<220> FEATURE:
<223> OTHER INFORMATION: Synthetic

<400> SEQUENCE: 21
gatctctaga tccgagacgt cgttccatat c                                      31

<210> SEQ ID NO 22
<211> LENGTH: 34
<212> TYPE: DNA
<213> ORGANISM: Artificial Sequence
<220> FEATURE:
<223> OTHER INFORMATION: Synthetic

<400> SEQUENCE: 22
gctgctgcag cgacgttgtc ggtgacatca acgg                                   34

<210> SEQ ID NO 23
<211> LENGTH: 31
```

<210> SEQ ID NO 23
<211> LENGTH: 31
<212> TYPE: DNA
<213> ORGANISM: Artificial Sequence
<220> FEATURE:
<223> OTHER INFORMATION: Synthetic

<400> SEQUENCE: 23
gatctctaga tcaacgaact atagccatac g                31

<210> SEQ ID NO 24
<211> LENGTH: 30
<212> TYPE: DNA
<213> ORGANISM: Artificial Sequence
<220> FEATURE:
<223> OTHER INFORMATION: Synthetic

<400> SEQUENCE: 24
gatcttaatt aaatggcttc tcttctaaca                30

<210> SEQ ID NO 25
<211> LENGTH: 30
<212> TYPE: DNA
<213> ORGANISM: Artificial Sequence
<220> FEATURE:
<223> OTHER INFORMATION: Synthetic

<400> SEQUENCE: 25
ggctgacaat gacaacgtcg ctgcagcagc                30

<210> SEQ ID NO 26
<211> LENGTH: 28
<212> TYPE: DNA
<213> ORGANISM: Artificial Sequence
<220> FEATURE:
<223> OTHER INFORMATION: Synthetic

<400> SEQUENCE: 26
ccgttgatgt caccgacaac gtcgctgc                28

<210> SEQ ID NO 27
<211> LENGTH: 27
<212> TYPE: DNA
<213> ORGANISM: Artificial Sequence
<220> FEATURE:
<223> OTHER INFORMATION: Synthetic

<400> SEQUENCE: 27
gatcgaattc ggattttca caccaca                27

<210> SEQ ID NO 28
<211> LENGTH: 30
<212> TYPE: DNA
<213> ORGANISM: Artificial Sequence
<220> FEATURE:
<223> OTHER INFORMATION: Synthetic

<400> SEQUENCE: 28
gatcttaatt aatatcgatg tgatggctaa                30

<210> SEQ ID NO 29
<211> LENGTH: 28
<212> TYPE: DNA
<213> ORGANISM: Artificial Sequence
<220> FEATURE:
<223> OTHER INFORMATION: Synthetic

<400> SEQUENCE: 29

```
gatctctaga tcagtcgctg gtgaatgc                                              28
```

<210> SEQ ID NO 30
<211> LENGTH: 35
<212> TYPE: DNA
<213> ORGANISM: Artificial Sequence
<220> FEATURE:
<223> OTHER INFORMATION: Synthetic

<400> SEQUENCE: 30

```
gcctggatcc atgtcattgt cagcctcgga gaagg                                      35
```

<210> SEQ ID NO 31
<211> LENGTH: 36
<212> TYPE: DNA
<213> ORGANISM: Artificial Sequence
<220> FEATURE:
<223> OTHER INFORMATION: Synthetic

<400> SEQUENCE: 31

```
cagtgagctc cgagacgtcg ttccatatct tcaacg                                     36
```

<210> SEQ ID NO 32
<211> LENGTH: 32
<212> TYPE: DNA
<213> ORGANISM: Artificial Sequence
<220> FEATURE:
<223> OTHER INFORMATION: Synthetic

<400> SEQUENCE: 32

```
gcctggatcc atgtcggtga catcaacggt gg                                         32
```

<210> SEQ ID NO 33
<211> LENGTH: 34
<212> TYPE: DNA
<213> ORGANISM: Artificial Sequence
<220> FEATURE:
<223> OTHER INFORMATION: Synthetic

<400> SEQUENCE: 33

```
cagtgagctc tcaacgaact atagccatac gacg                                       34
```

<210> SEQ ID NO 34
<211> LENGTH: 31
<212> TYPE: DNA
<213> ORGANISM: Artificial Sequence
<220> FEATURE:
<223> OTHER INFORMATION: Synthetic

<400> SEQUENCE: 34

```
gcatggatcc atgggagatt acagaaggat a                                          31
```

<210> SEQ ID NO 35
<211> LENGTH: 36
<212> TYPE: DNA
<213> ORGANISM: Artificial Sequence
<220> FEATURE:
<223> OTHER INFORMATION: Synthetic

<400> SEQUENCE: 35

```
cagtgaattc atacctttaa gtaaacacaa aaaagc                                     36
```

<210> SEQ ID NO 36
<211> LENGTH: 36
<212> TYPE: DNA
<213> ORGANISM: Artificial Sequence
<220> FEATURE:
<223> OTHER INFORMATION: Synthetic

<400> SEQUENCE: 36
cagtggatcc taagttaagg gtttaagcct cttctc    36

<210> SEQ ID NO 37
<211> LENGTH: 30
<212> TYPE: DNA
<213> ORGANISM: Artificial Sequence
<220> FEATURE:
<223> OTHER INFORMATION: Synthetic

<400> SEQUENCE: 37
gatcttaatt aaatgtcatt gtcagcctcg    30

<210> SEQ ID NO 38
<211> LENGTH: 33
<212> TYPE: DNA
<213> ORGANISM: Artificial Sequence
<220> FEATURE:
<223> OTHER INFORMATION: Synthetic

<400> SEQUENCE: 38
gatcggcgcg cctccgagac gtcgttccat atc    33

<210> SEQ ID NO 39
<211> LENGTH: 30
<212> TYPE: DNA
<213> ORGANISM: Artificial Sequence
<220> FEATURE:
<223> OTHER INFORMATION: Synthetic

<400> SEQUENCE: 39
gatcttaatt aaatggcttc tcttctaaca    30

<210> SEQ ID NO 40
<211> LENGTH: 30
<212> TYPE: DNA
<213> ORGANISM: Artificial Sequence
<220> FEATURE:
<223> OTHER INFORMATION: Synthetic

<400> SEQUENCE: 40
gatcggcgcg cctcagtcgc tggtgaatgc    30

<210> SEQ ID NO 41
<211> LENGTH: 30
<212> TYPE: DNA
<213> ORGANISM: Artificial Sequence
<220> FEATURE:
<223> OTHER INFORMATION: Synthetic

<400> SEQUENCE: 41
gctgctgcag cgacgttgtc attgtcagcc    30

<210> SEQ ID NO 42
<211> LENGTH: 50
<212> TYPE: DNA
<213> ORGANISM: Artificial Sequence
<220> FEATURE:
<223> OTHER INFORMATION: Synthetic

<400> SEQUENCE: 42
ggggaccact ttgtacaaga aagctgggtt ccgagacgtc gttccatatc    50

<210> SEQ ID NO 43
<211> LENGTH: 34
<212> TYPE: DNA
<213> ORGANISM: Artificial Sequence
<220> FEATURE:
<223> OTHER INFORMATION: Synthetic

<400> SEQUENCE: 43
gctgctgcag cgacgttgtc ggtgacatca acgg                    34

<210> SEQ ID NO 44
<211> LENGTH: 47
<212> TYPE: DNA
<213> ORGANISM: Artificial Sequence
<220> FEATURE:
<223> OTHER INFORMATION: Synthetic

<400> SEQUENCE: 44
ggggaccact ttgtacaaga aagctgggtt caacgaacta tagccat       47

<210> SEQ ID NO 45
<211> LENGTH: 47
<212> TYPE: DNA
<213> ORGANISM: Artificial Sequence
<220> FEATURE:
<223> OTHER INFORMATION: Synthetic

<400> SEQUENCE: 45
ggggacaagt ttgtacaaaa aagcaggcta tggcttctct tctaaca       47

<210> SEQ ID NO 46
<211> LENGTH: 30
<212> TYPE: DNA
<213> ORGANISM: Artificial Sequence
<220> FEATURE:
<223> OTHER INFORMATION: Synthetic

<400> SEQUENCE: 46
ggctgacaat gacaacgtcg ctgcagcagc                         30

<210> SEQ ID NO 47
<211> LENGTH: 28
<212> TYPE: DNA
<213> ORGANISM: Artificial Sequence
<220> FEATURE:
<223> OTHER INFORMATION: Synthetic

<400> SEQUENCE: 47
ccgttgatgt caccgacaac gtcgctgc                           28

<210> SEQ ID NO 48
<211> LENGTH: 33
<212> TYPE: DNA
<213> ORGANISM: Artificial Sequence
<220> FEATURE:
<223> OTHER INFORMATION: Synthetic

<400> SEQUENCE: 48
gatcatcgat atggcttcgt taggtggtgt ttc                     33

<210> SEQ ID NO 49
<211> LENGTH: 29
<212> TYPE: DNA
<213> ORGANISM: Artificial Sequence
<220> FEATURE:
<223> OTHER INFORMATION: Synthetic

```
<400> SEQUENCE: 49
gatcgagctc tcagccggaa tattgtggt                                              29
```